(12) United States Patent
Leone-Bay et al.

(10) Patent No.: US 11,246,852 B2
(45) Date of Patent: *Feb. 15, 2022

(54) FAST-ACTING PLANT-BASED MEDICINAL COMPOUNDS AND NUTRITIONAL SUPPLEMENTS

(71) Applicant: RECEPTOR HOLDINGS, INC., Seattle, WA (US)

(72) Inventors: Andrea Leone-Bay, Ridgefield, CT (US); Gregory Wesner, Bainbridge Island, WA (US)

(73) Assignee: Receptor Holdings, Inc., Seattle, WA (US)

( * ) Notice: Subject to any disclaimer, the term of this patent is extended or adjusted under 35 U.S.C. 154(b) by 24 days.

This patent is subject to a terminal disclaimer.

(21) Appl. No.: 16/465,984

(22) PCT Filed: Oct. 6, 2017

(86) PCT No.: PCT/US2017/055547
§ 371 (c)(1),
(2) Date: May 31, 2019

(87) PCT Pub. No.: WO2018/102029
PCT Pub. Date: Jun. 7, 2018

(65) Prior Publication Data
US 2020/0078332 A1 Mar. 12, 2020

Related U.S. Application Data

(60) Provisional application No. 62/429,544, filed on Dec. 2, 2016.

(51) Int. Cl.
| | | |
|---|---|---|
| *A61K 36/73* | (2006.01) | |
| *A61K 36/00* | (2006.01) | |
| *A61K 31/352* | (2006.01) | |
| *A61K 9/00* | (2006.01) | |
| *A61K 31/05* | (2006.01) | |
| *A61K 31/192* | (2006.01) | |
| *A61K 31/353* | (2006.01) | |
| *A61K 33/00* | (2006.01) | |
| *A61K 33/02* | (2006.01) | |
| *A61K 33/06* | (2006.01) | |
| *A61K 36/185* | (2006.01) | |
| *A61K 47/18* | (2017.01) | |
| *A61K 47/22* | (2006.01) | |

(52) U.S. Cl.
CPC .......... *A61K 31/352* (2013.01); *A61K 9/0053* (2013.01); *A61K 31/05* (2013.01); *A61K 31/192* (2013.01); *A61K 31/353* (2013.01); *A61K 33/00* (2013.01); *A61K 33/02* (2013.01); *A61K 33/06* (2013.01); *A61K 36/185* (2013.01); *A61K 47/18* (2013.01); *A61K 47/22* (2013.01); *A61K 2236/333* (2013.01)

(58) Field of Classification Search
None
See application file for complete search history.

(56) References Cited

U.S. PATENT DOCUMENTS

| | | | |
|---|---|---|---|
| 2,385,365 | A | 9/1945 | Link |
| 3,939,259 | A | 2/1976 | Pescetti |
| 4,124,549 | A | 11/1978 | Hashiudo et al. |
| 4,374,082 | A | 2/1983 | Hochschild |
| 4,758,597 | A | 7/1988 | Martin et al. |
| 4,902,513 | A | 2/1990 | Carvais |
| 5,215,754 | A | 6/1993 | Valorose et al. |
| 5,650,386 | A | 7/1997 | Leone-Bay et al. |
| 5,866,536 | A | 2/1999 | Leone-Bay et al. |
| 5,965,162 | A | 10/1999 | Fuisz et al. |
| 6,495,177 | B1 | 12/2002 | deVries et al. |
| 7,745,488 | B2 | 6/2010 | Gagnon et al. |
| 8,022,048 | B2 | 9/2011 | Castelli et al. |
| 8,513,300 | B2 | 8/2013 | Abbas et al. |
| 9,125,833 | B2 | 9/2015 | Babul |
| 9,186,412 | B2 * | 11/2015 | Kidron ................. A61K 9/0053 |
| 10,588,974 | B2 * | 3/2020 | Leone-Bay ........... A23L 33/105 |
| 2002/0065255 | A1 | 5/2002 | Bay et al. |
| 2003/0191069 | A1 | 10/2003 | Inaba |
| 2004/0161819 | A1 | 8/2004 | Aharoni et al. |
| 2004/0224020 | A1 | 11/2004 | Schoenhard |
| 2005/0244490 | A1 | 11/2005 | Otto et al. |

(Continued)

FOREIGN PATENT DOCUMENTS

| | | |
|---|---|---|
| CN | 101439074 A | 5/2009 |
| EP | 2286793 A2 | 2/2011 |

(Continued)

OTHER PUBLICATIONS

Alam, et al., "Protective role of quercetin against hematotoxic and immunotoxic effects of furan in rats," Environ. Sci. Pollut. Res., 2016, 10 pages.
Burstein, "Cannabidiol (CBD) and its analogs: a review of their effects on inflammation," Bioorg. Med. Chem., vol. 23, 2015, pp. 1377-1385.
Office Action dated Apr. 30, 2020 for Colombian Patent Application No. NC2018/0011299, 8 pages.
Office Action dated Oct. 10, 2019 for Eurasian Patent Application No. 201991641, 2 pages.

(Continued)

*Primary Examiner* — Michael Barker
*Assistant Examiner* — Randall O Winston
(74) *Attorney, Agent, or Firm* — Lee & Hayes PC; C. Rachal Winger; Thu Nguyen

(57) ABSTRACT

Plant-based medicinal compounds or nutritional supplements in various carrier combinations are described. The carriers can include N-acylated fatty amino acids, penetration enhancers, and/or various other beneficial carriers. The plant-based composition/carrier combinations can create administration benefits.

20 Claims, 18 Drawing Sheets

(56) References Cited

U.S. PATENT DOCUMENTS

| | | |
|---|---|---|
| 2006/0293354 A1 | 12/2006 | Eatherton |
| 2007/0072939 A1* | 3/2007 | Kupper .................... A61P 1/08 514/454 |
| 2008/0063711 A1 | 3/2008 | Grenier et al. |
| 2008/0103139 A1 | 5/2008 | Ishizuka |
| 2008/0194676 A1 | 8/2008 | Abbas et al. |
| 2009/0155392 A1 | 6/2009 | Nelson et al. |
| 2010/0068297 A1 | 3/2010 | Naughton |
| 2010/0168066 A1 | 7/2010 | Muehlebach |
| 2011/0092583 A1 | 4/2011 | Murty et al. |
| 2011/0137040 A1 | 6/2011 | Lange |
| 2012/0237570 A1 | 9/2012 | Crain et al. |
| 2013/0040910 A1 | 2/2013 | Castelli et al. |
| 2013/0224300 A1 | 8/2013 | Maggio |
| 2013/0295026 A1 | 11/2013 | Viernstein et al. |
| 2014/0154317 A1 | 6/2014 | Al-Mehdar |
| 2014/0193345 A1 | 7/2014 | Levine et al. |
| 2014/0209109 A1 | 7/2014 | Larson |
| 2014/0248211 A1 | 9/2014 | Bender |
| 2014/0271842 A1 | 9/2014 | Herbig et al. |
| 2015/0050373 A1 | 2/2015 | Saklani et al. |
| 2015/0057341 A1 | 2/2015 | Perry |
| 2015/0126595 A1 | 5/2015 | Smith |
| 2015/0126754 A1 | 5/2015 | Fernandez Cid et al. |
| 2015/0132396 A1 | 5/2015 | Coulter et al. |
| 2015/0181925 A1 | 7/2015 | Turner |
| 2015/0273069 A1 | 10/2015 | Bjerregaard et al. |
| 2016/0030436 A1 | 2/2016 | Kim et al. |
| 2016/0355853 A1 | 12/2016 | Winnicki et al. |
| 2018/0263913 A1 | 9/2018 | Lefler et al. |
| 2019/0117778 A1 | 4/2019 | Leone-Bay et al. |
| 2019/0336472 A1 | 11/2019 | Leone-Bay et al. |
| 2020/0101034 A1 | 4/2020 | Leone-Bay et al. |
| 2020/0197521 A1 | 6/2020 | Leone-Bay et al. |
| 2020/0254041 A1 | 8/2020 | Leone-Bay et al. |
| 2020/0268821 A1 | 8/2020 | Leone-Bay et al. |

FOREIGN PATENT DOCUMENTS

| | | |
|---|---|---|
| GB | 2377633 A | 1/2003 |
| JP | 2016509842 A | 4/2016 |
| WO | WO199630036 A1 | 10/1996 |
| WO | WO9808490 A1 | 3/1998 |
| WO | WO0032200 A1 | 6/2000 |
| WO | WO2001019901 A1 | 3/2001 |
| WO | WO0172286 A1 | 10/2001 |
| WO | WO200172286 A1 | 10/2001 |
| WO | WO2003084518 A2 | 10/2003 |
| WO | WO2004026857 A2 | 4/2004 |
| WO | WO2004050011 A2 | 6/2004 |
| WO | WO2005123051 A2 | 6/2005 |
| WO | WO2005065661 A2 | 7/2005 |
| WO | WO2006043260 A2 | 4/2006 |
| WO | WO2006108692 A2 | 10/2006 |
| WO | WO2006134523 A2 | 12/2006 |
| WO | WO2007056242 A1 | 5/2007 |
| WO | WO2007112399 A2 | 10/2007 |
| WO | WO2008024408 A2 | 2/2008 |
| WO | WO2008033024 A2 | 3/2008 |
| WO | WO2008118414 A1 | 3/2008 |
| WO | WO2008122967 A2 | 10/2008 |
| WO | WO2009100245 A1 | 8/2009 |
| WO | WO2010127033 A1 | 11/2010 |
| WO | WO2012069591 A1 | 5/2012 |
| WO | WO2013045115 A1 | 4/2013 |
| WO | WO2013174854 A1 | 11/2013 |
| WO | WO2014159688 A1 | 10/2014 |
| WO | WO2015118549 A1 | 8/2015 |
| WO | WO2015131269 A1 | 9/2015 |
| WO | WO2015198078 A1 | 12/2015 |
| WO | WO2016022936 A1 | 2/2016 |
| WO | WO2016138505 | 9/2016 |
| WO | WO2016205923 A1 | 12/2016 |
| WO | WO2017185038 A1 | 10/2017 |
| WO | WO2018129097 A1 | 7/2018 |
| WO | WO2018175992 A1 | 9/2018 |
| WO | WO2019071211 A1 | 4/2019 |
| WO | WO2020106767 A1 | 5/2020 |

OTHER PUBLICATIONS

Gaffal, et al., "Anti-inflammatory activity of topical THC in DNFB-mediated mouse allergic contact dermatitis independent of CB1 and CB2 receptors," Allergy, vol. 68, No. 8, 2013, pp. 994-1000.

Oh, et al., "Effect of food on the pharmacokinetics of dronabinol oral solution versus dronabinol capsules in healthy volunteers," Clin. Pharmacol., vol. 9, 2017, pp. 9-17.

Olah, et al., "One-Step Conversion of Alicyclic Ketones into Lactams with Hydroxylamine-O-sulfonic Acid/Formic Acid," Synthesis, vol. 7, 1979, pp. 537-538.

PCT Search Report and Written Opinion dated Feb. 3, 2020, of PCT Application No. PCT/US19/62281, 8 pages.

Peana, et al., "Anti-inflammatory activity of linalool and linalyl acetate constituents of essential oils," Phytomedicine, vol. 9, 2002, pp. 721-726.

Peana, et al., "Linalool produces antinociception in two experimental models of pain," Euro. Jour. Pharm., vol. 460, No. 1, 2003, pp. 37-41.

Russo, "Taming THC: potential cannabis synergy and phytocannabinoid-terpenoid entourage effects," BJP, vol. 163, 2011, pp. 1344-1364.

Russo, et al., "A tale of two cannabinoids: the therapeutic rationale for combining tetrahydrocannabinol and cannabidiol," Med. Hypotheses, vol. 66, No. 2, 2006, pp. 234-246.

Wheless, et al., "Pharmacokinetics and Tolerability of Multiple Doses of Pharmaceutical-Grade Synthetic Cannabidiol in Pediatric Patients With Treatment-Resistant Epilepsy," CNS Drugs, vol. 33, No. 6, 2019, pp. 593-604.

The PCT International Preliminary Report on Patentability dated Nov. 1, 2018, for PCT Application No. PCT/US2017/028953, 12 pages.

The PCT Search Report and Written Opinion dated Dec. 28, 2017 for PCT Application No. PCT/US2017/055547, 11 pages.

Stockton, "It Would Take a Lot of THC to Contaminate a Water Supply", Wired, Jul. 22, 2016, https:/www.wired.com/2016/07 /take-lot-the-contaminate-watersupply/, p. 2.

Office Action dated Oct. 20, 2020 in Chilean Application No. 201901471, 15 pages.

Office Action dated Dec. 9, 2020 for Colombian Application No. NC2018/0011299, 11 pages.

Office Action dated Sep. 15, 2020 in European Application No. 17786760.3, 4 pages.

Extended European Search Report dated Nov. 27, 2020 in European Application No. 18770819.3, 9 pages.

Office Action dated Oct. 1, 2020 in Mexican Application No. MX/a/2019/006439, 4 pages.

Examination Report dated Nov. 10, 2020 in New Zealand Application No. 747886, 5 pages.

Examination Report dated Nov. 23, 2020 for New Zealand Application No. 754983, 5 pages.

McCartney, et al, "Safety concerns over the use of intestinal permeation enhancers: A mini-review," Tissue Barriers, vol. 4, No. 2, 2016, 14 pages.

Mechoulam, et al., "A Total Synthesis of dl-delta-Tetrahydrocannabinol, the Active Constituent of Hashish," J. Am. Chem. Soc., vol. 87, No. 14, 1965, pp. 3273-3275.

Muller et al, "Preparation and characterization of mucus-penetrating papain/poly(acrylic acid) nanoparticles for oral drug delivery applications", Journal of Nanoparticle Research, vol. 15, published online Dec. 16, 2012, pp. 1-13.

Nissen, et al., "Characterization and antimicrobial activity of essential oils of industrial hemp varieties (*Cannabis sativa* L.)," Fitoterapia, vol. 81, No. 5, 2010, pp. 413-419.

O'Connell and Bov-Matar, "Long term marijuana users seeking medical cannabis in California (2001-2007): demographics, social characteristics, patterns of cannabis and other drug use of 4117 applicants," Harm Reduct. J., vol. 4, 2007, 7 pages.

(56) References Cited

OTHER PUBLICATIONS

Office Action dated Oct. 3, 2019 for U.S. Appl. No. 16/094,802, 5 pages.
Olah, et al., "Synthetic Methods and Reactions; 671. One-Step Conversion of Alicyclic Ketones into Lactams with Hydroxylamine-O-sulfonic Acid/Formic Acid," Synthesis, 1979, pp. 537-538.
Paula-Freire, et al., "Ocimum gratissimum Essential Oil and Its Isolated Compounds (Eugenol and Myrcene) Reduce Neuropathic Pain in Mice," Planta Med., vol. 82, No. 3, 2016, pp. 211-216.
Invitation to Pay Additional Fees dated Mar. 6, 2018 for International Application No. PCT/US2018/012261, 2 pages.
Invitation to Pay Additional Fees dated Jun. 29, 2018 for International Application No. PCT/US2018/024188, 2 pages.
Search Report and Written Opinion dated Nov. 29, 2018 for International Application No. PCT/US2018/054733, 21 pages.
Search Report and Written Opinion dated Dec. 12, 2018 for International Application No. PCT/US2018/054728, 17 pages.
Search Report and Written Opinion dated Apr. 26, 2018, for International Application No. PCT/US2018/012261, 11 pages.
Seach Report and Written Opinion dated Jul. 21, 2017 for International Application No. PCT/US17/28953, 13 pages.
Search Report and Written Opinion dated Aug. 29, 2018 for International Application No. PCT/US2018/024188, 14 pages.
Perry, et al., "In vitro inhibition of human erythrocyte acetylcholinesterase by Salvia lavandulaefolia essential oil and constituent terpenes," Journal of Pharmacy and Pharmacology, vol. 52, No. 7, 2010, pp. 895-902.
Petrzilka, et al., "Synthese und Chiralitat des (-)-Cannabidiols Vorlaufige Mitteilung," Helv. Chim. Acta, vol. 50, No. 2, 1967, pp. 719-723.
Piccinelli, et al., "Limonene reduces hyperalgesia induced by gp120 and cytokines by modulation of IL-1 Beta and protein expression in spinal cord of mice," Life Sci., vol. 174, 2017, pp. 28-34.
PubChem, "Salcaprozate Sodium", retrieved on Nov. 29, 2018 at <<https://pubchem.ncbi.nlm.nih.gov/compound/Salcaprozate sodium#section=Information-Sources>>, Feb. 5, 2008, pp. 1-17.
Raman, et al., "Amyotrophic lateral sclerosis: delayed disease progression in mice by treatment with a cannabinoid," Amyotroph Lateral Scler. Other Motor Neuron Disord., vol. 5, No. 1, 2004, pp. 33-39.
Rao, et al., "Effect of myrcene on nociception in mice," J. Pharm. Pharmacol., vol. 42, No. 12, 1990, pp. 877-878.
Resstel, et al., "5-HT1A receptors are involved in the cannabidiol-induced attenuation of behavioural and cardiovascular responses to acute restraint stress in rats," Br. J. Pharmacol., vol. 156, No. 1, 2009, pp. 181-188.
Rice, et al., "Characterizing the Smell of Marijuana by Odor Impact of Volatile Compounds: An Application of Simultaneous Chemical and Sensory Analysis," vol. 10, No. 12, 2015, pp. 1-17.
Robson, "Therapeutic aspects of cannabis and cannabinoids," Br. J. Psychiatry, vol. 178, No. 2, 2001, pp. 107-115.
Rothschild, et al., "Cannabis sativa: volatile compounds from pollen and entire male and female plants of two variants, Northern Lights and Hawaian Indica," Botanical Journal of the Linnean Society, vol. 147, No. 4, 2005, pp. 387-397.
Salgueiro, et al., "Anxiolytic Natural and Synthetic Flavonoid Ligands of the Central Benzodiazepine Receptor Have No Effect on Memory Tasks in Rats," Pharmacol. Biochem. Behav., vol. 58, No. 4, 1997, pp. 887-891.
Schaeffer, "5 Supplements That Can Treat Migraines", retrieved at <<https://www.healthline.com/health/migraine/migraine-vitamins#1>>, Healthline, Mar. 24, 2016, 11 pages.
Shohami, et al., "Endocannabinoids and traumatic brain injury," Br. J. Pharmacol., vol. 163, No. 7, 2011, pp. 1402-1410.
Sieradzan, et al., "Cannabinoids reduce levodopa-induced dyskinesia in Parkinson's disease: a pilot study," Neurology, vol. 57, No. 11, 2001, pp. 2108-2111.
Souto-Maior, et al., "Anxiolytic-like effects of inhaled linalool oxide in experimental mouse anxiety models," Pharmacol. Biochem. Behav., vol. 100, No. 2, 2011, pp. 259-263.

Syed, et al., "Delta-9-Tetrahydrocannabinol/Cannabidiol (Sativex) A Review of Its Use in Patients with Moderate to Severe Spasticity Due to Multiple Sclerosis," Drugs, vol. 74, No. 5, 2014, pp. 563-578.
Tarapore, et al., "The dietary terpene lupeol targets colorectal cancer cells with constitutively active Wnt/beta-catenin signaling", Molecular Nutrition and Food Research, vol. 57, No. 11, 2013, 2013, pp. 1950-1958.
Tashkin, et al., "Effects of smoked marijuana in experimentally induced asthma," Am. Rev. Respir. Dis., vol. 112, No. 3, 1975, pp. 377-386.
Victorio, et al., "Flavonoid extraction from *Alpinia zerumbet* (Pers.) Burttet Smith leaves using different techniques and solvents," Ecl. Quinn., vol. 34, No. 1, 2009, pp. 19-24.
Vuolo, et al., "Evaluation of Serum Cytokines Levels and the Role of Cannabidiol Treatment in Animal Model of Asthma," Mediators of Inflammation, vol. 2015, No. 538670, 5 pages.
Walsh, et al., "Acute administration of cannabidiol in vivo suppresses ischaemia-induced cardiac arrhythmias and reduces infarct size when given at reperfusion," Br. J. Pharmacol., vol. 160, No. 5, 2010, pp. 1234-1242.
Zanelati, et al., "Antidepressant-like effects of cannabidiol in mice: possible involvement of 5-HT1A receptors," Br. J. Pharmacol., vol. 159, No. 1, 2010, pp. 122-128.
Office Action dated Jul. 31, 2020 in Chilean Application No. 201802997, 21 pages.
Office Action dated Sep. 14, 2020 in Chilean Application No. 201901832, 12 pages.
Office Action dated Sep. 2, 2020 in Chinese Application No. 201780024997.6, 9 pages.
Extended European Search Report dated Jun. 15, 2020 for the European Patent Application No. 17875177.2, 7 pages.
Extended European Search Report dated Jul. 9, 2020 for European Application No. 18736204.1, 10 pages.
Examination Report dated Oct. 22, 2020 in Indian Application No. 201817039884, 5 pages.
Office Action dated Aug. 11, 2020 in Mexican Application No. MX/a/2018/012913, 3 pages.
Office Action dated Sep. 22, 2020 in Mexican Application No. MX/a/2019/007968, 3 pages.
Office Action dated Oct. 29, 2020 for U.S. Appl. No. 16/805,356, 5 pages.
Abramovici, "Information for Health Care Providers Cannabis and the Cannabinoids," Health Canada, 2013.
Aungst, et al., "Absorption Enhancers: Applications and Advances", The AAPS Journal, vol. 14, No. 1, 2012, pp. 10-18.
Bab, et al., "Cannabinoids and the skeleton: from marijuana to reversal of bone loss," Ann. Med., vol. 41, No. 8, 2009, pp. 560-567.
Babaee, et al., "Antioxidant capacity of calendula officinalis flowers extract and prevention of radiation induced propharyngeal mucositis in patients with head and neck cancers: a randomized controlled clinical study," J. of Pharmaceutical Sciences, vol. 21, No. 18, 2013, pp. 1-7.
Bahi, et al.,"Beta-Caryophyllene, a CB2 receptor agonist produces multiple behavioral changes relevant to anxiety and depression in mice," Physiol. Behav., vol. 135, 2014, pp. 119-124.
Baker and Pryce, "The therapeutic potential of cannabis in multiple sclerosis," Expert Opin. Investig. Drugs, vol. 12, No. 4, 2003, pp. 561-567.
Barrett, et al., "Cannflavin A and B, prenylated flavones from *Cannabis sativa* L.," Experientia, vol. 42, No. 4, 1986, pp. 452-453.
Basavarajappa and Hungund, "Role of the endocannabinoid system in the development of tolerance to alcohol," Alcohol Alcohol., vol. 40, No. 1, 2005, pp. 15-24.
Baughman, et al., "Oral delivery of anticoagulant doses of heparin. A randomized, double-blind, controlled study in humans," Circulation, vol. 98, No. 16, 1998, pp. 1610-1615.
Beal, et al., "Dronabinol as a treatment for anorexia associated with weight loss in patients with AIDS," J. Pain. Symptom Manage., vol. 10, No. 2, 1995, pp. 89-97.
Binet, et al., "Pharmacodynamic properties (sedative action and spasmolytic action) of several aliphatic terpene alcohols," Ann. Pharm. Fr., vol. 30, No. 9, 1972, pp. 611-616.

(56) References Cited

OTHER PUBLICATIONS

Biro, et al., "The endocannabinoid system of the skin in health and disease: novel perspectives and therapeutic opportunities," Trends Pharmacol. Sci., vol. 30, No. 8, 2009, pp. 411-420.
Bittner, et al., "Phase I clinical study to select a novel oral formulation for ibandronate containing the excipient sodium N-[8-(2-hydroxybenzoyl) amino] caprylate (SNAC)", Pharmazie, vol. 67, 2012, pp. 233-241.
Brenneisen, "Chemistry and Analysis of Phytocannabinoids and Other Cannabis Constituents," Humana Press Inc., Totowa, New Jersey, 2007, pp. 17-49.
Burstein and Zurier "Cannabinoids, endocannabinoids, and related analogs in inflammation," AAPS J., vol. 11, No. 1, 2009, pp. 109-119.
Calderon-Montano, et al., "A Review on the Dietary Flavonoid Kaempferol," Mini. Rev. Med. Chem., vol. 11, No. 4, 2011, pp. 298-344.
Campos, et al., "Cannabidiol, neuroprotection and neuropsychiatric disorders," Pharmacol. Res., vol. 112, 2016, pp. 119-127.
Cardi, et al., "Superiority of Laparoscopy Compared to Ultrasonography in Diagnosis of Widespread Liver Diseases," Dig. Dis. Sci., vol. 42, No. 3, 1997, pp. 546-547.
Castelli, et al., "Pharmacokinetics of Oral Cyanocobalamin Formulated with Sodium N-[8-(2-hydroxybenzoyl)amino] caprylate (SNAC): An Open-Label, Randomized, Single-Dose, Parallel-Group Study in Healthy Male Subjects," Clinical Terapeutics, vol. 33, No. 7, 2011, pp. 934-945.
De Vries, et al., "Cannabinoid modulation of the reinforcing and motivational properties of heroin and heroin-associated cues in rats," Psychopharmacology [Berl], vol. 168, No. 1-2, 2003, pp. 164-169.
Ding, et. al., "Oral Absorption Enhancement of Cromolyn Sodium Through Noncovalent Complexation," Pharmaceutical Research, vol. 21, No. 12, 2004, pp. 2196-2206.
Office Action dated Nov. 12, 2019 for Eurasian Patent Application No. 201892396, 6 pages.
Office Action dated Aug. 30, 2019 for Eurasian Patent Application No. 201991289, 3 pages.
Extended European Search Report dated Oct. 17, 2019 for European Patent Application No. 17786760.3, 7 pages.
Epps, et al., "Synergistic Endo- and Exo-Interactions Between Blueberry Phenolic Compounds, Grape Variety Fractions, Chocolate Covered Strawberries, and Fruit Smoothies," J. of Food Res., vol. 2, No. 6, 2013, pp. 33-47.
Eubanks, et al., "A molecular link between the active component of marijuana and Alzheimer's disease pathology," Mol. Pharm., vol. 3, No. 6, 2006, pp. 773-777.
Falk, et al., "Uptake, distribution and elimination of alpha-pinene in man after exposure by inhalation," Scand. J. Work Environ. Health, vol. 16, No. 5, 1990, pp. 372-378.
Florence, "The Oral Absorption of Micro- and Nanoparticulates: Neither Exceptional Nor Unusual," Pharm. Res., vol. 14, No. 3, 1997, pp. 259-266.
Gertsch, et al., "Beta-caryophyllene is a dietary cannabinoid," PNAS, vol. 105, No. 26, 2008, pp. 9099-9104.
Gil, et al., "Comparative study of different essential oils of Bupleurum gibraltaricum Lamarck," Pharmazie, vol. 44, No. 4, 1989, pp. 284-287.
Grivennikov, et al, "Immunity, Inflammation, and Cancer," Cell, vol. 140, No. 6, 2010, pp. 883-899.
Grotenhermen, et al., "The Therapeutic Potential of Cannabis and Cannabinoids," Dtsch Arztebl Int., vol. 109, No. 29-30, 2012, pp. 495-501.
Guimaraes-Santos, et al., "Copaiba Oil-Resin Treatment Is Neuroprotective and Reduces Neutrophil Recruitment and Microglia Activation after Motor Cortex Excitotoxic Injury," J. Evid. Based Complementary Altern. Med., vol. 2012, 2012, pp. 1-9.
Guindon and Hohmann, "The endocannabinoid system and cancer: therapeutic implication," Br. J. Pharmacol., vol. 163, No. 7, 2011, pp. 1447-1463.
Guzman, "Cannabinoids: Potential Anticancer Agents," Nat. Rev. Cancer, vol. 3, 2003, pp. 745-755.
Hess, et. al., "Investigation of the Enhancing Mechanism of Sodium N-[8-(2-hydroxybenzoyl)amino]caprylate effect of the Intestinal Permeability of Polar Molecules Utilizing a Voltage Clamp Method," Departement of Pharmaceutics, European Journal of Pharmaceutical Science 25, Apr. 11, 2005, pp. 307-312.
Holdcroft, et al., "Clinical Trial Experience with Cannabinoids," Pharm. Sci., vol. 3, 1997, pp. 546-550.
Inoue, et al., "The Antibacterial Effects of Myrcene on *Staphylococcus aureus* and Its Role in the Essential Oil of the Tea Tree (*Melaleuca alternifolia*)," Nat. Med., vol. 58, No. 1, 2004, pp. 10-14.
Katsuyama, et al., "Involvement of peripheral cannabinoid and opioid receptors in Beta-caryophyllene-induced antinociception," Eur. J. Pain, vol. 17, No. 5, 2013, pp. 664-675.
Kidron, et al., "A novel per-oral insulin formulation: proof of concept study in non-diabetic subjects," Diabet. Med., vol. 21, No. 4, 2004, pp. 354-357.
Kobayashi, et al., "Synthesis of Cannabidiols via Alkenylation of Cyclohexenyl Monoacetate," J. Am. Chem. Soc., vol. 8, No. 13, 2006, pp. 2699-2702.
Komori, et al., "Potential antidepressant effects of lemon odor in rats," Euro. Neuropsychopharmacology, vol. 5, No. 4, 1995, pp. 477-480.
Kremer et al., "Pharmacokinetics, pharmacodynamics and tolerability of oral cromolyn sodium/SNAC capsules in healthy and allergic male subjects," Br. J. Clin. Pharmacol., vol. 56, 2003, pp. 467-468.
Lam, et al., "A Review on Medicinal Properties of Orientin," Adv. Pharmacol. Sci., vol. 2016, 2016, 9 pages.
Lastres-Becker, et al., "Compounds acting at the endocannabinoid and/or endovanilloid systems reduce hyperkinesia in a rat model of Huntington's disease," J. Neurochem., vol. 84, No. 5, 2003 , pp. 1097-1109.
Leone-Bay, et al., "Synthesis and evaluation of compounds that facilitate the gastrointestinal absorption of heparin", J. Med. Chem., vol. 41, No. 7, 1998, pp. 1163-1171.
Linck, et al., "Effects of inhaled Linalool in anxiety, social interaction and aggressive behavior in mice," Phytomedicine, vol. 17, No. 8-9, 2002, pp. 679-683.
Lorenzetti, et al., "Myrcene mimics the peripheral analgesic activity of lemongrass tea," J. of Ethnopharmacology, vol. 34, No. 1, 1991, pp. 43-48.
Lyman, et al., "Delta 9-tetrahydrocannabinol: a novel treatment for experimental autoimmune encephalomyelitis," J. Neuroimmunol., vol. 23, No. 1, 1989, pp. 73-81.
Martyn, et al., "Nabilone in the treatment of multiple sclerosis," Lancet, vol. 345, No. 8949, 1995, p. 579.
Choudhary, et al., "Development and characterization of an atorvastatin solid dispersion formula using skimmed milk for improved oral bioavailability," Acta Pharmaceutica Sinica B, vol. 2, No. 4, 2012, pp. 421-428.
Heckelman, et al, The Merck Index: an encyclopedia of chemicals, drugs, and biologicals, (No. 615.11 MER), p. 146.
Final Office Action dated Jul. 27, 2021 in U.S. Appl. No. 16/474,480, 15 pages.
Castelli, et al., "Comparing the Efficacy and Tolerability of a New Daily Oral Vitamin B12 Formulation and Intermittent Intramuscular Vitamin B12 in Normalizing Low Cobalamin Levels: A Randomized, Open-Label, Parallel-Group Study," Clin. Ther., vol. 33, No. 3, 2011, pp. 358-371.
Office Action dated Apr. 20, 2021 in Chinese Application No. 201780024997.6, 6 pages.
Partial Search Report dated Apr. 28, 2021 in European Application No. 18865203.6, 16 pages.
Office Action dated Dec. 31, 2020 in Israel Application No. 262505, 4 pages.
Office Action dated Mar. 16, 2021 in Japanese Application No. 2019-506612, 5 pages.
Maher, et al., "Intestinal permeation enhancers for oral peptide delivery," Adv. Drug Del. Rev., vol. 106, 2016, pp. 277-319.
Office Action dated Mar. 26, 2021 in U.S. Appl. No. 16/465,984, 9 pages.

(56) References Cited

OTHER PUBLICATIONS

Yadav, et al., "Effect of Cyclodextrin Complexation of Curcumin on its Solubility and Antiangiogenic and Anti-inflammatory Activity in Rat Colitis Model," AAPS Pharm. Sci. Tech. vol. 10, No. 3, 2009, 11 pages.

"Cannabis (Marijuana) and Cannabinoids: What You Need to Know." National Center for Complementary and Integrative Health, U.S. Department of Health and Human Services, 2019, https://www.nccih.nih.gov/health/cannabis-marijuana-and-cannabinoids-what-you-need-to-know. Retrieved Nov. 29, 2021.

Office Action dated Oct. 19, 2021 in Japanese Application No. 2019-536222, 4 pages.

Office Action dated Oct. 20, 2021 for Mexican Application No. MX/a/2019/007968, 4 pages.

Office Action dated Nov. 29, 2021 in U.S. Appl. No. 16/753,721, 10 pages.

Office Action dated Dec. 7, 2021 in U.S. Appl. No. 16/474,480, 14 pages.

\* cited by examiner

| Name | Structure | Name | Structure |
|---|---|---|---|
| CBC | 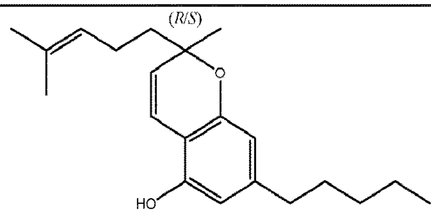 | CBN | 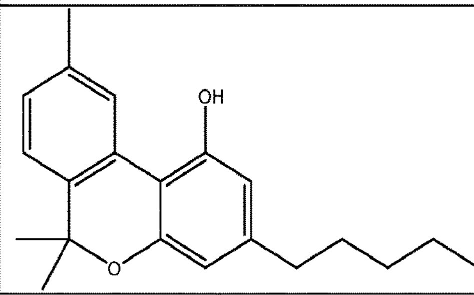 |
| CBCV | 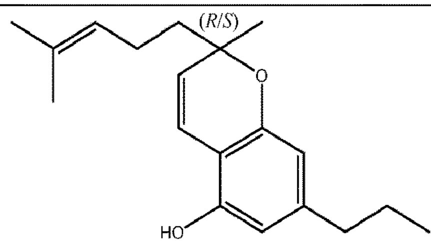 | CBNV | 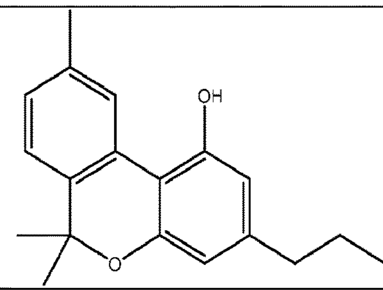 |
| CBD | 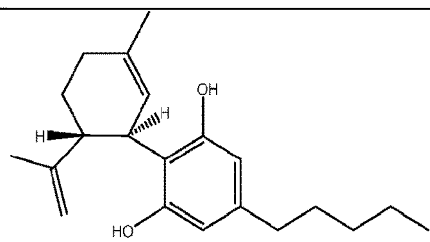 | CBO | 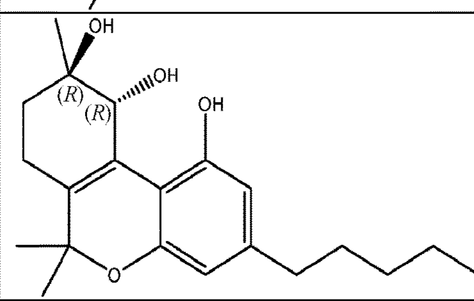 |
| CBDA | 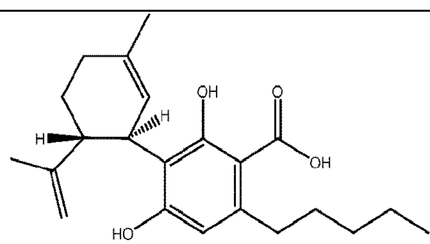 | THC | 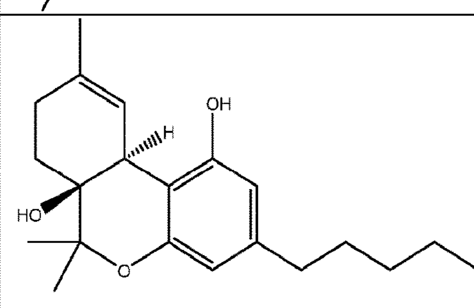 |

FIG. 2 cont'd

| Name | Structure | Name | Structure |
|------|-----------|------|-----------|
| CBDV | 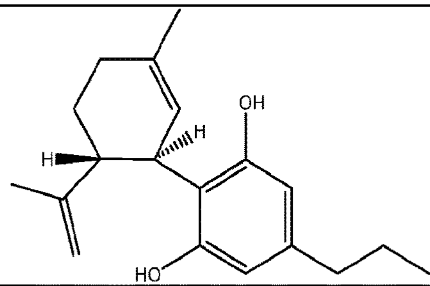 | THCA | 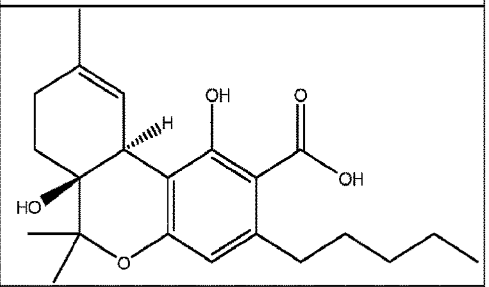 |
| CBG | 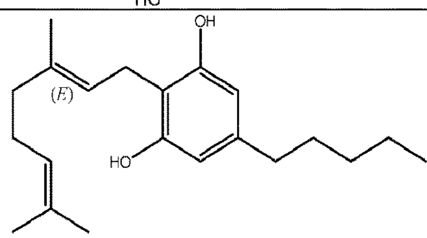 | THCV | 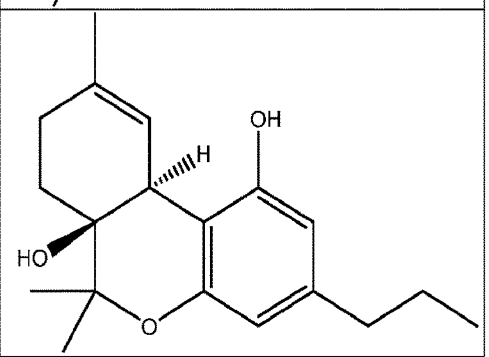 |
| CBGV | 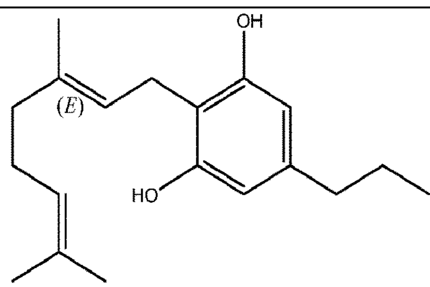 | THCVA | 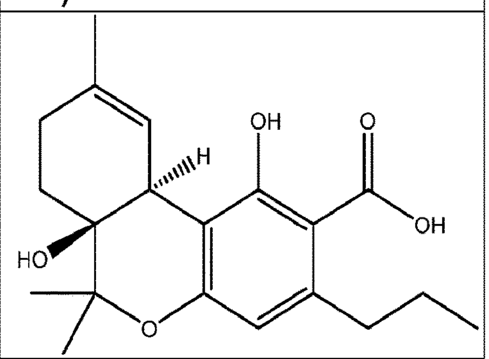 |
| CBL | 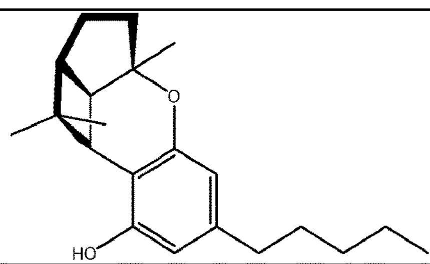 | | |

| # | Structure |
|---|---|
| I | 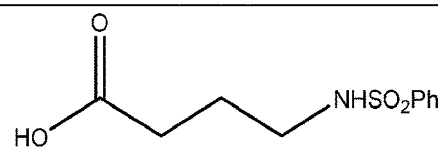 |
| II | 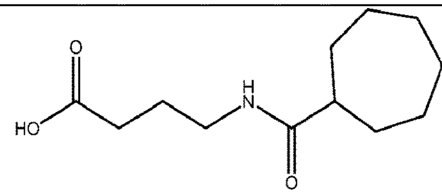 |
| III | 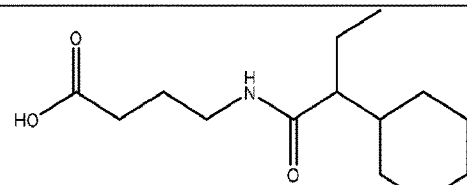 |
| IV | 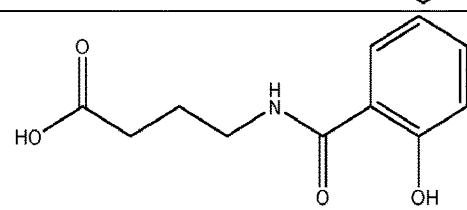 |
| V | 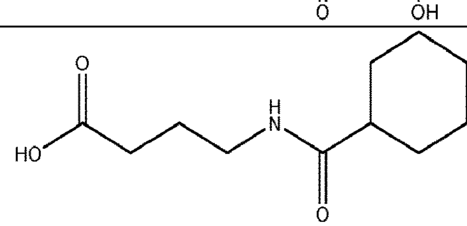 |
| VI | 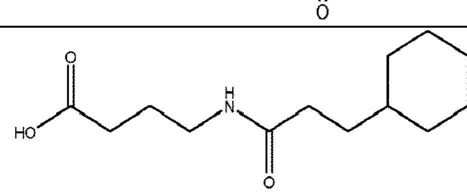 |
| VII | 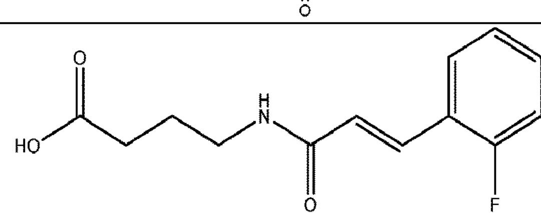 |
| VIII | 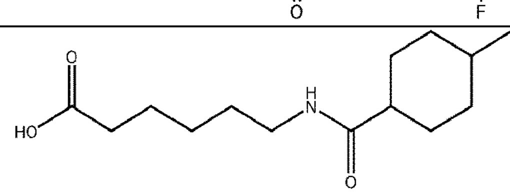 |
| IX | 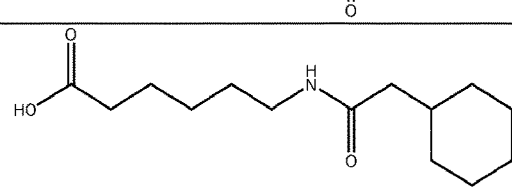 |

| # | Structure |
|---|---|
| X | 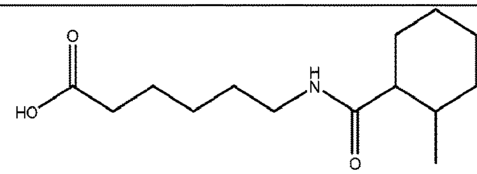 |
| XI | 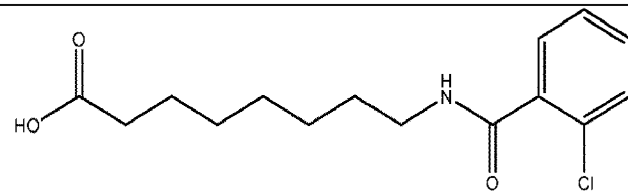 |
| XII | 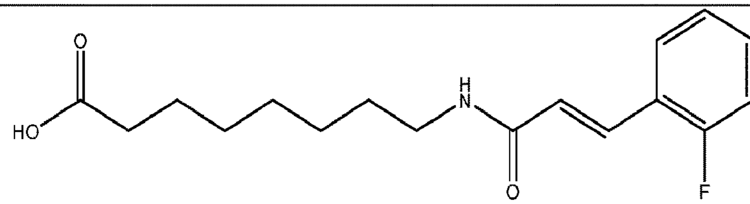 |
| XIII | 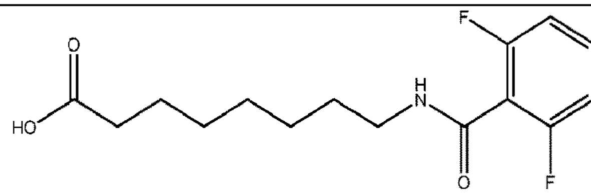 |
| XIV | 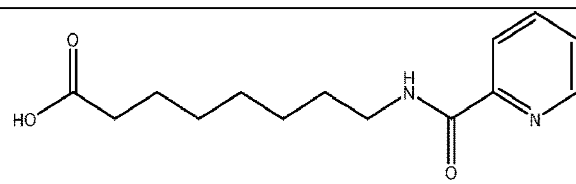 |
| XV | 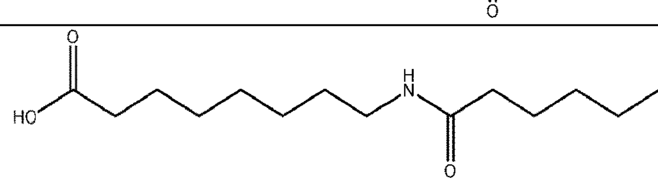 |
| XVI | 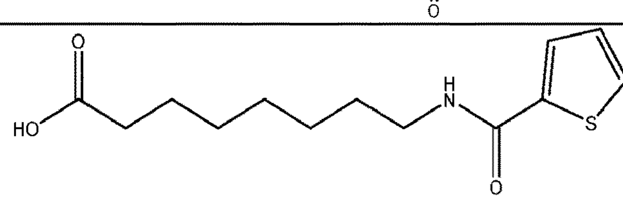 |
| XVII | 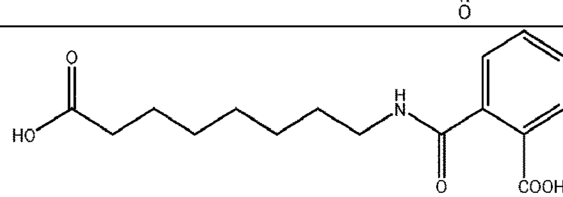 |
| XVIII | 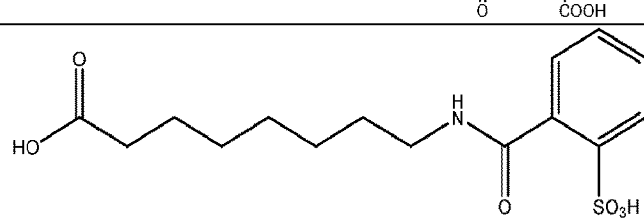 |

FIG. 3 cont'd

| # | Structure |
|---|---|
| XVIII | 8-[(2-sulfobenzoyl)amino]octanoic acid |
| XIX | 8-[(2-hydroxybenzoyl)amino]octanoic acid |
| XX | 8-[(2-fluorobenzoyl)amino]octanoic acid |
| XXI | 8-[[(E)-3-(2-hydroxyphenyl)prop-2-enoyl]amino]octanoic acid |
| XXII | 8-[(2,6-dihydroxybenzoyl)amino]octanoic acid |
| XXIII | 8-(cyclohexanecarbonylamino)octanoic acid |
| XXIV | 8-[(2-methylbenzoyl)amino]octanoic acid |
| XXV | 8-(1H-pyrrole-2-carbonylamino)octanoic acid |
| XXVI | 8-[[(1S,3R,4R,5R)-1,3,4,5-tetrahydroxycyclohexanecarbonyl]amino]octanoic acid |

| # | Structure |
|---|---|
| XXVII | 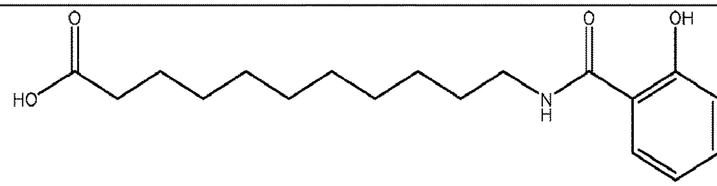 |
| XXVIII | 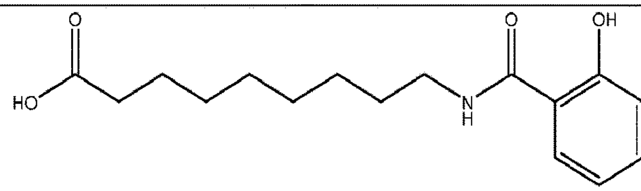 |
| XXIX | 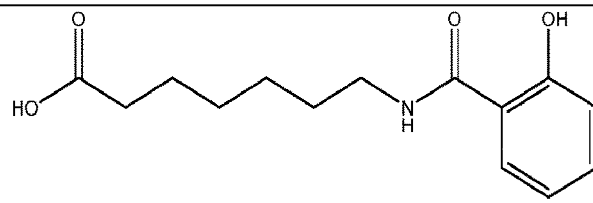 |
| XXX | 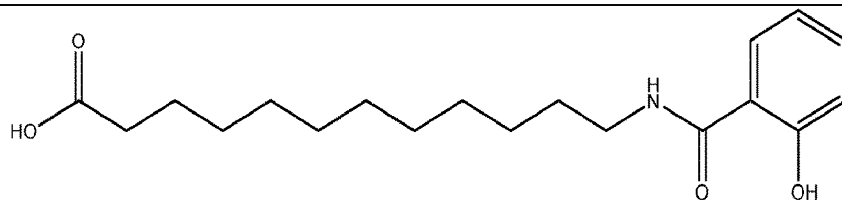 |
| XXXI | 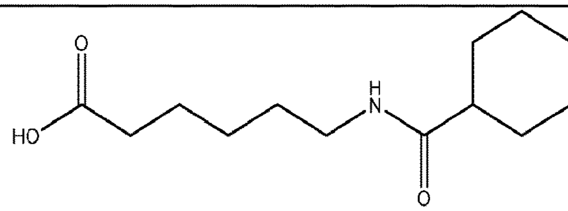 |
| XXXII | 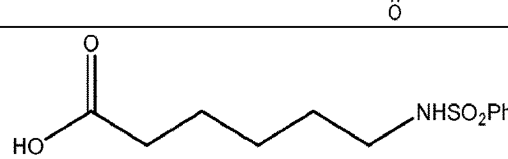 |
| XXXIII | 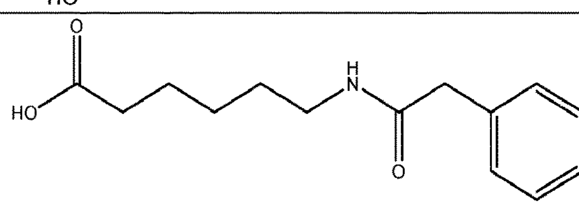 |
| XXXIV | 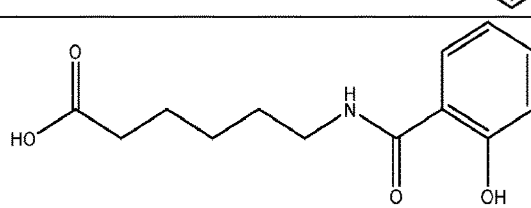 |
| XXXV | 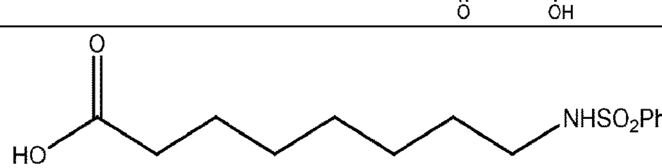 |

FIG. 4

| # | Structure | # | Structure |
|---|---|---|---|
| a | R₁-C(=O)-N(R₂)-CH(CH₃)-C(=O)-OR₃ | j | R₁-C(=O)-N(R₂)-CH(CH₂CH₂SCH₃)-C(=O)-OR₃ |
| b | R₁-C(=O)-N(R₂)-CH(CH₂C(=O)NH₂)-C(=O)-OR₃ | k | R₁-C(=O)-N(R₂)-CH(CH₂-C₆H₅)-C(=O)-OR₃ |
| c | R₁-C(=O)-N(R₂)-CH(CH₂COO⁻Na⁺)-C(=O)-OR₃ | l | R₁-C(=O)-N(pyrrolidine)-C(=O)-OR₃ (proline) |
| d | R₁-C(=O)-N(R₂)-CH(CH₂SH)-C(=O)-OR₃ | m | R₁-C(=O)-N(R₂)-CH(CH₂OR')-C(=O)-OR₃ |
| e | R₁-C(=O)-N(R₂)-CH(CH₂CH₂COO⁻Na⁺)-C(=O)-OR₃ | n | R₁-C(=O)-N(R₂)-CH(CH(CH₃)OR')-C(=O)-OR₃ |

| # | Structure | # | Structure |
|---|---|---|---|
| f | 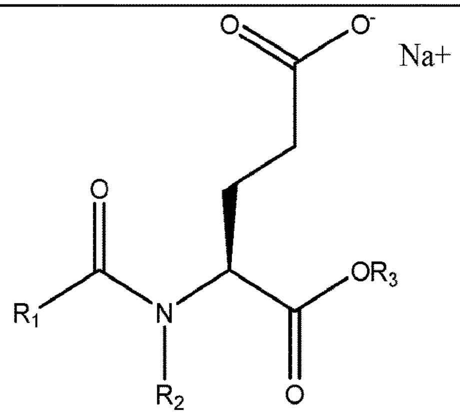 | o | 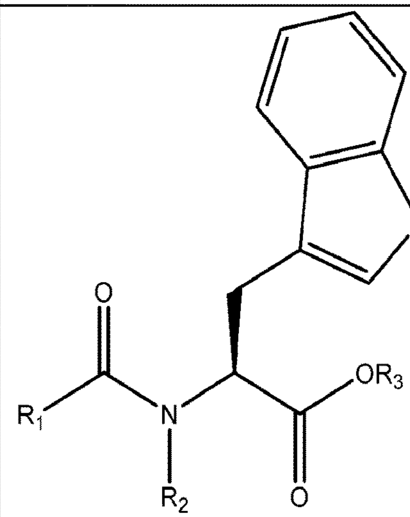 |
| g | 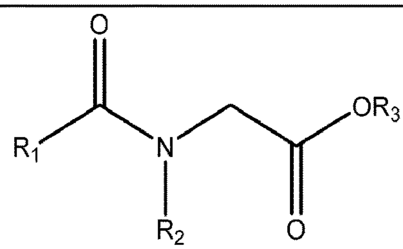 | p | 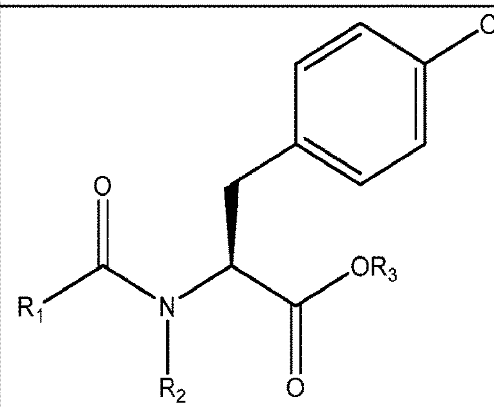 |
| h | 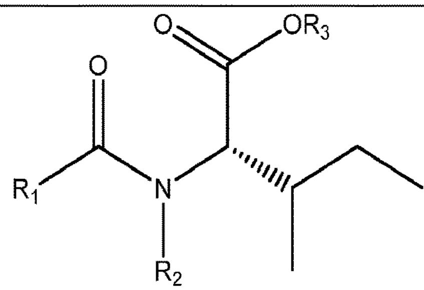 | q | 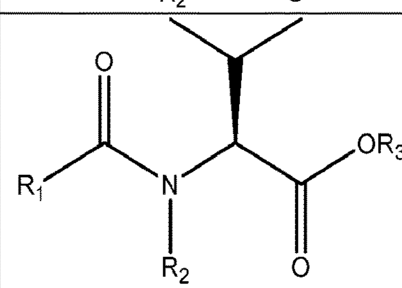 |
| i | 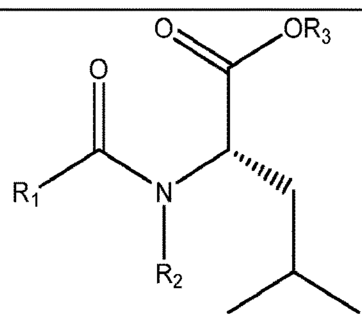 | r | 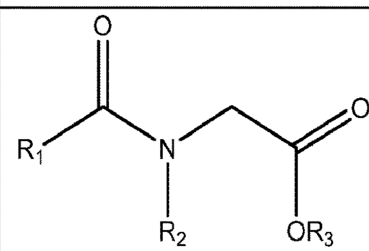 |

FIG. 9

| Dose THC/CBD (mg/kg) | Dose SNAC (mg/kg) | THC | | | | CBD | | | |
|---|---|---|---|---|---|---|---|---|---|
| | | $T_{max}$ (hr) | $C_{max}$ (ng/mL) | $AUC_{0-Tlast}$ (hr*ng/mL) | Compared to cannabis alone $C_{max}$ (AUC) | $T_{max}$ (hr) | $C_{max}$ (ng/mL) | $AUC_{0-Tlast}$ (hr*ng/mL) | Compared to cannabis alone $C_{max}$ (AUC) |
| 12.5/12.5 | 0 | 1.00 | 79.13 | 200.3 | NA | 1.00 | 11.23 | 17.29 | NA |
| 12.5/12.5 | 250 | 1.00 | 112.57 | 218.45 | 1.4 (1.1) | 0.50 | 32.9 | 16.11 | 2.9 (0.93) |
| 12.5/12.5 | 500 | 1.00 | 111.5 | 170.64 | 1.4 (0.85) | 1.00 | 31.7 | 13.17 | 2.8 (0.79) |
| 25/25 | 500 | 2.00 | 546.17 | 1256.49 | 6.9 (6.3) | 0.25 | 159.3 | 382.14 | 14.2 (22.1) |

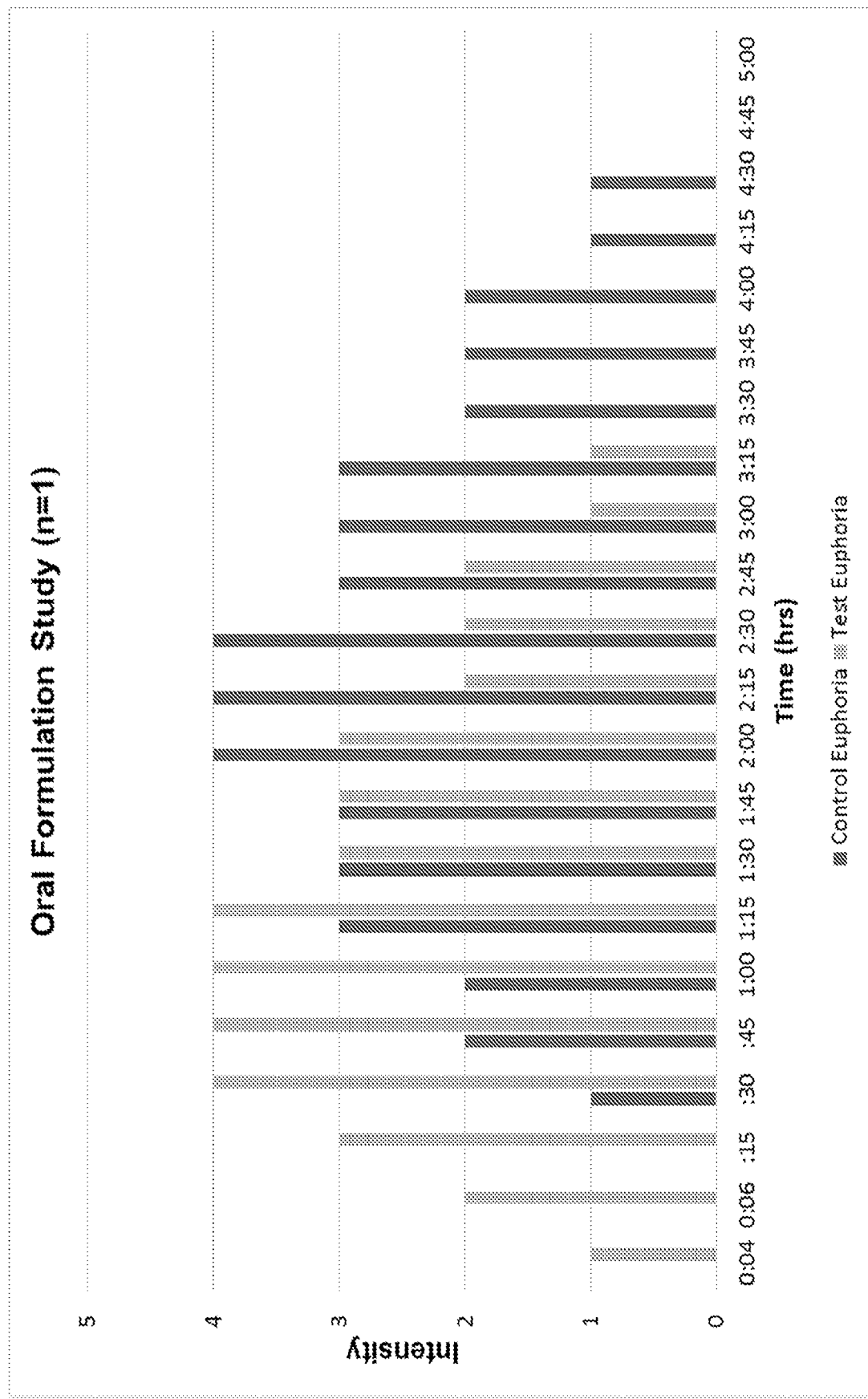

FAST-ACTING PLANT-BASED MEDICINAL COMPOUNDS AND NUTRITIONAL SUPPLEMENTS

CROSS REFERENCE TO RELATED APPLICATIONS

This Application is a national phase patent application based on International Patent Application No. PCT/US2017/055547, filed on Oct. 6, 2017, which claims priority to U.S. Provisional Patent Application No. 62/429,544 filed Dec. 2, 2016, the entire contents each of which is incorporated by reference herein.

FIELD OF THE DISCLOSURE

The current disclosure provides fast-acting plant-based medicinal compounds or nutritional supplements in various carrier combinations. The carriers can include N-acylated fatty amino acids, penetration enhancers, and/or various other beneficial carriers. The plant-based composition/carrier combinations can create administration benefits following oral administration.

BACKGROUND OF THE DISCLOSURE

Historically, the plant world has been the most important source of medicinal agents for the treatment of human and animal disease, and for use as preventative agents in maintaining good health. However, for at least the last 150 years, Western medicine has been dominated by synthetic chemical agents.

It is now being increasingly recognized, however, that many plants and plant extracts are highly effective agents for the prevention and treatment of disease. A single plant can possess a large number of pharmaceutically active agents, and extracts obtained therefrom can exert their activities on a variety of physiologic processes, increasing the range of the desired therapeutic effect.

As one example, U.S. Publication No. 2015/0050373 describes use of plants from the *Calophyllum* genus to treat metabolic disorders. *Calophyllum* is a flowering plant genus of around 180-200 species of tropical evergreen trees. The *Calophyllum* genus includes four subcategories: *Calophyllum brasiliense*, *Calophyllum caledonicurn*, *Calophyllum inophyllum* and *Calophyllum soulattri*. *Calophyllum inophyllum*, is a medium to large sized evergreen tree that averages 25-65 feet in height. Different medicinal uses of this plant have been reported in the literature, for example, decoction of the bark of this plant treats internal hemorrhages. The oil extracted from *Calophyllum inophyllum* seeds is used to treat rheumatoid arthritis or joint disorders; itching; eczema; pimples appearing on head; eye diseases; and kidney failure.

U.S. Publication No. 2014/0193345 describes use of the plants *Uncaria tomentosa, Thymus vulgaris, Matricaria recutita, Salix alba, Calendula officinalis, Usnea barbata, Ligusticum porterii-osha, Gaultheria procumbens, Camellia sinensis, Vaccinium myrtillus, Melissa officinalis, Allium sativum, Camellia sinensis* and *Krameria triandra* to treat mucosal lesions.

U.S. Publication No. 2010/0068297 describes use of the plants *Punica granatum, Viburnum plicatum, Camellia sinensis*, and *Acer* spp. as antimicrobials.

Numerous medical uses have also been identified for the *cannabis* plant. For example, delta-9-tetrahydrocannabinol (THC, also referred to as Dronabinol), an extract of the *cannabis* plant has been formulated in sesame oil for oral delivery. THC exhibits complex effects on the central nervous system (CNS), including central sympathomimetic activity. THC has been shown to have a marked appetite stimulant effect and has been used in the treatment of AIDS-related anorexia. THC demonstrates effects on appetite, mood, cognition, memory and perception. Furthermore, the drug has anti-emetic properties and is used to control nausea and vomiting associated with cancer chemotherapy. These effects appear to be dose related.

THC's efficacy in pain treatment has been described in Pharm. J. 259, 104, 1997 and in Pharm. Sci. 3, 546, 1997. Nabilone, a synthetic cannabinoid has also been reported to be an anti-emetic and anxiolytic, and also useful for treating pain of various etiologies such as multiple sclerosis (MS), peripheral neuropathy and spinal injuries (Lancet, 1995, 345, 579, Pharm. J. 259, 104, 1997; Baker & Pryce, Expert Opin Investig Drugs. 2003 April; 12(4):561-7)). THC has also been reported to be useful in the treatment of AIDS (J. Pain. Symptom Manage. 1995, 10, 89-97) when given orally.

Another cannabinoid with well-documented health benefits is cannabidiol (CBD). In contrast to THC, CBD does not exert psychoactive effects. CBD is reported to have antidepressant (Zanelati T, et al. Journal of Pharmacology. 2010. 159(1):122-8;), anti-anxiety (Resstel B M, et al. Br J Pharmacol. 2009. 156(1):181-188), anti-inflammatory (Vuolo F, et al. Mediators of Inflammation. 2015. 538670), and neuroprotective effects (Campos A C, et al. Pharmacol Res. 2016. 112:119-127).

Additional uses for the *cannabis* plant include treatment of addiction (De Vries, et al., Psychopharmacology (Berl). 2003 July; 168(1-2):164-9); ADHD (O'Connell and Ché, Harm Reduction Journal. 2007; 4:16); alcoholism (Basavarajappa & Hungund, Alcohol. 2005 January-February; 40(1):15-24); Alzheimer's disease (Eubanks et al., Mol Pharm. 2006 November-December; 3(6):773-7); amyotrophic lateral sclerosis (ALS) (Raman et al., Amyotroph Lateral Scler Other Motor Neuron Disord. 2004 March; 5(1):33-9); anxiety (The British Journal of Psychiatry February 2001, 178 (2) 107-115); asthma (Tashkin et al., American Review of Respiratory Disease, 1975; 112, 377); autoimmune diseases (Lyman et al., J Neuroimmunol. 1989 June; 23(1):73-81); bacterial infections (Nissen et al., Fitoterapia. 2010 July; 81(5):413-9); bone loss (Bab et al., Ann Med. 2009; 41(8):560-7); brain injury/stroke (Shohami et al., Br J Pharmacol. 2011 August; 163(7):1402-10); cancer (Guindon & Hohmann, Br J Pharmacol. 2011 August; 163 (7):1447-63); heart disease (Walsh et al., Br J Pharmacol. 2010 July; 160(5):1234-42); Huntington's disease (Lastres-Becker et al., J Neurochem. 2003 March; 84(5):1097-109); inflammation (AAPS J. 2009 March; 11(1): 109-119); Parkinson's disease (Sieradzan et al., Neurology. 2001 Dec. 11; 57(11):2108-11); and psoriasis (Trends Pharmacol Sci. 2009 August; 30(8): 411-420).

Additional documented uses for the *cannabis* plant include treating acquired hypothyroidism, acute gastritis, agoraphobia, ankyloses, arthritis, Asperger's syndrome, atherosclerosis, autism, bipolar disorder, blood disorders, cachexia, carpal tunnel syndrome, cerebral palsy, cervical disk disease, cervicobrachial syndrome, chronic fatigue syndrome, chronic pain, cluster headache, conjunctivitis, Crohn's disease, cystic fibrosis, depression, dermatitis, diabetes, dystonia, eating disorders, eczema, epilepsy, fever, fibromyalgia, flu, fungal infection, gastrointestinal disorders, glaucoma, glioma, Grave's disease, hepatitis, herpes, hypertension, impotence, incontinence, infant mortality, inflammatory bowel disease (IBD), insomnia, liver fibrosis, mad cow disease, menopause, migraine headaches, motion sickness, MRSA, muscular dystrophy, nail patella syndrome, neuroinflammation, nicotine addiction, obesity, obsessive compulsive disorder (OCD), pancreatitis, panic disorder, periodontal disease, phantom limb pain, poison ivy allergy, premenstrual syndrome (PMS), proximal myotonic myopathy, post-traumatic stress disorder (PTSD), Raynaud's disease, restless leg syndrome, schizophrenia, scleroderma, septic shock, shingles herpes zoster), sickle cell disease, seizures, sleep apnea, sleep disorders, stress, stuttering, temporomandibular joint disorder (TMJ), tension headaches, tinnitus, Tourette's syndrome, traumatic memories, wasting syndrome, and withdrawal.

Despite the numerous benefits associated with plant-based compounds and nutritional supplements, when administered in oral form, their onset of action is generally slow, which can detract from their usefulness in some instances. For example, after oral administration, THC has an onset of action of up to 1.5 hours and a peak effect at 2-4 hours. The duration of action is 4-6 hours, but the appetite stimulant effect may continue for 24 hours or longer after administration. THC is almost completely absorbed (90-95%) after single oral doses. However, due to a combined effect of first pass hepatic metabolism and poor aqueous solubility (THC water solubility is 2.8 mg/L), only 10-20% of the administered dose reaches the systemic circulation. Therefore, oral consumption of *cannabis* is characterized by low bioavailability of cannabinoids, and slow onset of action. Thus, as this one example provides, there is room for improvement in the oral administration of plant-based compounds and nutritional supplements.

SUMMARY OF THE DISCLOSURE

The current disclosure provides fast-acting plant-based medicinal compounds and nutritional supplements (collectively, plant-based compositions) formulated for oral delivery. By providing fast-acting delivery, physiological benefits are observed earlier increasing the usefulness of these compounds.

The disclosed fast-acting plant-based compositions can create various administration benefits in providing therapeutically effective amounts in a variety of conditions. Exemplary administration benefits include increased absorption, increased bioavailability, faster onset of action, higher peak concentrations, faster time to peak concentrations, increased subjective therapeutic efficacy, and increased objective therapeutic efficacy.

The fast-acting nature of the plant-based compositions is created by including one or more N-acylated fatty amino acids, absorption enhancing agents, and/or various other beneficial carriers, such as surfactants, detergents, azones, pyrrolidones, glycols and bile salts in an oral formulation. In particular embodiments, N-acylated fatty amino acids can be linear, branched, cyclic, bicyclic, or aromatic including, for example, 1-50 carbon atoms in an oral formulation. That use of N-acylated fatty amino acids could provide a fast-acting benefit with a plant-based composition was unexpected given particular aspects of plant-based components described further herein. For example, the ability of N-acylated fatty amino acids to increase absorption of compounds is proportional to the water-solubility of a compound. Many plant-based compounds are not water-soluble and would not have been expected to be affected by the presence of an N-acylated fatty amino acid.

In particular embodiments, the plant-based compositions include *Calophyllum brasiliense, Calophyllum caledonicurn, Calophyllum inophyllum, Calophyllum soulattri, Uncaria tomentosa, Thymus vulgaris, Matricaria recutita, Salix alba, Calendula officinalis, Usnea barbata, Ligusticum porterii-osha, Gaultheria procumbens, Camellia sinensis, Vaccinium myrtillus, Melissa officinalis, Allium sativum, Camellia sinensis, Krameria triandra, Punica granatum, Viburnum plicatum, Nicotiana tabacum, Duboisia hopwoodii, Asclepias syriaca, Curcuma longa, Cannabis sativa, Cannabis indica, Cannabis ruderalis*, and *Acer* spp., or an extract thereof. In particular embodiments, the plant-based compositions include the cannabis plant, or an extract thereof.

BRIEF DESCRIPTION OF THE FIGURES

FIG. 1A shows the multiple of improvement from SNAC plotted for cromolyn, vitamin B12, atorvastatin, and ibandronate, along with the aqueous solubility of each molecule. The plotted data shows a striking fit to a logarithmic trendline ($R^2$=0.998), indicating a logarithmic relationship between the aqueous solubility of each and the extent to which SNAC improves absorption. As the water solubility of the molecule increases, SNAC's ability to enhance its absorption also increases. FIG. 1B plots the aqueous solubility of heparin, acyclovir, rhGH, PTH, MT-II, GLP-1, calcitonin, yy peptide, and THC according to the logarithmic trendline derived from FIG. 1A.

FIG. 9 shows THC and CBD Cmax and AUC following a single oral administration to rats.

FIG. 11 shows intensity, duration and onset of action of orally administered cannabis/N-[8-(2-hydroxybenzoyl) amino] caprylic acid (NAC, "test") formulation and cannabis (without NAC, "control") formulation.

DETAILED DESCRIPTION

Figure 1A:
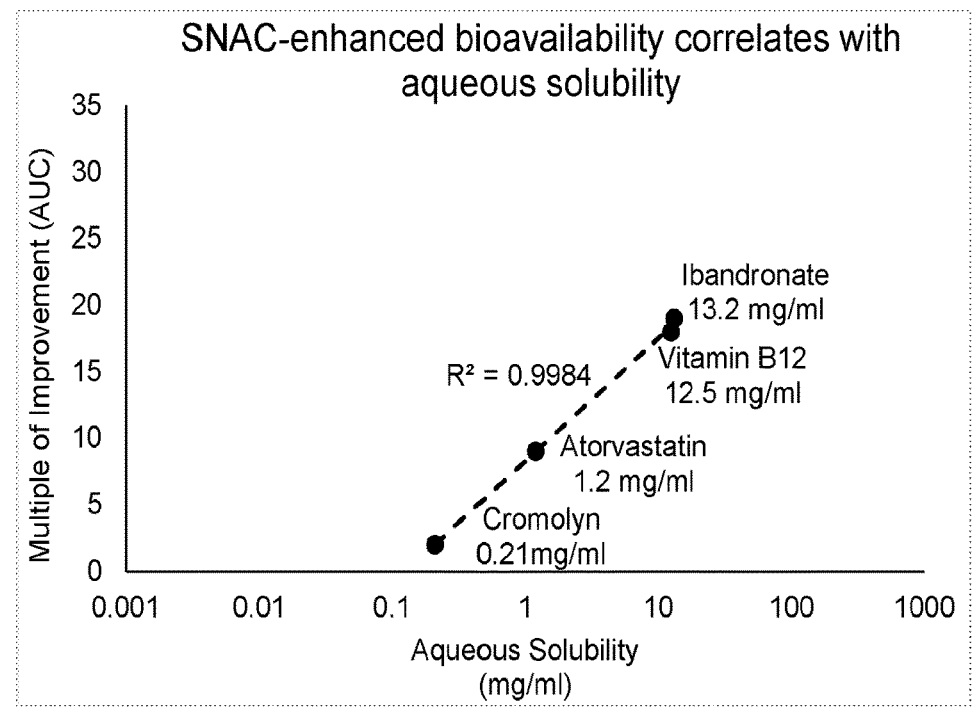
FIGS. 1A and 1B show an established correlation between water-solubility and the ability of SNAC to improve a molecule's absorption.

Despite the numerous benefits associated with plant-based compounds and nutritional supplements, when administered in oral form, their onset of action can be slow, which can detract from their usefulness in some instances. For example, after oral administration, THC has an onset of action of up to 1.5 hours and a peak effect at 2-4 hours. The duration of action for psychoactive effects is 4-6 hours, but the appetite stimulant effect may continue for 24 hours or longer after administration. THC is almost completely absorbed (90-95%) after single oral doses. However, due to a combined effect of first pass hepatic metabolism and poor aqueous solubility (THC water solubility is 2.8 mg/L) only 4-20% of the administered dose reaches the systemic circulation. Therefore, oral consumption of cannabis is characterized by low bioavailability of cannabinoids, and slow onset of action. Thus, as this one example provides, there is room for improvement in the oral administration of plant-based compounds and nutritional supplements.

The current disclosure provides fast-acting plant-based medicinal compounds and nutritional supplements (collectively, plant-based compositions) formulated for oral delivery. By providing fast-acting delivery, physiological benefits are observed earlier increasing the usefulness of these compounds.

The disclosed fast-acting plant-based compositions can create various administration benefits in providing therapeutically effective amounts in a variety of conditions. Exemplary administration benefits include increased absorption, increased bioavailability, faster onset of action, higher peak concentrations, faster time to peak concentrations, increased subjective therapeutic efficacy, and increased objective therapeutic efficacy.

The fast-acting nature of the plant-based compositions is created by including one or more N-acylated fatty amino acids, absorption enhancing agents, and/or various other beneficial carriers, such as surfactants, detergents, azones, pyrrolidones, glycols and bile salts in an oral formulation. In particular embodiments, N-acylated fatty amino acids can be linear, branched, cyclic, bicyclic, or aromatic including, for example, 1-50 carbon atoms in an oral formulation. That use of N-acylated fatty amino acids could provide a fast-acting benefit with a plant-based composition was unexpected given particular aspects of plant-based components described further herein. For example, the ability of N-acylated fatty amino acids to increase absorption of compounds is proportional to the water-solubility of a compound. Many plant-based compounds are not water-soluble and would not have been expected to be affected by the presence of an N-acylated fatty amino acid.

Molecules that have been shown to have improved absorption when co-administered with an N-acylated fatty amino acid (e.g., SNAC) include water-soluble molecules such as cromolyn, vitamin B12, atorvastatin, ibandronate, heparin, acyclovir, recombinant human growth hormone (rhGH), parathyroid hormone 1-34 (PTH 1-34), α-melanotropin (MT-II), GLP-1, calcitonin, and peptide yy.

FIG. 1A shows an established correlation between water-solubility and the ability of SNAC to improve a molecule's absorption. For cromolyn, vitamin B12, atorvastatin, and ibandronate, published results include area under the curve (AUC), which is calculated from a time-course of plasma levels. To quantify the effect of co-administration with SNAC, a multiple of improvement can be calculated by dividing the AUC for a molecule with SNAC by the AUC for the molecule without SNAC. FIG. 1A shows the multiple of improvement from SNAC plotted for cromolyn, vitamin B12, atorvastatin, and ibandronate, along with the aqueous solubility of each molecule. The plotted data shows a striking fit to a logarithmic trendline ($R^2$=0.998), indicating a logarithmic relationship between the aqueous solubility of each and the extent to which SNAC improves its absorption.

Figure 1B:
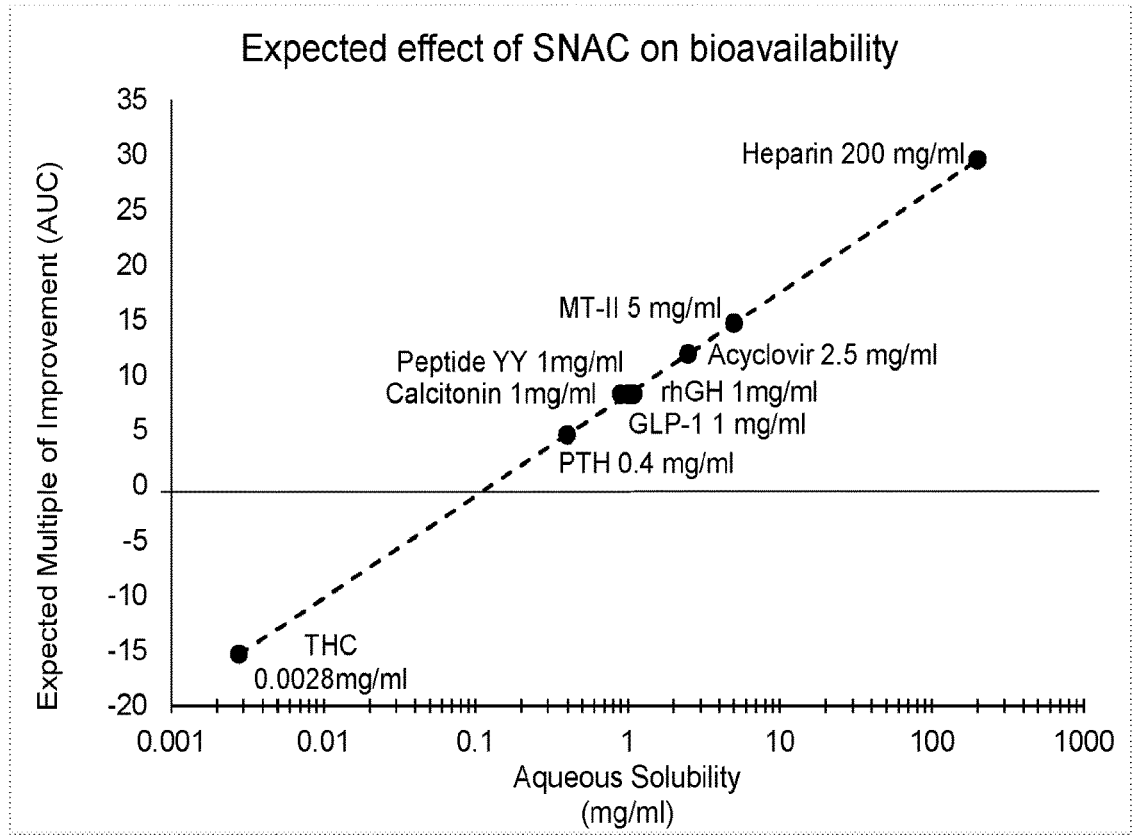

Heparin, acyclovir, rhGH, PTH, MT-II, GLP-1, calcitonin, and yy peptide are other molecules that have been shown to have SNAC-improved absorption, as demonstrated by Cmax (maximum drug plasma level) and/or Tmax (the time taken to reach maximum drug plasma level). As shown in FIG. 1B, each of these molecules has an aqueous solubility of more than 0.15 mg/ml, and therefore, the model accurately predicts that SNAC can improve their absorption. This result demonstrates that a SNAC-based absorption improvement correlates with a molecule's aqueous solubility. FIG. 1B further plots the aqueous solubility of THC (0.0028 mg/ml) to the logarithmic trendline and SNAC's predicted effect based on the same. Based at least on the foregoing, the results described herein were unexpected and would not have been reasonably expected by those of ordinary skill in the art.

Aspects of the disclosure are now described in more detail.

The current disclosure provides fast-acting plant-based compositions including vegetable matter and a carrier as an oral formulation. Plant-based compositions refer to plant-based medicinal compounds and plant-based nutritional supplements. Plant-based medicinal compounds provide therapeutically-effective amounts to treat a condition, such as those described in the Background of the Disclosure. Plant-based nutritional supplements claim a benefit related to a classical nutrient deficiency; describes how the supplement is intended to affect the structure or function of the human body; characterizes a documented mechanism by which the supplement acts to maintain such structure or function; and/or describes general well-being associated with consumption of the product. In particular embodiments, a nutritional supplement may not claim to diagnose, mitigate, treat, cure, or prevent a specific disease or class of diseases.

Plant-based compositions include vegetable matter. Vegetable matter is matter produced by a plant and includes any whole plant or plant part (e.g., bark, wood, leaves, stems, roots, flowers, fruits, seeds, or parts thereof) and/or exudates or extracts thereof. In particular embodiments, plant-based compositions include botanical products. Botanical products can include plant materials, algae, macroscopic fungi, and/or combinations thereof. In particular embodiments, plant-based compositions include a mixture of various types of vegetable matter. Plant-based compositions can also include materials derived from vegetable matter including resins, oils, dried flowers, kief, tinctures, infusions, etc. In particular embodiments, the vegetable matter has little or no water solubility. In particular embodiments, plant-based compositions do not include synthetic, semi-synthetic, or chemically-modified drugs.

In particular embodiments, the plant-based compositions include vegetable matter derived from *Calophyllum brasiliense, Calophyllum caledonicurn, Calophyllum inophyllum, Calophyllum soulattri, Uncaria tomentosa, Thymus vulgaris, Matricaria recutita, Salix alba, Calendula officinalis, Usnea barbata, Ligusticum porterii-osha, Gaultheria procumbens, Camellia sinensis, Vaccinium myrtillus, Melissa officinalis, Allium sativum, Camellia sinensis, Krameria triandra, Punica granatum, Viburnum plicatum, Nicotiana tabacum, Duboisia hopwoodii, Asclepias syriaca, Curcuma longa, Cannabis sativa, Cannabis indica, Cannabis ruderalis* and/or *Acer* spp. or an extract thereof.

In particular embodiments, the plant-based compositions include vegetable matter derived from the cannabis plant.

The cannabis plant refers to a flowering plant including the species (or sub-species) *Cannabis sativa, Cannabis ruderalis,* and *Cannabis indica.*

Figure 2:
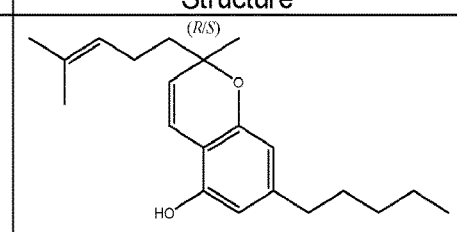
FIG. 2 provides exemplary cannabinoid structures.
Figure 2:
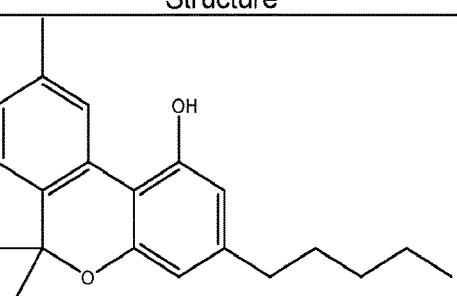
Figure 2:
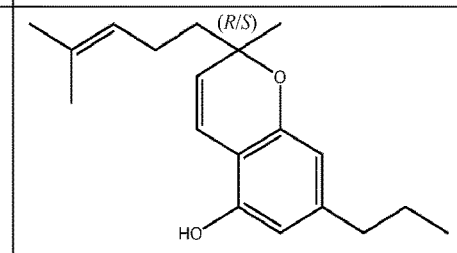
Figure 2:
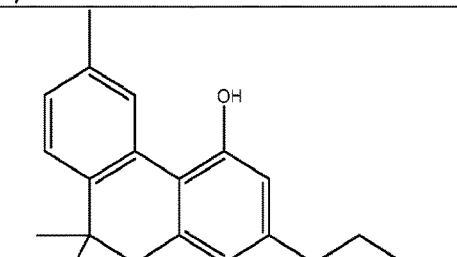
Figure 2:
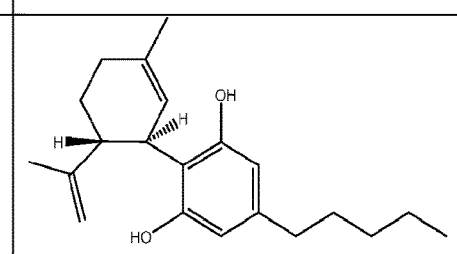
Figure 2:
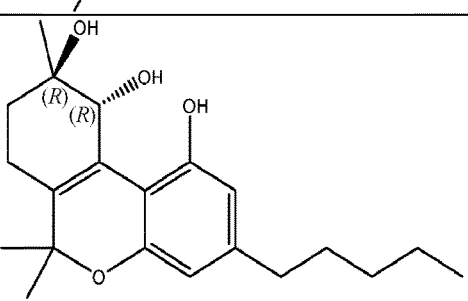
Figure 2:
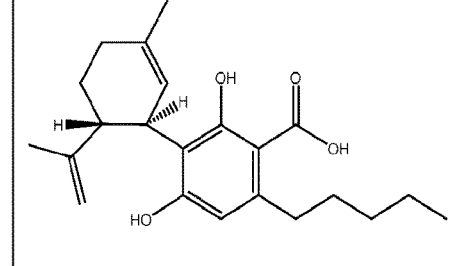
Figure 2:
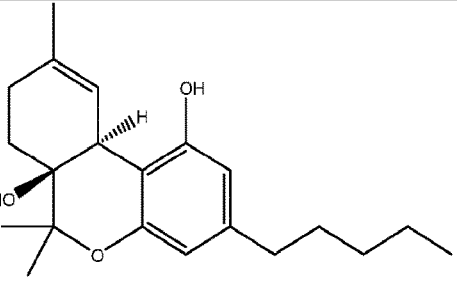

Particular extracts of the cannabis plant include cannabinoids. Cannabinoids are a group of cyclic molecules from cannabis plants that activate cannabinoid receptors (i.e., CB1 and CB2) in cells. There are at least 85 different cannabinoids that can be isolated from cannabis. Many cannabinoids produced by cannabis plants, such as Δ9-Tetrahydrocannabinol (THC) and cannabidiol (CBD), have very low or no solubility in water. The most notable cannabinoids are THC and CBD. Additional examples include cannabigerol (CBG), cannabichromene (CBC), cannabinol (CBN), cannabinodiol (CBDL), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), cannabinerolic acid, cannabidiolic acid (CBDA), Cannabinol propyl variant (CBNV), cannabitriol (CBO), tetrahydrocannabinolic acid (THCA), and tetrahydrocannabivarinic acid (THCVA). See, for example, FIG. 2. Extracts of the cannabis plant similarly include flavonoid compounds, terpenes, terpenoid, and synthetic, semisynthetic or highly purified versions of any such constituent.

Components of plant-based compositions can be produced by, e.g., pulverization, decoction, expression, and extraction of a starting plant product. The term "extract" can include all of the many types of preparations containing some or all of the active ingredients found in the relevant plants. Extracts may be produced by cold extraction techniques using a variety of different extraction solvents including water, fatty solvents (such as olive oil), and alcoholic solvents (e.g. 70% ethanol). Cold extraction techniques are typically applied to softer parts of the plant such as leaves and flowers, or in cases wherein the desired active components of the plant are heat labile. Alternatively, the aforementioned solvents may be used to produce extracts of the desired plants by a hot extraction technique, wherein said solvents are heated to a high temperature, the precise value of said temperature being dependent on the properties of the chosen solvent, and maintained at that temperature throughout the extraction process. Hot extraction techniques are more commonly applied to the harder, tougher parts of the plant, such as bark, woody branches and larger roots. In some cases, sequential extractions can be performed in more than one solvent, and at different temperatures. The plant extract may be used in a concentrated form. Alternatively, the extract may be diluted as appropriate to its intended use.

WO2004/026857 provides a method for preparing a purified cannabis extract, wherein the cannabinoids are purified to at least 99% wt % THC (Δ9-tetrahydrocannabinol). In this method a crude ethanolic extract of Cannabis plant material is passed through a column of activated charcoal and evaporated by means of rotary evaporation. The resulting THC enriched extract is subsequently passed through a column packed with Sephadex LH20 and eluted with chloroform/dichloromethane. The solvent used is removed by means of rotary evaporation. In order to further increase the purity of the THC enriched extract, the extract is dissolved in methanol and subsequently in pentane and subjected to rotary evaporation twice.

US2015/0126754 describes a) providing a crude solvent extract of Cannabis plant material; b) subjecting the crude extract to thin film evaporation to obtain a refined extract; c) chromatographically fractionating the refined extract to produce one or more high purity fractions having a THC content higher than a preset value and one or more low purity fractions having a THC content lower than the preset value, wherein the preset value is in the range of 95-99% by weight of dry matter; d) subjecting the one or more high purity fractions to another thin film evaporation; and e) collecting a THC isolate containing at least 97% THC by weight of dry matter; and wherein in step b) and/or in step d) the thin film evaporation is carried out by using wiped film evaporation. This method offers the advantage that it yields a high purity THC extract in good yield and without using solvents that pose a health risk. The method further offers the advantage that it is highly reproducible in that it produces THC-isolate with a specific cannabinoid profile. More particularly, the method yields a THC isolate that contains at least 97.0-99.5% THC and 0.4-2.0% of other cannabinoids, including at least 0.3% Cannabinol and Cannabidiol (all percentages by weight of dry matter).

Additional procedures for producing plant extracts (including hot extraction, cold extraction and other techniques) are described in publications including "Medicinal plants: a field guide to the medicinal plants of the Land of Israel (in Hebrew), author: N. Krispil, Har Gilo, Israel, 1986" and "Making plant medicine, author: R. Cech, pub. by Horizon Herbs, 2000".

In particular embodiments, plant components of plant-based compositions (e.g., plant extracts) may be sterilized, for example by autoclaving, and then allowed to cool and stored at an appropriate temperature (e.g., −20° C.). In particular embodiments, further purification to a molecular weight cut-off (e.g., below 10,000 Da) can be carried out, for example, by membrane ultrafiltration before storage.

In particular embodiments, plant-based compositions include carriers such as modified amino acids, a surfactant, a detergent, an azone, a pyrrolidone, a glycol, or a bile salt. An amino acid is any carboxylic acid having at least one free amine group and includes naturally occurring, non-naturally occurring and synthetic amino acids. Poly amino acids are either peptides or two or more amino acids linked by a bond formed by other groups which can be linked, e.g. an ester, anhydride, or an anhydride linkage. Peptides are two or more amino acids joined by a peptide bond. Peptides can vary in length from dipeptides with two amino acids to poly peptides with several hundred amino acids. See Chambers Biological Dictionary, editor Peter M. B. Walker, Cambridge, England: Chambers Cambridge, 1989, page 215. Di-peptides, tri-peptides, tetra-peptides, and penta-peptides can also be used.

Carriers which are modified amino acids include acylated fatty acid amino acids (FA-aa) or a salt thereof, which are typically prepared by modifying the amino acid or an ester thereof by acylation or sulfonation. Acylated fatty acid amino acids include N-acylated FA-aa or an amino acid acylated at its alpha amino group with a fatty acid.

Exemplary N-acylated fatty amino acid salts include sodium N-[8-(2-hydroxybenzoyl) amino] caprylate (SNAC). Other names for SNAC include Sodium-N-salicyloyl-8-aminocaprylate, Monosodium 8-(N-salicyloylamino) octanoate, N-(salicyloyl)-8-aminooctanoic acid monosodium salt, monosodium N-{8-(2-hydroxybenzoyl) amino}octanoate, or sodium 8-[(2-hydroxybenzoyl)amino] octanoate. SNAC has the structure:

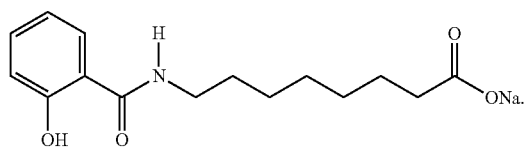

Salts of SNAC may also be used as a carrier.

In particular embodiments, the carriers include:

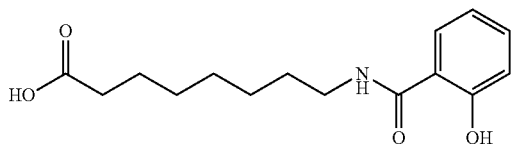 [SMILES: O=C(O)CCCCCCCNC(=O)c1ccccc1O]

In particular embodiments, the carriers include N-[8-(2-hydroxybenzoyl) amino] caprylic acid (NAC).

Other forms of carriers include:

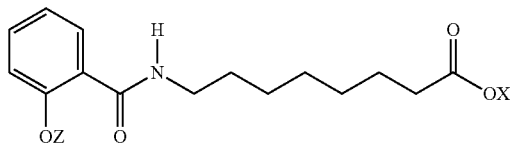

wherein X and Z are independently H, a monovalent cation, a divalent metal cation, or an organic cation. Examples of monovalent cations include sodium and potassium. Examples of divalent cations include calcium and magnesium. Examples of organic cations include ammonium and tetramethylammonium.

Figure 3:
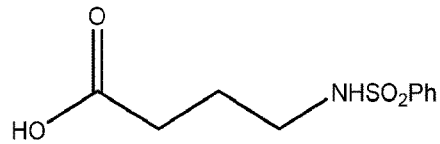
FIG. 3 provides modified amino acids of compounds I-XXXV.
Figure 3:
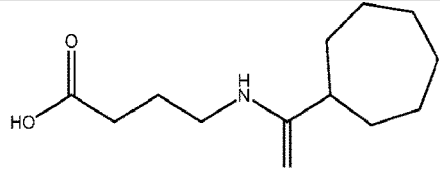
Figure 3:
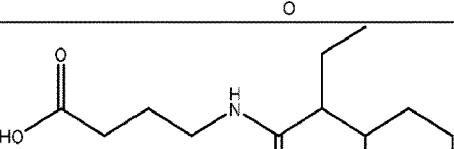
Figure 3:
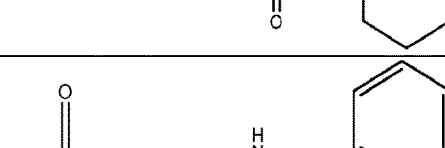
Figure 3:
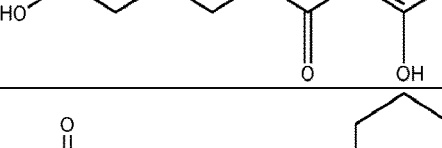
Figure 3:
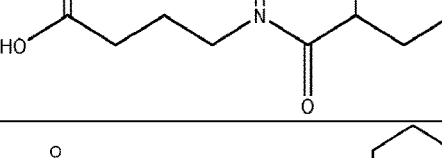
Figure 3:
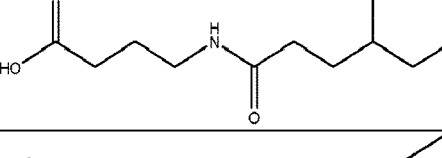
Figure 3:
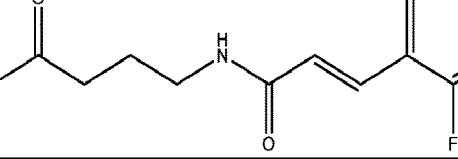
Figure 3:
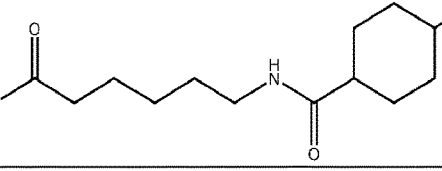
Figure 3:
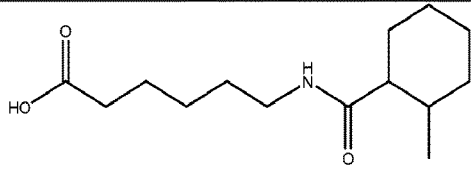
Figure 3:
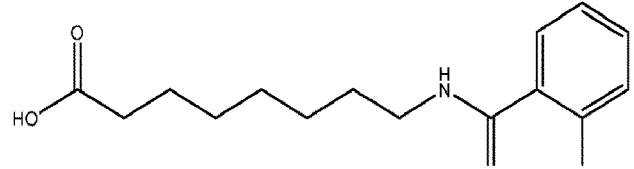
Figure 3:
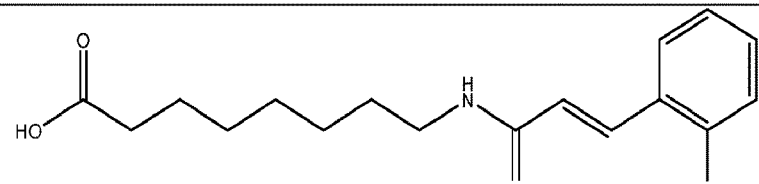
Figure 3:
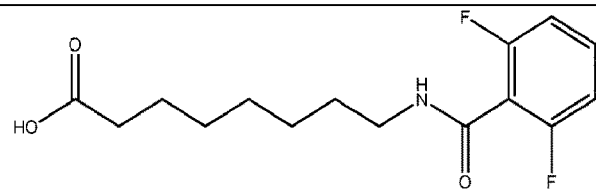
Figure 3:
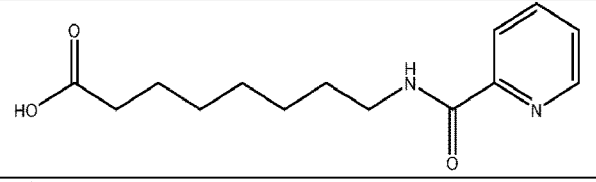
Figure 3:
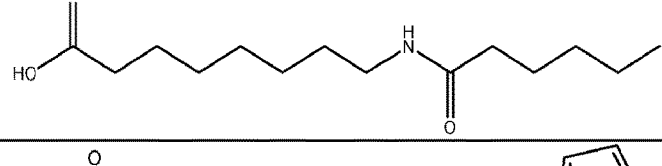
Figure 3:
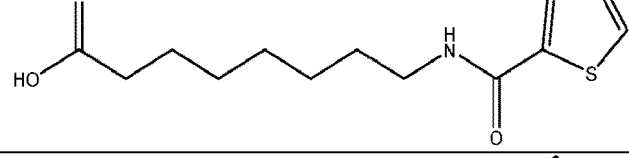
Figure 3:
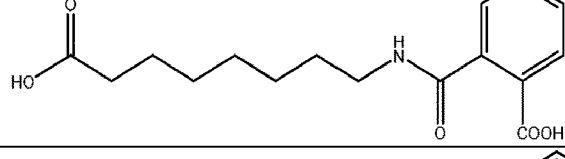
Figure 3:
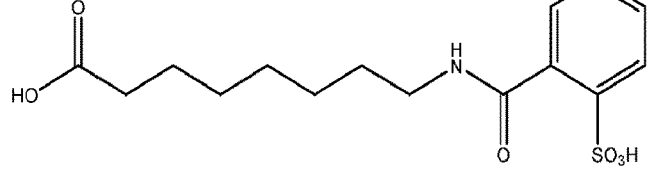
Figure 3:
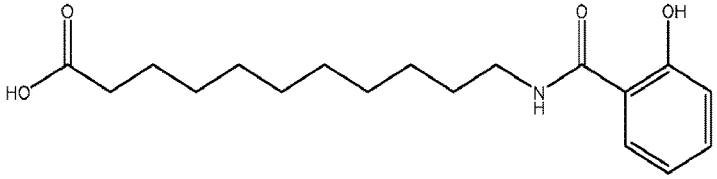
Figure 3:
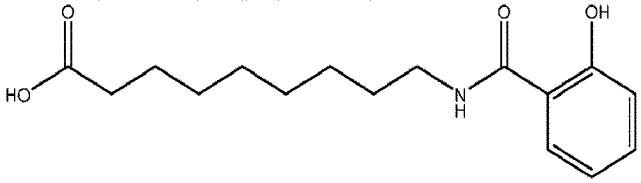
Figure 3:
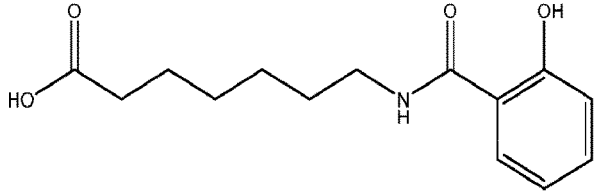
Figure 3:
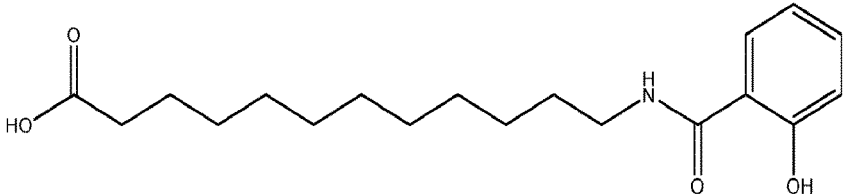
Figure 3:
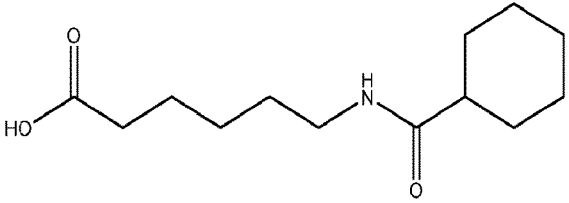
Figure 3:
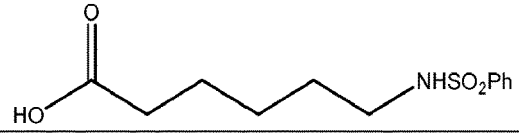
Figure 3:
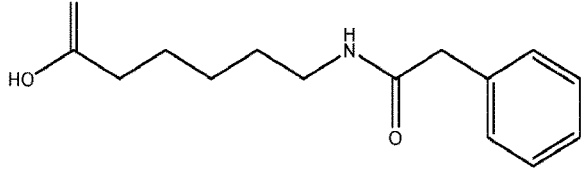
Figure 3:
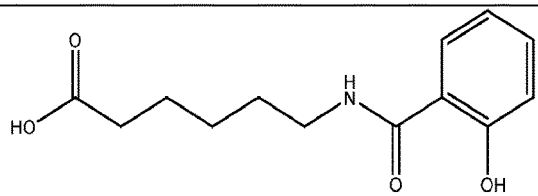
Figure 3:
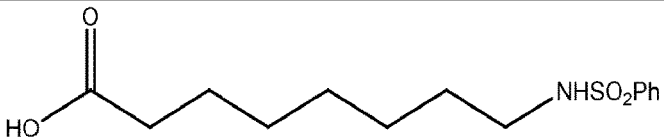

Exemplary modified amino acids, such as N-acylated FA-aas, are provided as compounds I-XXXV (see FIG. 3). Salts of these compounds and other N-acylated FA-aa can also be used as carriers.

Many of the compounds can be readily prepared from amino acids by methods within the skill of those in the art based upon the present disclosure. For example, compounds I-VII are derived from aminobutyric acid. Compounds VIII-X and XXXI-XXIIV are derived from aminocaproic acid. Compounds XI-XXVI and XXXV are derived from aminocaprylic acid. For example, the modified amino acid compounds above may be prepared by reacting the single amino acid with the appropriate modifying agent which reacts with free amino moiety present in the amino acids to form amides. Protecting groups may be used to avoid unwanted side reactions as would be known to those skilled in the art.

The amino acid can be dissolved in aqueous alkaline solution of a metal hydroxide, e.g., sodium or potassium hydroxide, and heated at a temperature ranging between 5° C. and 70° C., preferably between 10° C. and 40° C., for a period ranging between 1 hour and 4 hours, preferably 2.5 hours. The amount of alkali employed per equivalent of $NH_2$ groups in the amino acid generally ranges between 1.25 and 3 mmole, preferably between 1.5 and 2.25 mmole per equivalent of $NH_2$. The pH of the solution generally ranges between 8 and 13, preferably ranging between 10 and 12.

Thereafter, the appropriate amino acid modifying agent is added to the amino acid solution while stirring. The temperature of the mixture is maintained at a temperature generally ranging between 5° C. and 70° C., preferably between 10° C. and 40° C., for a period ranging between 1 and 4 hours. The amount of amino acid modifying agent employed in relation to the quantity of amino acid is based on the moles of total free $NH_2$ in the amino acid. In general, the amino acid modifying agent is employed in an amount ranging between 0.5 and 2.5 mole equivalents, preferably between 0.75 and 1.25 equivalents, per molar equivalent of total $NH_2$ group in the amino acid.

The reaction is quenched by adjusting the pH of the mixture with a suitable acid, e.g., concentrated hydrochloric acid, until the pH reaches between 2 and 3. The mixture separates on standing at room temperature to form a transparent upper layer and a white or off-white precipitate. The upper layer is discarded, and the modified amino acid is collected from the lower layer by filtration or decantation. The crude modified amino acid is then dissolved in water at a pH ranging between 9 and 13, preferably between 11 and 13. Insoluble materials are removed by filtration and the filtrate is dried in vacuo. The yield of modified amino acid generally ranges between 30 and 60%, and usually 45%.

If desired, amino acid esters, such as, for example benzyl, methyl, or ethyl esters of amino acid compounds, may be used to prepare the modified amino acids. The amino acid ester, dissolved in a suitable organic solvent such as dimethylformamide, pyridine, or tetrahydrofuran can be reacted with the appropriate amino acid modifying agent at a temperature ranging between 5° C. and 70° C., preferably 25° C., for a period ranging between 7 and 24 hours. The amount of amino acid modifying agent used relative to the amino acid ester is the same as described above for amino acids. This reaction may be carried out with or without a base such as, for example, triethylamine or diisopropylethylamine.

Thereafter, the reaction solvent is removed under negative pressure and the ester functionality is removed by hydrolyzing the modified amino acid ester with a suitable alkaline solution, e.g. 1N sodium hydroxide, at a temperature ranging between 50° C. and 80° C., preferably 70° C., for a period of time sufficient to hydrolyze off the ester group and form the modified amino acid having a free carboxyl group. The hydrolysis mixture is then cooled to room temperature and acidified, e.g. aqueous 25% hydrochloric acid solution, to a pH ranging between 2 and 2.5. The modified amino acid precipitates out of solution and is recovered by conventional means such as filtration or decantation. Benzyl esters may be removed by hydrogenation in an organic solvent using a transition metal catalyst.

The modified amino acid may be purified by recrystallization or by fractionation on solid column supports. Suitable recrystallization solvent systems include acetonitrile, methanol and tetrahydrofuran. Fractionation may be performed on a suitable solid column supports such as alumina, using methanol/n-propanol mixtures as the mobile phase; reverse phase column supports using trifluoroacetic acid/acetonitrile mixtures as the mobile phase; and ion exchange chromatography using water as the mobile phase. When anion exchange chromatography is performed, preferably a subsequent 0-500 mM sodium chloride gradient is employed.

In particular embodiments, modified amino acids having the formula

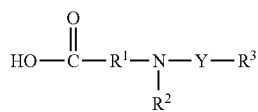

wherein Y is

or $SO_2$;
$R^1$ is $C_3$-$C_{24}$ alkylene, $C_2$-$C_{20}$ alkenylene, $C_2$-$C_{20}$ alkynylene, cycloalkylene, or an aromatic, such as arylene;
$R^2$ is hydrogen, $C_1$-$C_4$ alkyl, or $C_2$-$C_4$ alkenyl; and
$R^3$ is $C_1$-$C_7$ alkyl, $C_3$-$C_{10}$ cycloalkyl, aryl, thienyl, pyrrolo, or pyridyl, and
$R^3$ is optionally substituted by one or more $C_1$-$C_5$ alkyl group, $C_2$-$C_4$ alkenyl group, F, Cl, OH, $OR^1$, $SO_2$, COOH, $COOR^1$ or, $SO_3H$; may be prepared by
reacting in water and the presence of a base a lactam having the formula

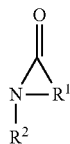

with a compound having the formula $R^3$—Y—X, wherein Y, $R^1$, $R^2$, and $R^3$ are as above and X is a leaving group. A lactam as shown in the above formula can be prepared, for example by the method described in Olah et al., Synthesis, 537-538 (1979).

In particular embodiments, modified amino acids also include an amino acid acylated at its alpha amino group with a fatty acid, which can be represented by the general formula A-X, wherein A is the alpha-amino acid residue and X is a fatty acid attached by acylation to A's alpha-amino group. The amino acids include cationic and non-cationic amino acids. In particular embodiments the term "non-cationic amino acid" refers to an amino acid selected from the group consisting of non-polar hydrophobic amino acids, polar non-charged amino acids, and polar acidic amino acids. In particular embodiments the term "non-cationic amino acid" as used herein refers to amino acids selected from the group consisting of Alanine (Ala), Valine (Val), Leucine (Leu), Isoleucine (Ile), Phenylalanine (Phe), Tryptophan (Trp), Methionine (Met), Proline (Pro), Sarcosine, Glycine (Gly), Serine (Ser), Threonine (Thr), Cysteine (Cys), Tyrosine (Tyr), Asparagine (Asn), and Glutamine (Gln), Aspartic acid (Asp), and Glutamic acid (Glu).

In particular embodiments, the acylated FA-aa includes an alpha amino acid residue of a non-polar hydrophobic amino acid. In particular embodiments, the acylated FA-aa may be represented by the general formula A-X, wherein A is the amino acid residue of a non-polar hydrophobic amino acid and X is a fatty acid attached by acylation to A's alpha-amino group. In particular embodiments the term "non-polar hydrophobic amino acid" as used herein refers to categorisation of amino acids used by the person skilled in the art. In particular embodiments the term "non-polar hydrophobic amino acid" refers to an amino acid selected from the group consisting of Ala, Val, Leu, Ile, Phe, Trp, Met, Pro and Sarcosine.

In particular embodiments, the acylated FA-aa includes the amino acid residue of a polar non-charged amino acid. In particular embodiments the acylated FA-aa may be represented by the general formula A-X, wherein A is the amino acid residue of a polar non-charged amino acid and X is a fatty acid attached by acylation to A's alpha-amino group. In particular embodiments the term "polar non-charged amino acid" as used herein refers to categorisation of amino acids used by the person skilled in the art. In particular embodiments the term "polar non-charged amino acid" refers to an amino acid selected from the group consisting of Gly, Ser, Thr, Cys, Tyr, Asn, and Gln.

In particular embodiments, the acylated FA-aa includes the amino acid residue of a polar acidic amino acid. In particular embodiments, the acylated FA-aa may be represented by the general formula A-X, wherein A is the amino acid residue of a polar acidic amino acid and X is a fatty acid attached by acylation to A's alpha-amino group. In particular embodiments, the term "polar acidic amino acid" as used herein refers to categorisation of amino acids used by the person skilled in the art. In particular embodiments, the term "polar acidic amino acid" refers to an amino acid selected from the group consisting of Asp and Glu.

In particular embodiments, the amino acid residue of the acylated FA-aa includes the amino acid residue of an amino acid that is not encoded by the genetic code. Modifications of amino acids by acylation may be readily performed using acylation agents known in the art that react with the free alpha-amino group of the amino acid.

In particular embodiments, the alpha-amino acids or the alpha-amino acid residues herein are in the L-form unless otherwise stated.

In particular embodiments, the amino acid residue is in the free acid form and/or a salt thereof, such as a sodium (Na+) salt thereof.

Exemplary embodiments of acylated FA-aas may be represented by the general Fa-aa formula I:

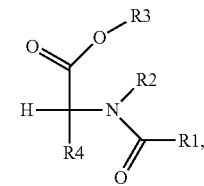

wherein R1 is an alkyl or aryl group including 5 to 19 carbon atoms; R2 is H (i.e. hydrogen), $CH_3$ (i.e. methyl group), or covalently attached to R4 via a $(CH_2)_3$ group; R3 is H or absent; and R4 is an amino acid side chain or covalently attached to R2 via a $(CH_2)_3$ group; or a salt thereof.

The FA-aa can be acylated with a fatty acid including a substituted or unsubstituted alkyl group consisting of 5 to 19 carbon atoms. In particular embodiments, the alkyl group consists of 5 to 17 carbon atoms. In particular embodiments, the alkyl group consists of 5-15 carbon atoms. In particular embodiments the alkyl group consists of 5-13 carbon atoms. In particular embodiments the alkyl group consists of 6 carbon atoms.

In particular embodiments, the acylated FA-aa is soluble at intestinal pH values, particularly in the range pH 5.5 to 8.0, such as in the range pH 6.5 to 7.0. In particular embodiments, the acylated FA-aa is soluble below pH 9.0.

In particular embodiments, the acylated FA-aa has a solubility of at least 5 mg/mL. In particular embodiments, the acylated FA-aa has a solubility of at least 10 mg/mL. In particular embodiments, the acylated FA-aa has a solubility of at least 20 mg/mL. In particular embodiments, the acylated FA-aa has a solubility of at least 30 mg/mL. In particular embodiments, the acylated FA-aa has a solubility of at least 40 mg/mL. In particular embodiments, the acylated FA-aa has a solubility of at least 50 mg/mL. In particular embodiments, the acylated FA-aa has a solubility of at least 60 mg/mL. In particular embodiments, the acylated FA-aa has a solubility of at least 70 mg/mL. In particular embodiments, the acylated FA-aa has a solubility of at least 80 mg/mL. In particular embodiments, the acylated FA-aa has a solubility of at least 90 mg/mL. In particular embodiments, the acylated FA-aa has a solubility of at least 100 mg/mL. In particular embodiments, solubility of the acylated FA-aa is determined in an aqueous solution at a pH value 1 unit above or below pKa of the FA-aa at 37° C. In particular embodiments, solubility of the acylated FA-aa is determined in an aqueous solution at pH 8 at 37° C. In particular embodiments, solubility of the acylated FA-aa is determined in an aqueous solution at a pH value 1 unit above or below pI of the FA-aa at 37° C. In particular embodiments, solubility of the acylated FA-aa is determined in an aqueous solution at a pH value 1 units above or below pI of the FA-aa at 37° C., wherein said FA-aa two or more ionisable groups with opposite charges. In particular embodiments, solubility of the FA-aa is determined in an aqueous 50 mM sodium phosphate buffer, pH 8.0 at 37° C.

Figure 4:
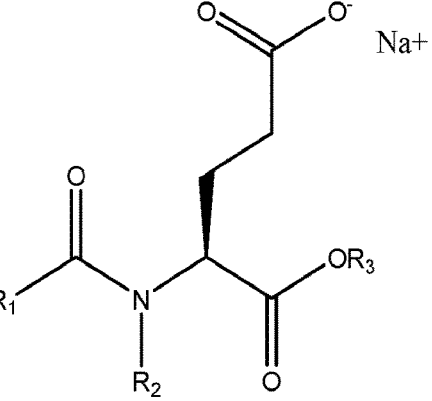
FIG. 4 provides fatty acid amino acids of formula (a), (b), (c), (d), (e), (f), (g), (h), (i), (j), (k), (l), (m), (n), (o), (p), (q), and (r), wherein R1 is an alkyl group including 5 to 19 carbon atoms, R2 is H (i.e. hydrogen) or CH3 (i.e. methyl group), and R3 is H; or a salt or the free acid form thereof.
Figure 4:
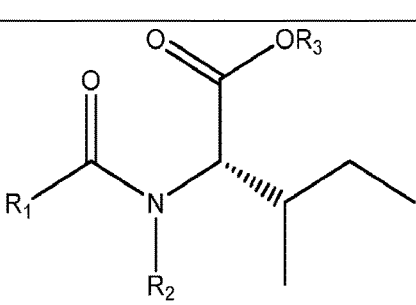
Figure 4:
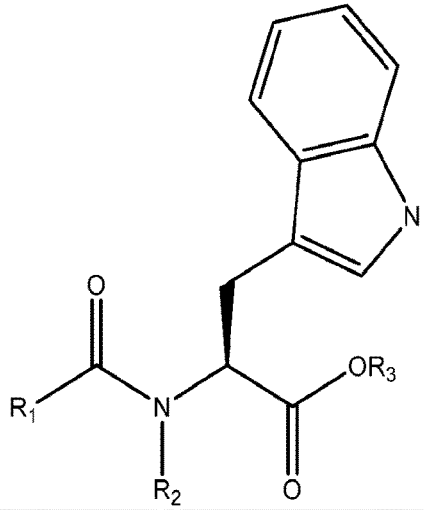
Figure 4:
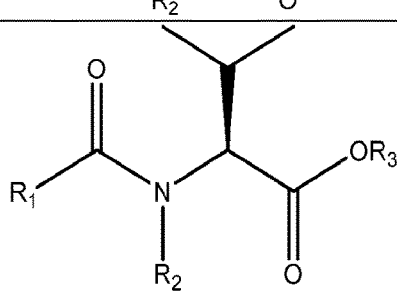
Figure 4:
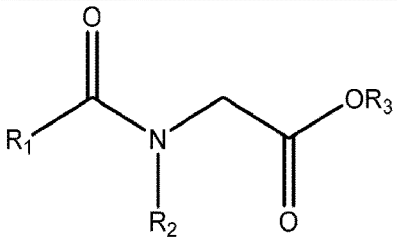
Figure 4:
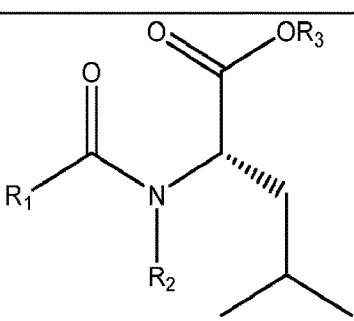
Figure 4:
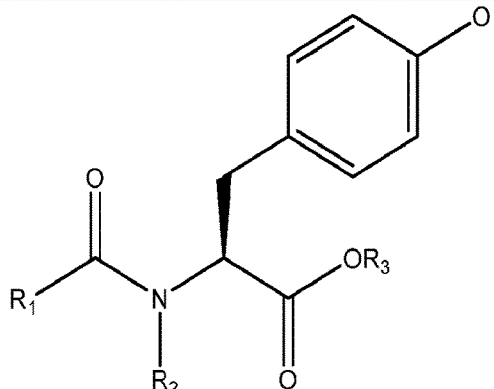
Figure 4:
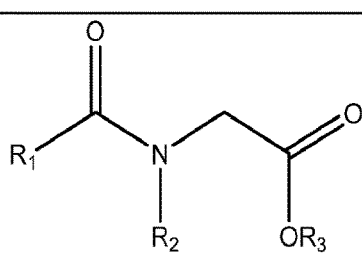

In particular embodiments the acylated FA-aa is selected from the group consisting of formula (a), (b), (c), (d), (e), (f), (g), (h), (i), (j), (k), (l), (m), (n), (o), (p), (q), and (r), wherein R1 is an alkyl group including 5 to 19 carbon atoms, R2 is H (i.e. hydrogen) or CH₃ (i.e. methyl group), and R3 is H; or a salt or the free acid form thereof. Formulas (a), (b), (c), (d), (e), (f), (g), (h), (i), (j), (k), (l), (m), (n), (o), (p), (q), and (r) are provided in FIG. 4.

In particular embodiments, the acylated FA-aa can be selected from one or more of sodium N-dodecanoyl alaninate, N-dodecanoyl-L-alanine, sodium N-dodecanoyl isoleucinate, N-dodecanoyl-L-isoleucine, sodium N-dodecanoyl leucinate, N-dodecanoyl-L-leucine, sodium N-dodecanoyl methioninate, N-dodecanoyl-L-methionine, sodium N-dodecanoyl phenylalaninate, N-dodecanoyl-L-phenylalanine, sodium N-dodecanoyl prolinate, N-dodecanoyl-L-proline, sodium N-dodecanoyl tryptophanate, N-dodecanoyl-L-tryptophane, sodium N-dodecanoyl valinate, N-dodecanoyl-L-valine, sodium N-dodecanoyl sarcosinate, N-dodecanoyl-L-sarcosine, sodium N-oleoyl sarcosinate, sodium N-decyl leucine, sodium N-decanoyl alaninate, N-decanoyl-L-alanine, sodium N-decanoyl leucinate, N-decanoyl-L-leucine, sodium N-decanoyl phenylalaninate, N-decanoyl-L-phenylalanine, sodium N-decanoyl valinate, N-decanoyl-L-valine, sodium N-decanoyl isoleucinate, N-decanoyl-L-isoleucine, sodium N-decanoyl methioninate, N-decanoyl-L-methionine, sodium N-decanoyl prolinate, N-decanoyl-L-proline, sodium N-decanoyl threoninate, N-decanoyl-L-threonine, sodium N-decanoyl tryptophanate, N-decanoyl-L-tryptophane, sodium N-decanoyl sarcosinate, N-decanoyl-L-Sarcosine, N-decanoyl asparaginate, N-decanoyl-L-asparagine, sodium N-decanoyl aspartic acid, N-decanoyl-L-aspartic acid, sodium N-decanoyl cysteinate, N-decanoyl-L-cysteine, sodium N-decanoyl glutaminate, N-decanoyl-L-glutamine, sodium N-decanoyl glycinate, N-decanoyl-L-glycine, sodium N-decanoyl serinate, N-decanoyl-L-serine, sodium N-decanoyl tyrosinate, N-decanoyl-L-tyrosine, sodium N-decanoyl asparaginate, sodium N-dodecanoyl glutamic acid, N-dodecanoyl-L-glutamic acid, sodium N-decanoyl glutamic acid, N-decanoyl-L-glutamic acid, Amisoft HS-11 P (sodium Stearoyl Glutamate, Amisoft MS-11 (sodium Myristoyl Glutamate), Amisoft LS-11 (sodium Dodecanoyl Glutamate), Amisoft CS-11 (sodium Cocoyl Glutamate), sodium N-cocoyl glutamate, Amisoft HS-11 P, Amisoft HS-11 P (sodium N-stearoyl glutamate), (sodium N-myristoyl glutamate)), (sodium N-dodecanoyl glutamate), and Amisoft HS-11 P.

The following acylated FA-aas are commercially available:

| Brand Name | Chemical Name | Provider (per 14-APR-2011) |
| --- | --- | --- |
| Hamposyl L-95 | sodium N-dodecanoyl sarcosinate | Chattem Chemicals |
| Hamposyl O | sodium N-oleoyl sarcosinate | Chattem Chemicals |
| Hamposyl C | sodium N-cocoyl sarcosinate | Chattem Chemicals |
| Hamposyl L-30 | sodium N-dodecanoyl sarcosinate | Chattem Chemicals |
| Amisoft HS-11 P | sodium N-stearoyl glutamate | Ajinomoto |
| Amisoft LS-11 | sodium N-dodecanoyl glutamate | Ajinomoto |
| Amisoft CS-11 | sodium N-cocoyl glutamate | Ajinomoto |
| Amisoft MS-11 | sodium N-myristoyl glutamate | Ajinomoto |
| Amilite GCS-11 | sodium N-cocoyl glycinate | Ajinomoto |

In particular embodiments the terms "fatty acid N-acylated amino acid", "fatty acid acylated amino acid", or "acylated amino acid" are used interchangeably herein and refer to an amino acid that is acylated with a fatty acid at its alpha-amino group.

Particular embodiments utilize vegetable matter with low solubility, or very low solubility. Particular embodiments utilize vegetable matter that is essentially water insoluble. In particular embodiments, solubility in water is defined as low to zero by the United States pharmacopeia (USP 32) according to the amount of water necessary for the dissolution of one part of solute: Low solubility: 100 to 1000 parts of water necessary for dissolution of one part of solute; very low solubility: 1000 to 10 000 parts of water necessary; essentially water insoluble more than 10 000 parts of water necessary. At a basic pH, however, SNAC and other modified amino acids and FA-aas described herein are water soluble. Thus, the administration benefits, as described herein could not be reasonably predicted. In particular embodiments, very low solubility can refer to a solubility in water or an aqueous solution of less than 1 mg/ml, less than 0.1 mg/ml, or less than 0.01 mg/ml.

In particular embodiments, N-acylated fatty amino acids act as absorption enhancing agents, thereby creating an administration benefit. Absorption enhancing agents refer to compounds that promote gastrointestinal absorption. Absorption enhancing agents can improve drug absorption by improving the solubility of the drug in the gastrointestinal tract or by enhancing membrane penetration, as compared to a formulation that does not include the absorption enhancing agents. Additional examples of absorption enhancing agents include surfactants, detergents, azones, pyrrolidones, glycols or bile salts.

In particular embodiments, N-acylated fatty amino acids act as bioavailability enhancing agents. Bioavailability refers to the fraction of active ingredient that is actually absorbed by a subject and reaches the bloodstream. In particular embodiments, bioavailability enhancing agents increase the fraction of active ingredient in the bloodstream or result in detection of active ingredient in the bloodstream earlier in time, as compared to a formulation that does not include the bioavailability enhancing agent.

In particular embodiments, additional administration benefits created by absorption enhancing agents and/or bioavailability enhancing agents include faster onset of action, higher peak concentrations, faster time to peak concentrations, increased subjective therapeutic efficacy, and/or increased objective therapeutic efficacy as compared to a control plant-based composition or oral formulation based on the same, similar in all aspects but for inclusion of the absorption enhancing agents and/or bioavailability enhancing agents.

Embodiments utilizing absorption enhancing agents and/or bioavailability enhancing agents (e.g., and in particular embodiments, N-acylated fatty amino acids) can be beneficial because many oral plant-based compositions designed to address various physiological conditions are inadequate because they are characterized by a delayed onset of action, and low bioavailability. Delayed onset of action presents challenges in clinical indications that require rapid therapeutic effect (e.g. pain and migraine); and low bioavailability requires patients to ingest significantly higher doses than would be required by alternative dosing forms (e.g. smoking, vaping). Particular embodiments disclosed herein provide plant-based composition oral formulations with improved bioavailability and shorter time to onset of therapeutic effect.

As stated, in particular embodiments, N-acylated fatty amino acids act as subjective therapy enhancing agents. Subjective therapy enhancement refers to a noticeable alleviation of a symptom, as perceived by a subject. In particular embodiments, subjective therapy enhancing agents increase the alleviation of a symptom or alleviate a symptom more quickly, as compared to a formulation that does not include the subjective therapy enhancing agent.

In particular embodiments, N-acylated fatty amino acids act as objective therapy enhancing agents. Objective therapy enhancement refers to alleviation of a clinical measure, such as a nutritional deficiency detected by a blood or saliva assay or a test of wellness, as administered by a physician. In particular embodiments, objective therapy enhancing agents increase the alleviation of an objective clinical measure or result in alleviation more quickly, as compared to a formulation that does not include the objective therapy enhancing agent.

Particular embodiments include cannabis and an absorption enhancing agent and/or bioavailability enhancing agent. These embodiments can allow more rapid cannabis absorption and higher bioavailability compared to cannabis ingested by currently available oral dosage forms.

In particular embodiments, carriers disclosed herein create administration benefits selected from: increased absorption, increased bioavailability, faster onset of action, higher peak concentrations, faster time to peak concentrations, increased subjective therapeutic efficacy, increased objective therapeutic efficacy, improved taste, and improved mouthfeel. Administration benefits related to increased absorption, increased bioavailability, faster onset of action, higher peak concentrations, faster time to peak concentrations, can alleviate adverse conditions more rapidly (for example, alleviation of pain). "Mouthfeel" refers to non-taste-related aspects of the pleasantness experienced by a person while ingesting (e.g., chewing or swallowing) an oral dosage form. Aspects of mouthfeel include the hardness and brittleness of a composition, whether the composition is chewy, gritty, oily, creamy, watery, sticky, easily dissolved, astringent, effervescent, and the like, and the size, shape, and form of the composition (tablet, powder, gel, etc.).

Plant-based compositions can be manufactured for administration to a subject by adding vegetable matter, a carrier that provides an administration benefit, and one or more excipients, mixing, suspending, dissolving, blending, granulating, tableting, encapsulating, or performing other dosage-form-specific procedures, followed by packaging. For clarity, carriers contribute to providing an administration benefit. Excipients can, but need not, contribute to an administration benefit.

Particular embodiments include plant-based compositions prepared as oral formulations. Exemplary oral formulations include capsules, coated tablets, edibles, elixirs, emulsions, gels, gelcaps, granules, gums, juices, liquids, oils, pastes, pellets, pills, powders, rapidly-dissolving tablets, sachets, semi-solids, sprays, solutions, suspensions, syrups, tablets, etc.

Exemplary excipient classes include binders, buffers, chelators, coating agents, colorants, complexation agents, diluents (i.e., fillers), disintegrants, emulsifiers, flavoring agents, glidants, lubricants, preservatives, releasing agents, surfactants, stabilizing agents, solubilizing agents, sweeteners, thickening agents, wetting agents, and vehicles.

Binders are substances used to cause adhesion of powder particles in granulations. Exemplary binders include acacia, compressible sugar, gelatin, sucrose and its derivatives, maltodextrin, cellulosic polymers, such as ethylcellulose, hydroxypropylcellulose, hydroxypropylmethyl cellulose, carboxymethylcellulose sodium and methylcellulose, acrylic polymers, such as insoluble acrylate ammoniomethacrylate copolymer, polyacrylate or polymethacrylic copolymer, povidones, copovidones, polyvinylalcohols, alginic acid, sodium alginate, starch, pregelatinized starch, guar gum, and polyethylene glycol.

Colorants may be included in the oral formulations to impart color to the formulation. Exemplary colorants include grape skin extract, beet red powder, beta carotene, annato, carmine, turmeric, and paprika. Additional colorants include FD&C Red No. 3, FD&C Red No. 20, FD&C Yellow No. 6, FD&C Blue No. 2, D&C Green No. 5, FD&C Orange No. 5, D&C Red No. 8, caramel, and ferric oxide.

Diluents can enhance the granulation of oral formulations. Exemplary diluents include microcrystalline cellulose, sucrose, dicalcium phosphate, starches, lactose and polyols of less than 13 carbon atoms, such as mannitol, xylitol, sorbitol, maltitol and pharmaceutically acceptable amino acids, such as glycine.

Disintegrants also may be included in the oral formulations in order to facilitate dissolution. Disentegrants, including permeabilising and wicking agents, are capable of drawing water or saliva up into the oral formulations which promotes dissolution from the inside as well as the outside of the oral formulations. Such disintegrants, permeabilising and/or wicking agents that may be used include starches, such as corn starch, potato starch, pre-gelatinized and modified starches thereof, cellulosic agents, such as Ac-di-sol, montmorrilonite clays, cross-linked PVP, sweeteners, bentonite, microcrystalline cellulose, croscarmellose sodium, alginates, sodium starch glycolate, gums, such as agar, guar, locust bean, karaya, pectin, Arabic, xanthan and tragacanth, silica with a high affinity for aqueous solvents, such as colloidal silica, precipitated silica, maltodextrins, beta-cyclodextrins, polymers, such as carbopol, and cellulosic agents, such as hydroxymethylcellulose, hydroxypropylcellulose and hydroxyopropylmethylcellulose. Dissolution of the oral formulations may be facilitated by including relatively small particles sizes of the ingredients used.

Exemplary dispersing or suspending agents include acacia, alginate, dextran, fragacanth, gelatin, hydrogenated edible fats, methylcellulose, polyvinylpyrrolidone, sodium carboxymethyl cellulose, sorbitol syrup, and synthetic natural gums.

Exemplary emulsifiers include acacia and lecithin.

Flavorants are natural or artificial compounds used to impart a pleasant flavor and often odor to oral formulations. Exemplary flavorants include, natural and synthetic flavor oils, flavoring aromatics, extracts from plants, leaves, flowers, and fruits and combinations thereof. Such flavorants include anise oil, cinnamon oil, vanilla, vanillin, cocoa, chocolate, natural chocolate flavor, menthol, grape, peppermint oil, oil of wintergreen, clove oil, bay oil, anise oil, eucalyptus, thyme oil, cedar leave oil, oil of nutmeg, oil of sage, oil of bitter almonds, cassia oil; citrus oils, such as lemon, orange, lime and grapefruit oils; and fruit essences, including apple, pear, peach, berry, wildberry, date, blueberry, kiwi, strawberry, raspberry, cherry, plum, pineapple, and apricot. In particular embodiments, flavorants that may be used include natural berry extracts and natural mixed berry flavor, as well as citric and malic acid.

Glidants improve the flow of powder blends during manufacturing and minimize oral formulation weight variation. Exemplary glidants include silicon dioxide, colloidal or fumed silica, magnesium stearate, calcium stearate, stearic acid, cornstarch, and talc.

Lubricants are substances used in oral formulations that reduce friction during composition compression. Exemplary lubricants include stearic acid, calcium stearate, magnesium stearate, zinc stearate, talc, mineral and vegetable oils, benzoic acid, poly(ethylene glycol), glyceryl behenate, stearyl fumarate, and sodium lauryl sulfate.

Exemplary preservatives include methyl p-hydroxybenzoates, propyl p-hydroxybenzoates, and sorbic acid.

Exemplary sweeteners include aspartame, dextrose, fructose, high fructose corn syrup, maltodextrin, monoammonium glycyrrhizinate, neohesperidin dihydrochalcone, potassium acesulfame, saccharin sodium, stevia, sucralose, and sucrose.

Particular embodiments include swallowable compositions. Swallowable compositions are those that do not readily dissolve when placed in the mouth and may be swallowed whole without chewing or discomfort. U.S. Pat. Nos. 5,215,754 and 4,374,082 describe methods for preparing swallowable compositions. In particular embodiments, swallowable compositions may have a shape containing no sharp edges and a smooth, uniform and substantially bubble free outer coating.

To prepare swallowable compositions, each of the ingredients may be combined in intimate admixture with a suitable carrier according to conventional compounding techniques. In particular embodiments of the swallowable compositions, the surface of the compositions may be coated with a polymeric film. Such a film coating has several beneficial effects. First, it reduces the adhesion of the compositions to the inner surface of the mouth, thereby increasing the subject's ability to swallow the compositions. Second, the film may aid in masking the unpleasant taste of certain ingredients. Third, the film coating may protect the compositions from atmospheric degradation. Polymeric films that may be used in preparing the swallowable compositions include vinyl polymers such as polyvinylpyrrolidone, polyvinyl alcohol and acetate, cellulosics such as methyl and ethyl cellulose, hydroxyethyl cellulose and hydroxylpropyl methylcellulose, acrylates and methacrylates, copolymers such as the vinyl-maleic acid and styrene-maleic acid types, and natural gums and resins such as zein, gelatin, shellac and acacia.

In particular embodiments, the oral formulations may include chewable compositions. Chewable compositions are those that have a palatable taste and mouthfeel, are relatively soft and quickly break into smaller pieces and begin to dissolve after chewing such that they are swallowed substantially as a solution.

U.S. Pat. No. 6,495,177 describes methods to prepare chewable compositions with improved mouthfeel. U.S. Pat. No. 5,965,162, describes kits and methods for preparing comestible units which disintegrate quickly in the mouth, especially when chewed.

In order to create chewable compositions, certain ingredients should be included to achieve the attributes just described. For example, chewable compositions should include ingredients that create pleasant flavor and mouthfeel and promote relative softness and dissolvability in the mouth. The following discussion describes ingredients that may help to achieve these characteristics.

Sugars such as white sugar, corn syrup, sorbitol (solution), maltitol (syrup), oligosaccharide, isomaltooligosaccharide, sucrose, fructose, lactose, glucose, lycasin, xylitol, lactitol, erythritol, mannitol, isomaltose, dextrose, polydextrose, dextrin, compressible cellulose, compressible honey, compressible molasses and mixtures thereof may be added to improve mouthfeel and palatability. Fondant or gums such as gelatin, agar, arabic gum, guar gum, and carrageenan may be added to improve the chewiness of the compositions. Fatty materials that may be used include vegetable oils (including palm oil, palm hydrogenated oil, corn germ hydrogenated oil, castor hydrogenated oil, cotton-seed oil, olive oil, peanut oil, palm olein oil, and palm stearin oil), animal oils (including refined oil and refined lard whose melting point ranges from 30° to 42° C.), Cacao fat, margarine, butter, and shortening.

Alkyl polysiloxanes (commercially available polymers sold in a variety of molecular weight ranges and with a variety of different substitution patterns) also may be used to enhance the texture, the mouthfeel, or both of chewable compositions. By "enhance the texture" it is meant that the alkyl polysiloxane improves one or more of the stiffness, the brittleness, and the chewiness of the chewable composition, relative to the same preparation lacking the alkyl polysiloxane. By "enhance the mouthfeel" it is meant that the alkyl polysiloxane reduces the gritty texture of the chewable composition once it has liquefied in the mouth, relative to the same preparation lacking the alkyl polysiloxane.

Alkyl polysiloxanes generally include a silicon and oxygen-containing polymeric backbone with one or more alkyl groups pending from the silicon atoms of the back bone. Depending upon their grade, they can further include silica gel. Alkyl polysiloxanes are generally viscous oils. Exemplary alkyl polysiloxanes that can be used in swallowable, chewable or dissolvable compositions include monoalkyl or dialkyl polysiloxanes, wherein the alkyl group is independently selected at each occurrence from a $C_1$-$C_6$-alkyl group optionally substituted with a phenyl group. A specific alkyl polysiloxane that may be used is dimethyl polysiloxane (generally referred to as simethicone). More specifically, a granular simethicone preparation designated simethicone GS may be used. Simethicone GS is a preparation which contains 30% simethicone USP. Simethicone USP contains not less than 90.5% by weight $(CH_3)_3$—$Si\{OSi(CH_3)_2\}CH_3$ in admixture with 4.0% to 7.0% by weight $SiO_2$.

To prevent the stickiness that can appear in some chewable compositions and to facilitate conversion of the active ingredients to emulsion or suspension upon taking, the compositions may further include emulsifiers such as glycerin fatty acid ester, sorbitan monostearate, sucrose fatty acid ester, lecithin and mixtures thereof. In particular embodiments, one or more of such emulsifiers may be present in an amount of 0.01% to 5.0%, by weight of the administered formulations. If the level of emulsifier is lower or higher, in particular embodiments, an emulsification cannot be realized, or wax value will rise.

Liquid preparations for oral administration may take the form of, for example, solutions, syrups or suspensions, or they may be presented as a dry product for reconstitution with water or other suitable vehicles before use.

In addition to those described above, any appropriate fillers and excipients may be utilized in preparing the swallowable, chewable and/or dissolvable compositions or any other oral formulation described herein so long as they are consistent with the described objectives.

Oral formulations also include edibles. Edibles refer to any product that can be consumed as a food or a drink. In some cases, edibles are made by infusion of plant extracts into a foodstuff. Examples of edible foods appropriate for use include candy, a candy bar, bread, a brownie, cake, cheese, chocolate, cocoa, a cookie, gummy candy, a lollipop, a mint, a pastry, peanut butter, popcorn, a protein bar, rice cakes, yogurt, etc. While technically not edible, gums can also be used. Examples of edible drinks include beer, juice, flavored milk, flavored water, liquor, milk, punch, a shake, soda, tea, and water. In particular embodiments, edibles are made by combining a plant extract with ingredients used to make an edible. Examples include butters and oils. Exemplary oils include coconut oil, grape seed oil, olive oil, palm oil, papaya seed oil, peanut oil, sesame oil, sprouted wheat oil, wheat germ oil, or any combination thereof.

Oral formulations can be individually wrapped or packaged as multiple units in one or more packages, cans, vials, blister packs, or bottles of any size. Doses are sized to provide therapeutically effective amounts.

In particular embodiments, the oral formulations include vegetable matter (e.g., plant parts or extracts) of at least 0.1% w/v or w/w of the oral formulation; at least 1% w/v or w/w of oral formulation; at least 10% w/v or w/w of oral formulation; at least 20% w/v or w/w of oral formulation; at least 30% w/v or w/w of oral formulation; at least 40% w/v or w/w of oral formulation; at least 50% w/v or w/w of oral formulation; at least 60% w/v or w/w of oral formulation; at least 70% w/v or w/w of oral formulation; at least 80% w/v or w/w of oral formulation; at least 90% w/v or w/w of oral formulation; at least 95% w/v or w/w of oral formulation; or at least 99% w/v or w/w of oral formulation.

In particular embodiments, the oral formulations include carrier of at least 0.1% w/v or w/w of the oral formulation; at least 1% w/v or w/w of oral formulation; at least 10% w/v or w/w of oral formulation; at least 20% w/v or w/w of oral formulation; at least 30% w/v or w/w of oral formulation; at least 40% w/v or w/w of oral formulation; at least 50% w/v or w/w of oral formulation; at least 60% w/v or w/w of oral formulation; at least 70% w/v or w/w of oral formulation; at least 80% w/v or w/w of oral formulation; at least 90% w/v or w/w of oral formulation; at least 95% w/v or w/w of oral formulation; or at least 99% w/v or w/w of oral formulation.

In particular embodiments, the oral formulations include excipient of at least 0.1% w/v or w/w of the oral formulation; at least 1% w/v or w/w of oral formulation; at least 10% w/v or w/w of oral formulation; at least 20% w/v or w/w of oral formulation; at least 30% w/v or w/w of oral formulation; at least 40% w/v or w/w of oral formulation; at least 50% w/v or w/w of oral formulation; at least 60% w/v or w/w of oral formulation; at least 70% w/v or w/w of oral formulation; at least 80% w/v or w/w of oral formulation; at least 90% w/v or w/w of oral formulation; at least 95% w/v or w/w of oral formulation; or at least 99% w/v or w/w of oral formulation.

In particular embodiments, 10 g of dried plant extract may be used in 150 ml of water. This may give an effective concentration of between 1 and 99% (w/w) plant extract, between 2 and 80% (w/w) plant extract, and between 5 and 50% (w/w) plant extract.

Excipients are commercially available from companies such as Aldrich Chemical Co., FMC Corp, Bayer, BASF, Alexi Fres, Witco, Mallinckrodt, Rhodia, ISP, and others.

Additional information can be found in WADE & WALLER, HANDBOOK OF PHARMACEUTICAL EXCIPIENTS (2nd ed. 1994) and Remington's Pharmaceutical Sciences, 18th Ed. Mack Printing Company, 1990. Moreover, formulations can be prepared to meet sterility, pyrogenicity, general safety, and purity standards as required by U.S. FDA and/or other relevant foreign regulatory agencies.

Plant-based compositions disclosed herein can be used to treat subjects (humans, veterinary animals (dogs, cats, reptiles, birds, etc.), livestock (horses, cattle, goats, pigs, chickens, etc.), and research animals (monkeys, rats, mice, fish, etc.)). Treating subjects includes providing therapeutically effective amounts. Therapeutically effective amounts include those that provide effective amounts, prophylactic treatments, and/or therapeutic treatments.

An "effective amount" is the amount of a plant-based composition necessary to result in a desired physiological change in a subject. Effective amounts are often administered for research purposes. Representative effective amounts disclosed herein can reduce pain perception in an animal model (neuropathic pain, acute pain, visceral pain), stimulate appetite in an animal model, reduce seizures (e.g., epileptic seizures) in an animal model, reverse bone loss in an animal model, relieve migraine (vasoconstrict cranial blood vessels) in an animal model, treat addiction in an animal model, reduce anxiety in an animal model, and/or reduce symptoms of asthma in an animal model.

A "prophylactic treatment" includes a treatment administered to a subject who does not display signs or symptoms of a disease or nutritional deficiency, or displays only early signs or symptoms of a disease or nutritional deficiency, such that treatment is administered for the purpose of diminishing, preventing, or decreasing the risk of developing the disease or nutritional deficiency further. Thus, a prophylactic treatment functions as a preventative treatment against the development of diseases or nutritional deficiencies.

As one example of a prophylactic treatment, an oral formulation disclosed herein can be administered to a subject who is at risk of developing a migraine headache. An effective prophylactic treatment of a migraine headache occurs when the number of migraines per month experienced by a subject is reduced by at least 10% or in particular embodiments, by 25%.

As another example of a prophylactic treatment, an oral formulation disclosed herein can be administered to a subject who is at risk of having an epileptic seizure. An effective prophylactic treatment of epileptic seizures occurs when the number of seizures per month is reduced by at least 10% or in particular embodiments, by 25%.

As another example of a prophylactic treatment, an oral formulation disclosed herein can be administered to a subject who is at risk of suffering from neuropathic pain. An effective prophylactic treatment of neuropathic pain occurs when the occurrence of the neuropathic pain is reduced by at least 10%, or in particular embodiments, by 25% as measured by a standard subjective or objective pain assessment.

As another example of a prophylactic treatment, an oral formulation disclosed herein can be administered to a subject who is at risk of developing breakthrough pain. An effective prophylactic treatment of breakthrough pain occurs when the occurrence of breakthrough pain is reduced by 10%, and in particular embodiments, by 25% by a standard subjective or objective pain assessment.

As another example of a prophylactic treatment, an oral formulation disclosed herein can be administered to a subject who is at risk of developing chemotherapy induced nausea and vomiting (CINV). An effective prophylactic treatment of CINV occurs when CINV is reduced by 10%, and in particular embodiments, by 25% measured by a standard subjective or objective CINV assessment.

As an example of a prophylactic treatment of a nutritional deficiency, an oral formulation disclosed herein can be administered to a subject who is at risk of developing rickets from insufficient vitamin C, anemia from insufficient dietary iron, and/or bone loss from insufficient calcium. An effective prophylactic treatment of these conditions occurs when the conditions are avoided or delayed due to nutritional supplementation with an oral formulation disclosed herein.

A "therapeutic treatment" includes a treatment administered to a subject who has a disease or nutritional deficiency and is administered to the subject for the purpose of curing or reducing the severity of the disease or nutritional deficiency.

As one example of a therapeutic treatment, an oral formulation disclosed herein can be administered to a subject who has a migraine headache. An effective therapeutic treatment of the migraine headache occurs when the severity of the headache is reduced or relieved completely and/or the headache resolves more quickly measured by a standard subjective or objective headache assessment.

Another example of a therapeutic treatment includes administration of an oral formulation disclosed herein to a subject experiencing CINV. A therapeutic treatment of CINV occurs when the vomiting is reduced or ceases (or ceases more quickly) and the nausea is relieved measured by a standard subjective or objective CINV assessment.

Another example of a therapeutic treatment, includes administration of an oral formulation disclosed to a subject who has osteoporosis. An effective therapeutic treatment of osteoporosis occurs when bone density has increased by 10% and in particular embodiments, by 25%.

Another example of a therapeutic treatment includes administration of an oral formulation disclosed herein to a subject who has anxiety. An effective therapeutic treatment of anxiety occurs when the severity of the anxiety is reduced or relieved completely and/or more quickly measured by a standard subjective or objective anxiety assessment.

Another example of a therapeutic treatment includes administration of an oral formulation disclosed herein to a subject who has multiple sclerosis. An effective therapeutic treatment of multiple sclerosis occurs when the score in a standard walk test improves by 10% and in particular embodiments, by 25%.

As one example of a therapeutic treatment of a nutritional deficiency, an oral formulation disclosed herein can be administered to a subject who has rickets from insufficient vitamin C, anemia from insufficient dietary iron, and/or bone loss from insufficient calcium. An effective therapeutic treatment of these conditions occurs when the conditions are reduced or resolved due to nutritional supplementation with an oral formulation disclosed herein.

Therapeutic treatments can be distinguished from effective amounts based on the presence or absence of a research component to the administration. As will be understood by one of ordinary skill in the art, however, in human clinical trials effective amounts, prophylactic treatments and therapeutic treatments can overlap.

For administration, therapeutically effective amounts (also referred to herein as doses) can be initially estimated based on results from in vitro assays and/or animal model studies. Such information can be used to more accurately determine useful doses in subjects of interest.

The actual dose amount administered to a particular subject can be determined by the subject, a physician, veterinarian, or researcher taking into account parameters such as physical, physiological and psychological factors including target, body weight, condition, previous or concurrent therapeutic interventions, and/or idiopathy of the subject.

Useful doses can range from 0.1 to 5 µg/kg or from 0.5 to 1 µg/kg. In particular embodiments, a dose can include 1 µg/kg, 5 µg/kg, 10 µg/kg, 15 µg/kg, 20 µg/kg, 25 µg/kg, 30 µg/kg, 35 µg/kg, 40 µg/kg, 45 µg/kg, 50 µg/kg, 55 µg/kg, 60 µg/kg, 65 µg/kg, 70 µg/kg, 75 µg/kg, 80 µg/kg, 85 µg/kg, 90 µg/kg, 95 µg/kg, 100 µg/kg, 150 µg/kg, 200 µg/kg, 250 µg/kg, 350 µg/kg, 400 µg/kg, 450 µg/kg, 500 µg/kg, 550 µg/kg, 600 µg/kg, 650 µg/kg, 700 µg/kg, 750 µg/kg, 800 µg/kg, 850 µg/kg, 900 µg/kg, 950 µg/kg, 1000 µg/kg, 0.1 to 5 mg/kg or from 0.5 to 1 mg/kg. In particular embodiments, a dose can include 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg or more.

In particular embodiments, useful doses include weight of vegetable matter (e.g., plant parts or extracts) or active ingredient per body weight of a subject. In particular embodiments, useful doses can range from 0.1 mg/kg to 100 mg/kg or from 0.5 mg/kg to 50 mg/kg. In particular embodiments, useful doses include 0.5 mg/kg, 1 mg/kg, 5 mg/kg, 10 mg/kg, 15 mg/kg, 20 mg/kg, 25 mg/kg, or more of vegetable matter or active ingredient per body weight of a subject.

In particular embodiments, useful doses include weight of carrier (e.g., SNAC) per body weight of a subject. In particular embodiments, useful doses can range from 0.1 mg/kg to 100 mg/kg or from 0.5 mg/kg to 50 mg/kg. In particular embodiments, useful doses include 0.5 mg/kg, 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, or more of carrier per body weight of a subject.

In particular embodiments, total dose volume can range from 0.25 mL to 30 mL or from 0.5 mL to 20 mL. In particular embodiments, a total dose volume can include 0.1 mL, 0.2 mL, 0.3 mL, 0.4 mL, 0.5 mL, 0.6 mL, 0.7 mL, 0.8 mL, 0.9 mL, 1 mL, 2 mL, 3 mL, 4 mL, 5 mL, 6 mL, 7 mL, 8 mL, 9 mL, 10 mL, 11 mL, 12 mL, 13 mL, 14 mL, 15 mL, 16 mL, 17 mL, 18 mL, 19 mL, 20 mL, 21 mL, 22 mL, 23 mL, 24 mL, 25 mL, 26 mL, 27 mL, 28 mL, 29 mL, 30 mL, or more.

Dose concentration can be expressed as weight of vegetable matter (e.g., plant parts or extracts) or active ingredient per dose volume (e.g., mg active pharmaceutical ingredient (API)/mL). In particular embodiments, dose concentration can range from 1 mg/mL to 100 mg/mL or from 5 mg/mL to 50 mg/mL. In particular embodiments, a dose concentration can include 1 mg/mL, 2 mg/mL, 3 mg/mL, 4 mg/mL, 5 mg/mL, 6 mg/mL, 7 mg/mL, 8 mg/mL, 9 mg/mL, 10 mg/mL, 11 mg/mL, 12 mg/mL, 13 mg/mL, 14 mg/mL, 15 mg/mL, 16 mg/mL, 17 mg/mL, 18 mg/mL, 19 mg/mL, 20 mg/mL, 21 mg/mL, 22 mg/mL, 23 mg/mL, 24 mg/mL, 25 mg/mL, 30 mg/mL, 35 mg/mL, 40 mg/mL, 45 mg/mL, 50 mg/mL, 55 mg/mL, 60 mg/mL, 65 mg/mL, 70 mg/mL, 75 mg/mL, 80 mg/mL, 85 mg/mL, 90 mg/mL, 95 mg/mL, 100 mg/mL, or more.

Dose concentration can be expressed as weight of carrier (e.g., SNAC) per dose volume (e.g., mg SNAC/mL). In particular embodiments, dose concentration can range from 1 mg/mL to 500 mg/mL or from 50 mg/mL to 300 mg/mL. In particular embodiments, a dose concentration can include 1 mg/mL, 5 mg/mL, 10 mg/mL, 15 mg/mL, 20 mg/mL, 25 mg/mL, 30 mg/mL, 35 mg/mL, 40 mg/mL, 45 mg/mL, 50 mg/mL, 55 mg/mL, 60 mg/mL, 65 mg/mL, 70 mg/mL, 75 mg/mL, 80 mg/mL, 85 mg/mL, 90 mg/mL, 95 mg/mL, 100 mg/mL, 125 mg/mL, 150 mg/mL, 175 mg/mL, 200 mg/mL, 225 mg/mL, 250 mg/mL, 275 mg/mL, 300 mg/mL, 325 mg/mL, 350 mg/mL, 375 mg/mL, 400 mg/mL, 425 mg/mL, 450 mg/mL, 475 mg/mL, 500 mg/mL, or more.

In particular embodiments, the ratio of carrier to vegetable matter (e.g., plant parts or extracts) or active ingredient (w/w) can range from 1:1 to 100:1 or from 1:1 to 20:1. In particular embodiments, the ratio can include 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 25:1, 30:1, 35:1, 40:1, 45:1, 50:1, 55:1, 60:1, 65:1, 70:1, 75:1, 80:1, 85:1, 90:1, 95:1, 100:1, or more. In particular embodiments, the ratio can be 10:1.

Therapeutically effective amounts can be achieved by administering single or multiple doses during the course of a treatment regimen (e.g., hourly, every 2 hours, every 3 hours, every 4 hours, every 6 hours, every 9 hours, every 12 hours, every 18 hours, daily, every other day, every 3 days, every 4 days, every 5 days, every 6 days, weekly, every 2 weeks, every 3 weeks, or monthly).

One or more active agent(s) can be administered simultaneously or within a selected time window, such as within 10 minutes, 1 hour, 3 hour, 10 hour, 15 hour, 24 hour, or 48 hour time windows or when the complementary active agent(s) is within a clinically-relevant therapeutic window.

The Exemplary Embodiments and Examples below are included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure.

EXEMPLARY EMBODIMENTS

1. A plant-based composition including vegetable matter and an N-acylated fatty amino acid or a salt thereof.
2. A plant-based composition of embodiment 1 including a botanical product.
3. A plant-based composition of embodiment 1 or 2 wherein the vegetable matter is derived from *Calophyllum brasiliense, Calophyllum caledonicurn, Calophyllum inophyllum, Calophyllum soulattri, Uncaria tomentosa, Thymus vulgaris, Matricaria recutita, Salix alba, Calendula officinalis, Usnea barbata, Ligusticum porterii-osha, Gaultheria procumbens, Camellia sinensis, Vaccinium myrtillus, Melissa officinalis, Allium sativum, Camellia sinensis, Krameria triandra, Punica granatum, Viburnum plicatum, Nicotiana tabacum, Duboisia hopwoodii, Asclepias syriaca, Curcuma longa, Cannabis sativa, Cannabis indica, Cannabis ruderalis* and/or *Acer* spp, or an extract thereof.
4. A plant-based composition of any of embodiments 1-3 wherein the vegetable matter is derived from cannabis.
5. A plant-based composition of any of embodiments 1-4 wherein the vegetable matter is derived from *Cannabis sativa, Cannabis ruderalis,* or *Cannabis indica*.
6. A plant-based composition of any of embodiments 1-5 including a cannabis extract.
7. A plant-based composition of any of embodiments 1-6 including cannabinoids.
8. A plant-based composition of any of embodiments 1-7 including Δ9-Tetrahydrocannabinol (THC) and cannabidiol (CBD), cannabigerol (CBG), cannabichromene (CBC), cannabinol (CBN), cannabinodiol (CBDL), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), cannabinerolic acid, cannabidiolic acid (CBDA), Cannabinol propyl variant (CBNV), cannabitriol (CBO), tetrahydrocannabinolic acid (THCA), tetrahydrocannabivarinic acid (THCVA), and/or mixtures thereof.
9. A plant-based composition of any of embodiments 1-8 including flavonoid compounds, terpenes, or terpenoids.
10. A plant-based composition of any of embodiments 1-9 wherein the N-acylated fatty amino acid includes one or more of Compounds I-XXXV (FIG. 3), or Compounds a-r (FIG. 4).
11. A plant-based composition of any of embodiments 1-10 wherein the N-acylated fatty amino acid includes monosodium-N-salicyloyl-8-aminocaprylate, disodium-N-salicyloyl-8-aminocaprylate, and N-(salicyloyl)-8-aminocaprylic acid.
12. A plant-based composition of any of embodiments 1-11 wherein the N-acylated fatty amino acid or a salt thereof includes

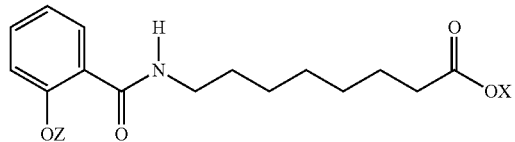

wherein X and Z are independently H, a monovalent cation, a divalent metal cation, or an organic cation.
13. A plant-based composition of embodiment 12, wherein the monovalent cation includes sodium or potassium.
14. A plant-based composition of embodiment 12, wherein the metal cation includes calcium or magnesium.
15. A plant-based composition of embodiment 12, wherein the organic cation includes ammonium or tetramethylammonium.
16. The plant-based composition of embodiment 12, wherein X is H.
17. The plant-based composition of embodiment 12, wherein X is a monovalent cation including sodium or potassium.

18. The plant-based composition of embodiment 12, wherein X is a divalent metal cation including calcium or magnesium.
19. The plant-based composition of embodiment 12, wherein X is an organic cation including ammonium or tetramethylammonium.
20. The plant-based composition of embodiment 12, wherein Z is H.
21. The plant-based composition of embodiment 12 wherein Z is a monovalent cation comprising sodium or potassium.
22. The plant-based composition of embodiment 12 wherein Z is a divalent cation comprising calcium or magnesium.
23. The plant-based composition of embodiment 12, wherein X is H and Z is H.
24. The plant-based composition of embodiment 12, wherein X is H and Z is sodium.
25. The plant-based composition of embodiment 12, wherein X is sodium and Z is sodium.
26. A plant-based composition of any of embodiments 1-25 wherein the N-acylated fatty amino acid provides an administration benefit.
27. A plant-based composition of embodiment 26 wherein the administration benefit is a dose-dependent administration benefit.
28. A plant-based composition of embodiment 27 wherein the dose-dependent administration benefit is at a dose of 25-200 mg.
29. The plant-based composition of embodiment 27, wherein the dose-dependent administration benefit is at a dose concentration of 1 mg/mL to 500 mg/mL N-acylated fatty amino acid or salt thereof.
30. The plant-based composition of embodiment 27, wherein the dose-dependent administration benefit of the N-acylated fatty amino acid or salt thereof is at a dose one to one hundred times the dose level of the vegetable matter.
31. An plant-based composition of embodiment 26 wherein the administration benefit includes one or more of increased absorption of a measured component of vegetable matter, increased bioavailability of a measured component of vegetable matter, faster onset of action of a measured component of vegetable matter, higher peak concentrations of a measured component of vegetable matter, faster time to peak concentrations of a measured component of vegetable matter, increased subjective therapeutic efficacy, increased objective therapeutic efficacy, improved taste, and improved mouthfeel as compared to a control composition without the N-acylated fatty amino acid.
32. A plant-based composition of any of embodiments 1-31 wherein the plant-based composition is a medicinal composition.
33. A plant-based composition of any of embodiments 1-32 wherein the plant-based composition is a nutritional supplement.
34. A plant-based composition of any of embodiments 1-33 including a surfactant, detergent, azone, pyrrolidone, glycol or bile salt.
35. A plant-based composition of any of embodiments 1-34 including a therapeutically effective amount of vegetable matter.
36. The plant-based composition of embodiment 35, wherein the therapeutically effective amount of vegetable matter is at a dose concentration of 1 mg/mL to 50 mg/mL.
37. The plant-based composition of embodiment 35, wherein the therapeutically effective amount of vegetable matter is at a dose one to one hundred times less than the dose of the N-acylated fatty amino acid or salt thereof.
38. A plant-based composition of embodiment 35 wherein the therapeutically effective amount treats a symptom of acquired hypothyroidism, acute gastritis, addiction, ADHD, agoraphobia, AIDS, AIDS-related anorexia, alcoholism, Alzheimer's disease, amyotrophic lateral sclerosis (ALS), ankyloses, anxiety, arthritis, Asperger's syndrome, asthma, atherosclerosis, autism, auto-immune diseases, bacterial infections, bipolar disorder, bone loss, blood disorders, brain injury/stroke, cachexia, cancer, carpal tunnel syndrome, cerebral palsy, cervical disk disease, cervicobrachial syndrome, chronic fatigue syndrome, chronic pain, cluster headache, conjunctivitis, Crohn's disease, cystic fibrosis, depression, dermatitis, diabetes, dystonia, eating disorders, eczema, epilepsy, fever, fibromyalgia, flu, fungal infection, gastrointestinal disorders, glaucoma, glioma, Grave's disease, heart disease hepatitis, herpes, Huntington's disease, hypertension, impotence, incontinence, infant mortality, inflammation, inflammatory bowel disease (IBD), insomnia, liver fibrosis, mad cow disease, menopause, metabolic disorders, migraine headaches, motion sickness, MRSA, multiple sclerosis (MS), muscular dystrophy, mucosal lesions, nail patella syndrome, nausea and vomiting associated with cancer chemotherapy, neuroinflammation, nicotine addiction, obesity, obsessive compulsive disorder (OCD), pain, pancreatitis, panic disorder, Parkinson's disease, periodontal disease, peripheral neuropathy, phantom limb pain, poison ivy allergy, premenstrual syndrome (PMS), proximal myotonic myopathy, post-traumatic stress disorder (PTSD), psoriasis, Raynaud's disease, restless leg syndrome, schizophrenia, scleroderma, septic shock, shingles herpes zoster), sickle cell disease, seizures, sleep apnea, sleep disorders, spinal injuries, stress, stuttering, temporomandibular joint disorder (TMJ), tension headaches, tinnitus, Tourette's syndrome, traumatic memories, wasting syndrome, and withdrawal.
39. A plant-based composition of any of embodiments 1-38 including vitamins or minerals.
40. A plant-based composition of any of embodiments 1-38 including vitamins and minerals.
41. A plant-based composition of embodiments 39 or 40 wherein the vitamins are selected from one or more of Vitamin A, Vitamin B1, Vitamin B6, Vitamin B12, Vitamin C, Vitamin D, Vitamin E, or Vitamin K.
42. A plant-based composition of any of embodiments 39-40 wherein the minerals are selected from one or more of calcium, chromium, iodine, iron, magnesium, selenium or zinc.
43. An oral formulation including a plant-based composition of any of embodiments 1-42.
44. An oral formulation of embodiment 43 wherein the oral formulation is swallowable or chewable.
45. An oral formulation of embodiment 43 or 44 wherein the oral formulation is liquid or solid.
46. An oral formulation of any of embodiments 43-45 wherein the oral formulation is a solution, suspension, or spray.
47. An oral formulation of any of embodiments 43-45 wherein the oral formulation is a tablet, capsule or sachet.
48. An oral formulation of any of embodiments 43-47 wherein the oral formulation is flavored.
49. A method of preparing an oral formulation of cannabis having a faster onset of action, wherein the method comprises adding an absorption enhancer to the oral formulation of cannabis and wherein the oral formulation of cannabis has a faster onset of action than an oral formulation of cannabis without an absorption enhancer.

50. The method of embodiment 49, wherein the absorption enhancer is an N-acylated fatty amino acid or a salt thereof.

51. The method of embodiment 49 or 50, wherein the N-acylated fatty amino acid or a salt thereof comprises

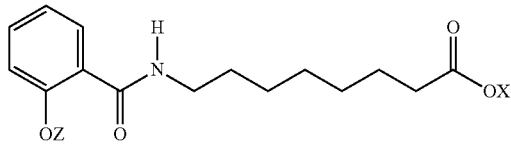

wherein X and Z are independently H, a monovalent cation, a divalent metal cation, or an organic cation.

52. The method of any one of embodiments 49-51, wherein the N-acylated fatty amino acid is selected from monosodium-N-salicyloyl-8-aminocaprylate, disodium-N-salicyloyl-8-aminocaprylate, and N-(salicyloyl)-8-aminocaprylic acid.

53. The method of embodiment 49, wherein the absorption enhancer is in an amount one to one hundred times the amount of cannabis.

54. A method of treating a subject in need thereof including administering a therapeutically effective amount of a composition of any of embodiments 1-42 or a formulation of any of embodiments 43-48 to the subject thereby treating the subject in need thereof.

55. A method of embodiment 54 wherein the therapeutically effective amount provides an effective amount, a prophylactic treatment, and/or a therapeutic treatment.

56. The method of embodiment 54, wherein the therapeutically effective amount of the composition comprises the N-acylated fatty amino acid or salt thereof at a dose one to one hundred times the dose of the vegetable matter.

57. A method of reducing or eliminating one or more symptoms of a disease or disorder in a human subject, wherein said method includes delivering a therapeutically effective amount of a composition of any of embodiments 1-42 or oral formulation of any of embodiments 43-48 to the subject, thereby reducing or eliminating one or more symptoms of the disease or disorder, and wherein said disease or disorder is acquired hypothyroidism, acute gastritis, addiction, ADHD, agoraphobia, AIDS, AIDS-related anorexia, alcoholism, Alzheimer's disease, amyotrophic lateral sclerosis (ALS), ankyloses, anxiety, arthritis, Asperger's syndrome, asthma, atherosclerosis, autism, auto-immune diseases, bacterial infections, bipolar disorder, bone loss, blood disorders, brain injury/stroke, cachexia, cancer, carpal tunnel syndrome, cerebral palsy, cervical disk disease, cervicobrachial syndrome, chronic fatigue syndrome, chronic pain, cluster headache, conjunctivitis, Crohn's disease, cystic fibrosis, depression, dermatitis, diabetes, dystonia, eating disorders, eczema, epilepsy, fever, fibromyalgia, flu, fungal infection, gastrointestinal disorders, glaucoma, glioma, Grave's disease, heart disease hepatitis, herpes, Huntington's disease, hypertension, impotence, incontinence, infant mortality, inflammation, inflammatory bowel disease (IBD), insomnia, liver fibrosis, mad cow disease, menopause, metabolic disorders, migraine headaches, motion sickness, MRSA, multiple sclerosis (MS), muscular dystrophy, mucosal lesions, nail patella syndrome, nausea and vomiting associated with cancer chemotherapy, neuroinflammation, nicotine addiction, obesity, obsessive compulsive disorder (OCD), osteoporosis, osteopenia, pain, pancreatitis, panic disorder, Parkinson's disease, periodontal disease, peripheral neuropathy, phantom limb pain, poison ivy allergy, premenstrual syndrome (PMS), proximal myotonic myopathy, post-traumatic stress disorder (PTSD), psoriasis, Raynaud's disease, restless leg syndrome, schizophrenia, scleroderma, septic shock, shingles herpes zoster), sickle cell disease, seizures, sleep apnea, sleep disorders, spinal injuries, stress, stuttering, temporomandibular joint disorder (TMJ), tension headaches, tinnitus, Tourette's syndrome, traumatic memories, wasting syndrome, or withdrawal syndrome.

58. The method of embodiment 57, wherein the therapeutically effective amount of the composition comprises the N-acylated fatty amino acid or salt thereof at a dose one to one hundred times the dose of the vegetable matter.

EXAMPLES

Oral cannabinoid dosage form providing improved bioavailability and shortened time to onset of effect. Considering the wealth of medical conditions potentially benefiting from cannabis therapy, a significant unmet need exists for a faster-acting product that provides improved bioavailability in an oral format. Current oral cannabis products include edibles and traditional pharmaceutical dosage forms that are challenged by low bioavailability, and prolonged time to onset of action. The present disclosure addresses the shortcomings of all of the currently available oral cannabis products to provide an improved time to onset of effect and improved bioavailability.

Example 1

Exemplary Formulations. Solution formulation. Cannabis and one or more N-acylated fatty amino acids are combined in an aqueous/organic solvent mixture. The resulting blend is stirred vigorously for an hour. If solution is incomplete, a surfactant can be added and stirring can be continued to prepare the final formulation.

Suspension formulation. Cannabis and one or more N-acylated fatty amino acids are combined in water, an aqueous/organic solvent mixture or an organic solvent mixture. The resulting blend can be stirred to effect suspension.

Solution formulation. Cannabis and one or more absorption enhancing agents are combined in an aqueous/organic solvent mixture. The resulting blend is stirred vigorously for an hour. If solution is incomplete, a surfactant can be added and stirring can be continued to prepare the final formulation.

Suspension formulation. Cannabis and one or more absorption enhancing agents are combined in water, an aqueous/organic solvent mixture or an organic solvent mixture. The resulting blend can be stirred to effect suspension.

Gelcap composition. A suspension formulation or solution formulation can be filled into a gelcap to contain up to 1 g of cannabis. The gelcap can be treated with an enteric coat or used without a coating.

Tablet/capsule composition. The solution formulation and the suspension formulation can be dried by evaporation, lyophilization, or spray drying. The resultant dry product can be combined with tableting excipients and compressed into tablets or caplets to contain up to 1 g of cannabis. Alternatively, the dry product can be filled into capsules.

Example 2

Onset and duration of action of orally administered cannabis/SNAC composition. This study was designed to assess the utility of SNAC in enabling a rapid-acting oral form of cannabis.

Selection of Participants. Six study participants were recruited to ingest cannabis compositions and record the onset, duration, and intensity of cannabis-induced euphoria and/or dysphoria. Study participants took part in two separate tests: 1) use of a control substance, which included liquid cannabis extract dissolved in aqueous ethanol, and 2) use of a test substance, which included the liquid cannabis extract dissolved in aqueous ethanol, as well as SNAC.

Formulations. The selected cannabis concentrate is commercially available and was provided to participants in an ethanol solution. The concentrate contains 8 mg THC per dose. It was selected because it contains a high percentage of THC, which provides a noticeable effect on user-reported "euphoria". Aqueous ethanol was used as solvent because it effectively dissolves cannabis extract, as well as SNAC.

Methods. For the Control experiment, each participant mixed the cannabis concentrate with 15 ml (one tablespoon) of aqueous ethanol, and immediately swallowed the mixture.

For the Test experiment, each participant mixed the cannabis concentrate with a pre-mixed solution of aqueous ethanol and 200 mg SNAC, and immediately swallowed the dissolved mixture.

For both the Control experiment and the Test experiment, each participant recorded the time of dose administration, the time of onset of euphoria and/or dysphoria, and the observed level of euphoria and/or dysphoria in fifteen minute intervals for five hours following administration of the cannabis dose. Euphoria and dysphoria were reported using a scale value, in a range from 1-10. Table 1 shows descriptions of euphoria and dysphoria levels for each scale value.

TABLE 1

Scale Values for Reporting Euphoria and Dysphoria

| Scale Value | Description |
|---|---|
| 0 | No observed effect |
| 1-2 | Mild observed effect; possibly psychological |
| 3-4 | Definite but mild effect |
| 5-6 | Definite substantial effect |
| 7-8 | Strong effect |
| 9-10 | Intense effect |

Figure 5A:
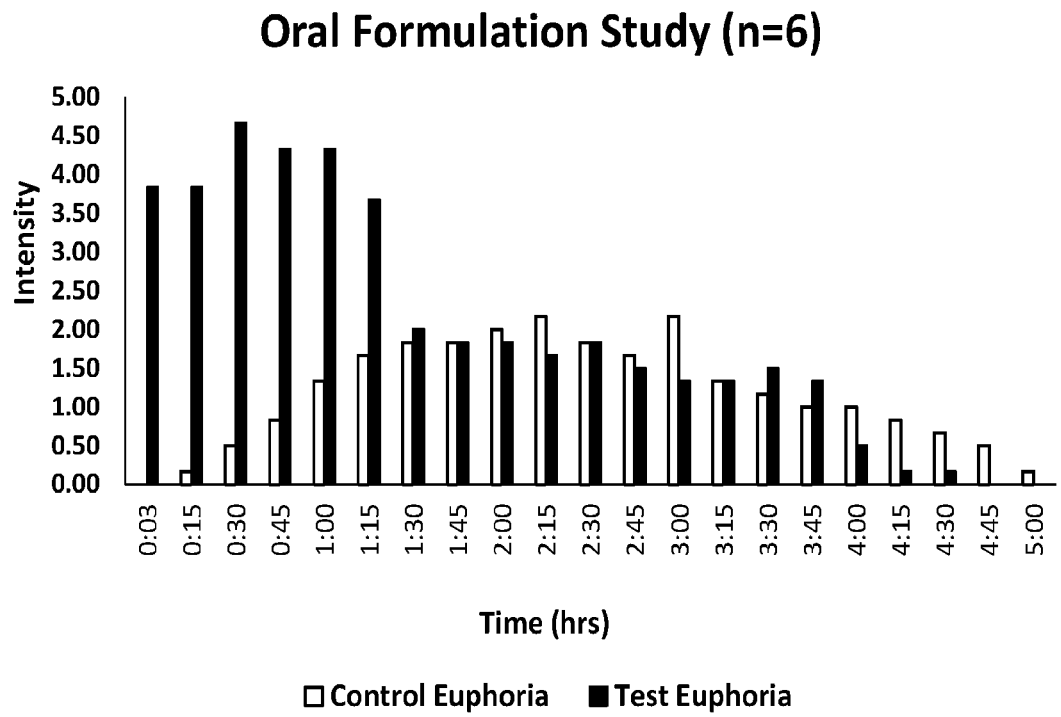
FIGS. 5A and 5B provide the average results of the study comparing onset and duration of action of orally administered cannabis/N-[8-(2-hydroxybenzoyl) amino] caprylate (SNAC, "test") formulation and cannabis (without SNAC, "control") formulation.
Figure 5B:
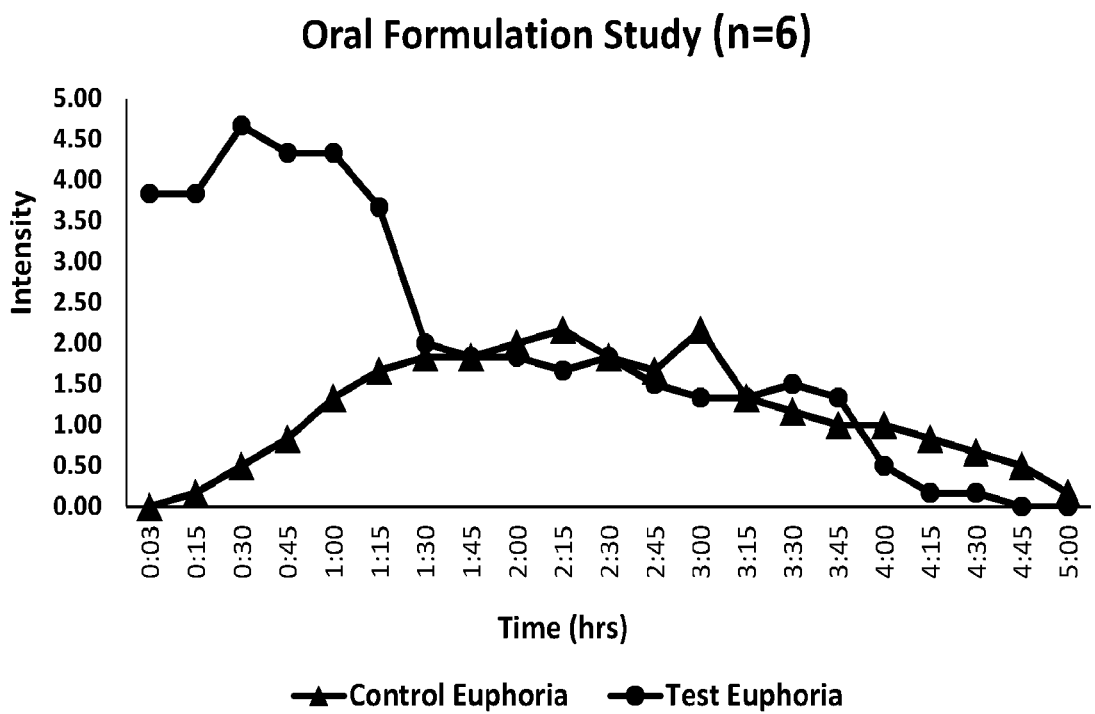
Figure 6A:
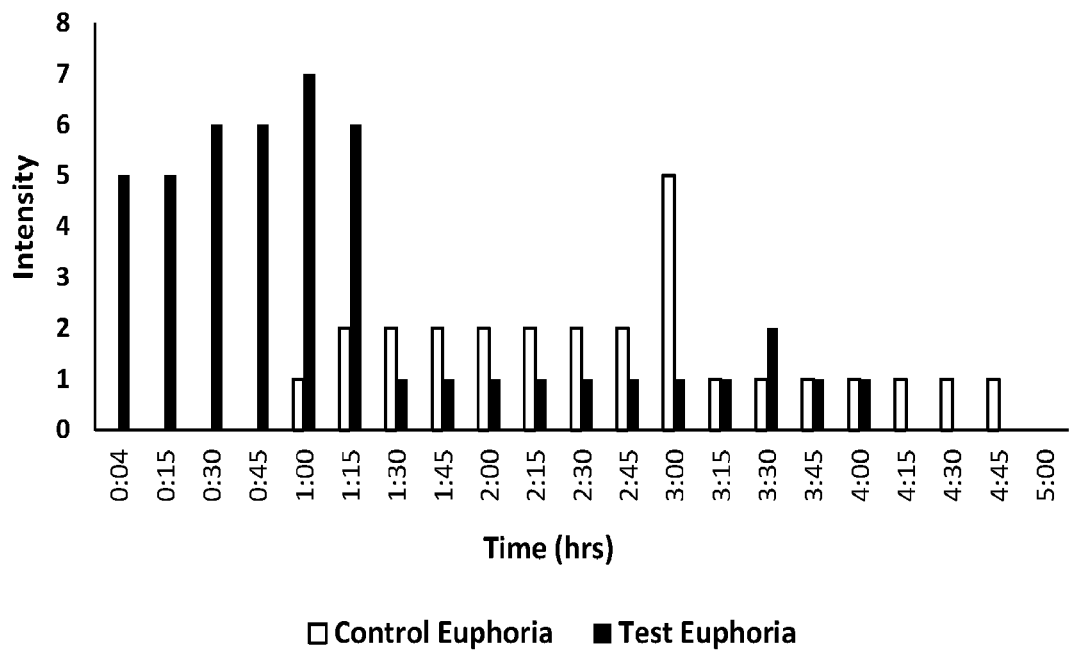
FIGS. 6A-6F provide the results for each individual participant in the study comparing onset and duration of action of orally administered cannabis/N-[8-(2-hydroxybenzoyl) amino] caprylate (SNAC, "test") formulation and cannabis (without SNAC, "control") formulation.
Figure 6B:
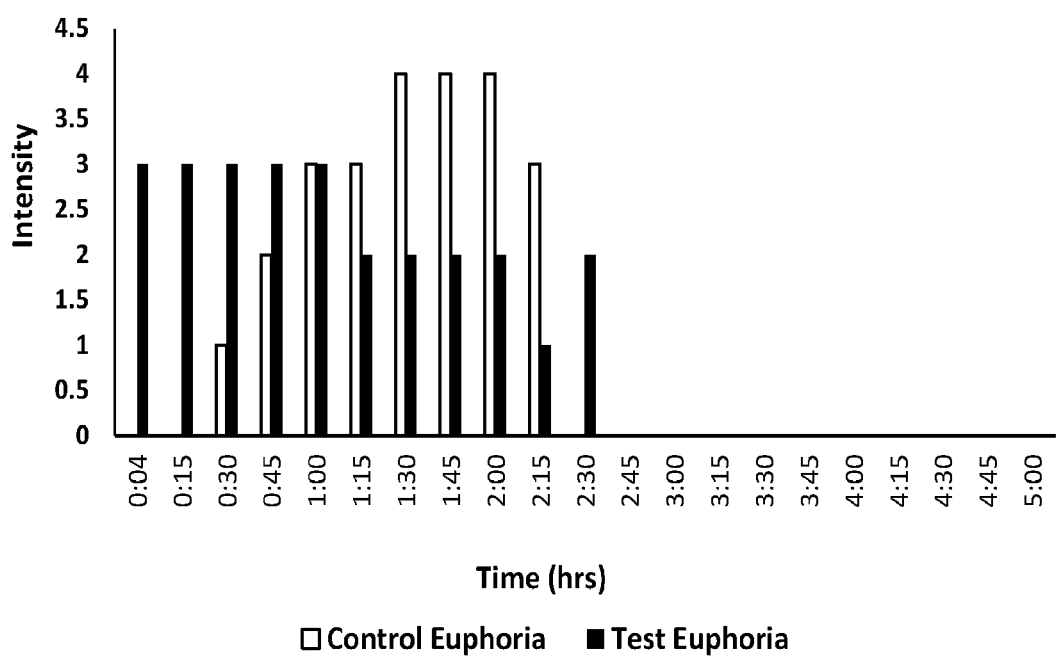
Figure 6C:
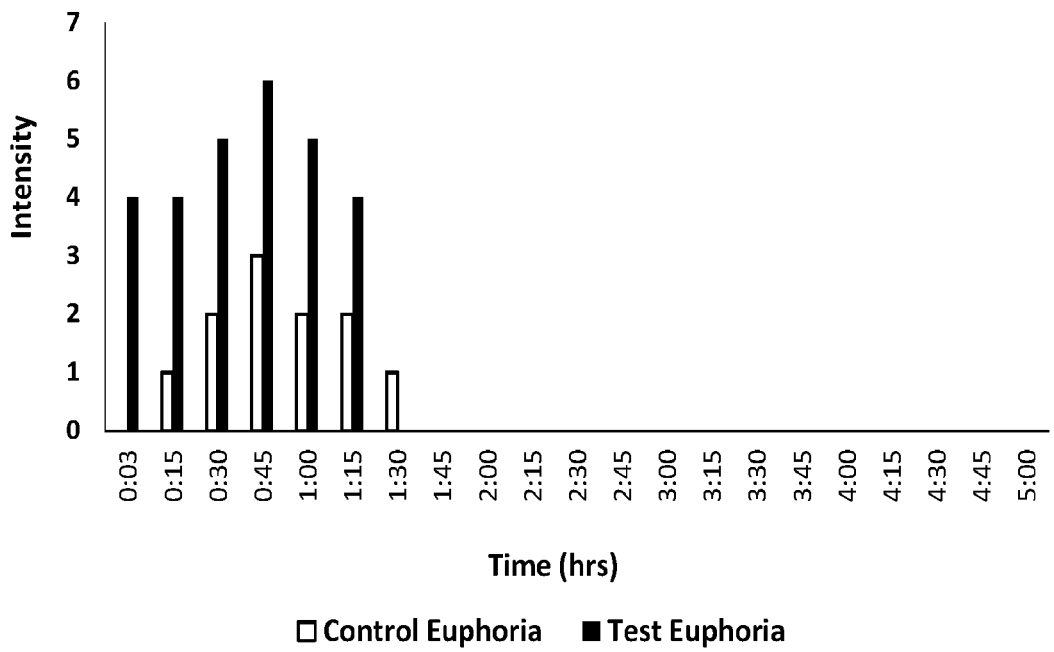
Figure 6D:
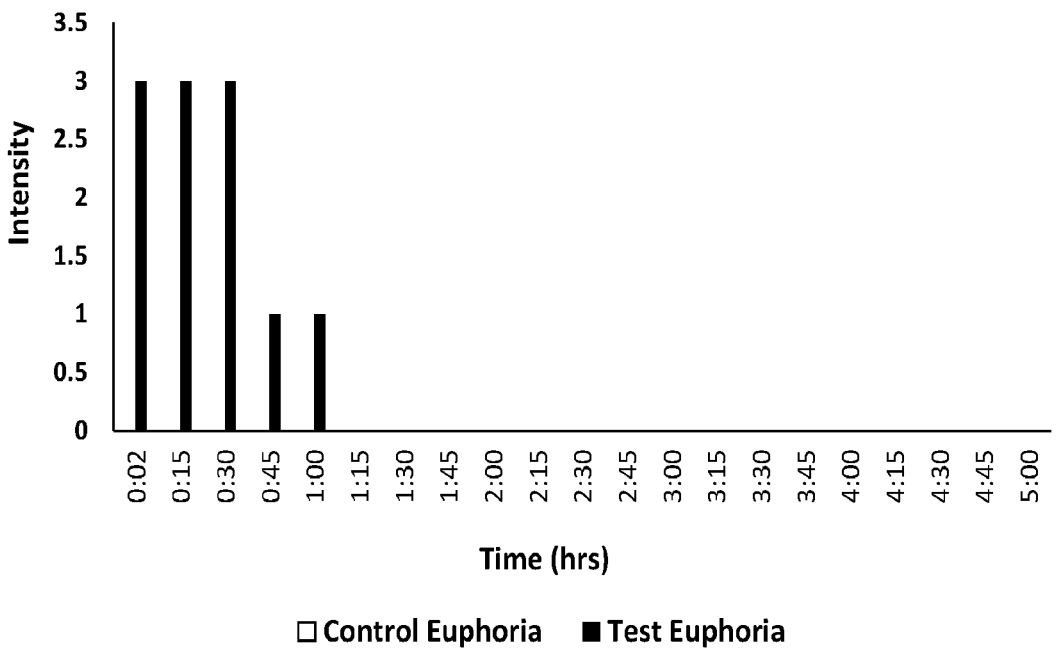
Figure 6E:
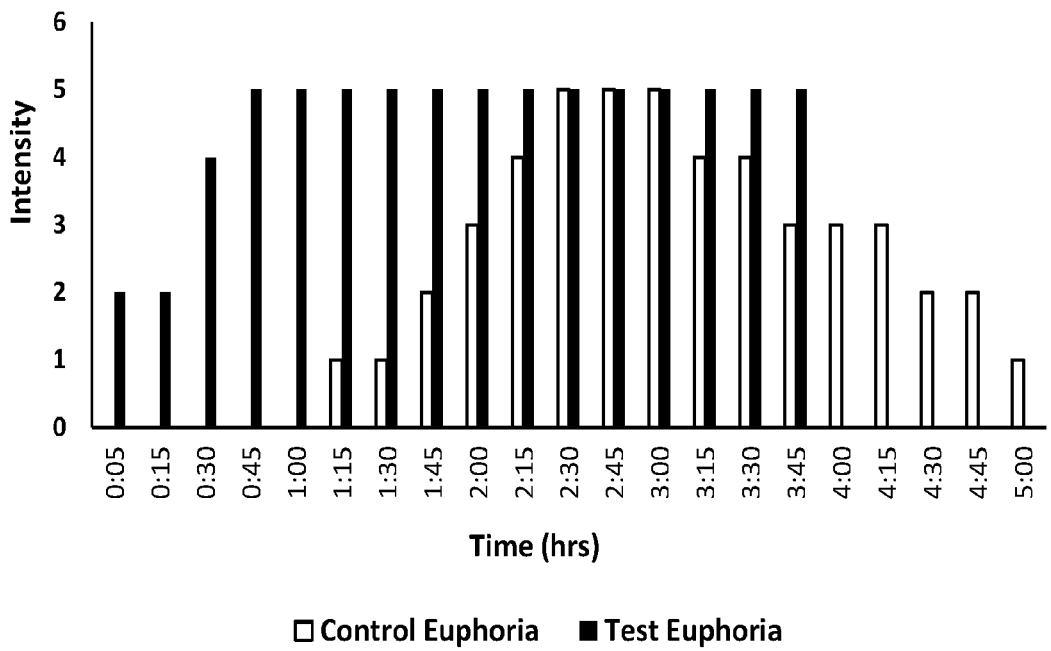
Figure 6F:
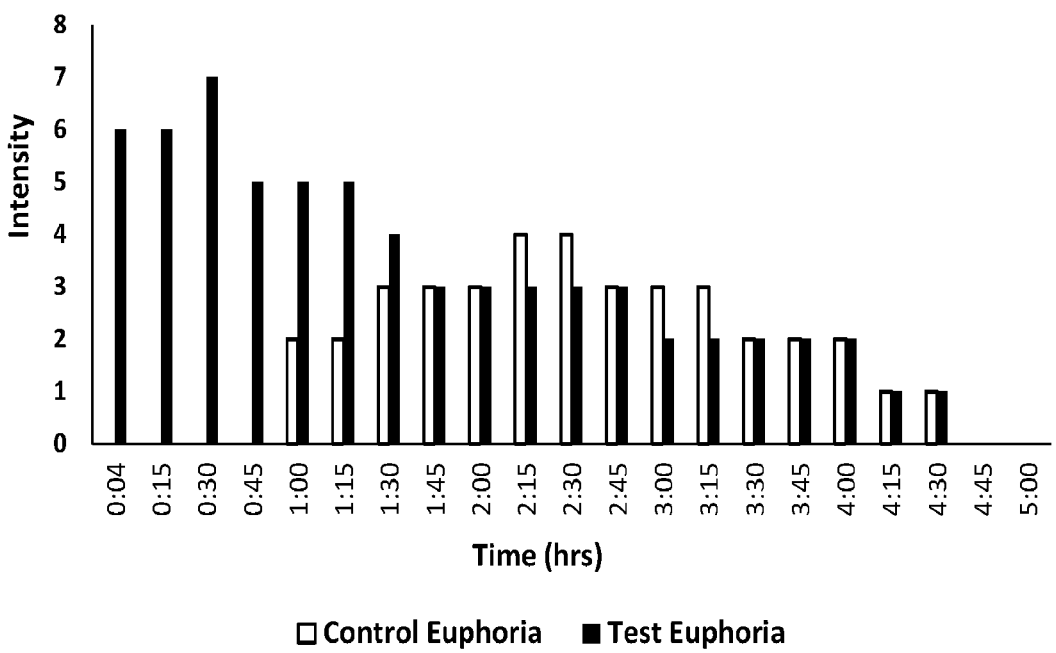

Results. The results shown below are the average scale values obtained for all six participants (also shown in FIGS. 5A and 5B).

TABLE 2

Control Experiment (n = 6)

| Actual Time 12:00 PM | Time from Start 0:00 | Observed "Euphoria" (0-10) | Observed "Dysphoria" (0-10) |
|---|---|---|---|
| 12:15 PM | 0:15 | 0.17 | 0.00 |
| 12:30 PM | 0:30 | 0.50 | 0.00 |
| 12:45 PM | 0:45 | 0.83 | 0.17 |
| 1:00 PM | 1:00 | 1.33 | 0.17 |
| 1:15 PM | 1:15 | 1.67 | 0.50 |

TABLE 2-continued

Control Experiment (n = 6)

| Actual Time 12:00 PM | Time from Start 0:00 | Observed "Euphoria" (0-10) | Observed "Dysphoria" (0-10) |
|---|---|---|---|
| 1:30 PM | 1:30 | 1.83 | 0.67 |
| 1:45 PM | 1:45 | 1.83 | 0.83 |
| 2:00 PM | 2:00 | 2.00 | 0.50 |
| 2:15 PM | 2:15 | 2.17 | 0.50 |
| 2:30 PM | 2:30 | 1.83 | 0.33 |
| 2:45 PM | 2:45 | 1.67 | 0.33 |
| 3:00 PM | 3:00 | 2.17 | 0.33 |
| 3:15 PM | 3:15 | 1.33 | 0.17 |
| 3:30 PM | 3:30 | 1.17 | 0.00 |
| 3:45 PM | 3:45 | 1.00 | 0.00 |
| 4:00 PM | 4:00 | 1.00 | 0.00 |
| 4:15 PM | 4:15 | 0.83 | 0.00 |
| 4:30 PM | 4:30 | 0.67 | 0.00 |
| 4:45 PM | 4:45 | 0.50 | 0.00 |
| 5:00 PM | 5:00 | 0.17 | 0.00 |

TABLE 3

Test Experiment (n = 6)

| Actual Time 12:00 PM | Time from Start 0:00 | Observed "Euphoria" (0-10) | Observed "Dysphoria" (0-10) |
|---|---|---|---|
| 12:03 PM | 0:03 | 3.83 | 0.67 |
| 12:15 PM | 0:15 | 3.83 | 0.67 |
| 12:30 PM | 0:30 | 4.67 | 0.83 |
| 12:45 PM | 0:45 | 4.33 | 0.50 |
| 1:00 PM | 1:00 | 4.33 | 0.50 |
| 1:15 PM | 1:15 | 3.67 | 0.67 |
| 1:30 PM | 1:30 | 2.00 | 0.17 |
| 1:45 PM | 1:45 | 1.83 | 0.17 |
| 2:00 PM | 2:00 | 1.83 | 0.00 |
| 2:15 PM | 2:15 | 1.67 | 0.00 |
| 2:30 PM | 2:30 | 1.83 | 0.00 |
| 2:45 PM | 2:45 | 1.50 | 0.00 |
| 3:00 PM | 3:00 | 1.33 | 0.17 |
| 3:15 PM | 3:15 | 1.33 | 0.17 |
| 3:30 PM | 3:30 | 1.50 | 1.00 |
| 3:45 PM | 3:45 | 1.33 | 0.00 |
| 4:00 PM | 4:00 | 0.50 | 0.00 |
| 4:15 PM | 4:15 | 0.17 | 0.00 |
| 4:30 PM | 4:30 | 0.17 | 0.00 |
| 4:45 PM | 4:45 | 0.00 | 0.00 |
| 5:00 PM | 5:00 | 0.00 | 0.00 |

Onset: All six participants reported euphoria within five minutes of ingesting the cannabis/SNAC formulation (Test), with the time of onset ranging between two and five minutes. In contrast, the first time-point of euphoria reported by participants after ingestion of the cannabis-only formulation (Control) was fifteen minutes post-ingestion, with the time of onset ranging between fifteen minutes and one hour, fifteen minutes (see FIGS. 6A-6F for individual participant results). By fifteen minutes post-ingestion, the average reported euphoria scale value was 3.8 for the cannabis/SNAC formulation (Test). In contrast, fifteen minutes after ingestion of the cannabis-only formulation (Control), the average reported euphoria scale value was 0.17 (see FIGS. 5A-5B for averages at each time-point).

Intensity: The average peak euphoria scale value after ingestion of the cannabis/SNAC formulation (Test) was 4.7, which occurred thirty minutes post-ingestion. In contrast, the highest average euphoria scale value after ingestion of the cannabis-only formulation (Control) was 2.2, which was at the two hour, fifteen minute time-point (see FIGS. 5A and 5B). Therefore, ingestion of the cannabis/SNAC formulation led to a higher peak intensity of euphoria, which occurred an average of one hour and forty-five minutes faster than when the cannabis-only formulation was ingested. The intensity of observed dysphoria was minimal for both the Test and Control, with a peak average scale value of 0.83 for both experiments.

Duration: The results indicate that the addition of an absorption enhancer does not shorten the duration of action of cannabis.

In summary, adding an absorption enhancer, such as SNAC, in an oral dosage formulation of cannabis provides faster onset of action and higher intensity of action at peak activity level of cannabis. Moreover, the absorption enhancer has no effect on the duration of action of cannabis.

Example 3

Onset and duration of action of orally administered cannabis/SNAC composition at a low SNAC dose. This study was designed to assess the utility of SNAC in enabling a rapid-acting oral form of cannabis at a low dose.

Selection of Participants. Three study participants were recruited to ingest cannabis compositions and record the onset, duration, and intensity of cannabis-induced euphoria and/or dysphoria. Study participants took part in two separate tests: 1) use of a control substance, which included liquid cannabis extract dissolved in aqueous ethanol, and 2) use of a test substance, which included the liquid cannabis extract dissolved in aqueous ethanol, as well as SNAC.

Formulations. The selected cannabis concentrate is commercially available and was provided to participants in an ethanol solution. The concentrate contains 8 mg THC per dose. It was selected because it contains a high percentage of THC, which provides a noticeable effect on user-reported "euphoria". Aqueous ethanol was used as solvent because it effectively dissolves cannabis extract, as well as SNAC.

Methods. For the Control experiment, each participant mixed the cannabis concentrate with 15 ml (one tablespoon) of aqueous ethanol, and immediately swallowed the mixture.

For the Test experiment, each participant mixed the cannabis concentrate with a pre-mixed solution of aqueous ethanol and 100 mg SNAC, and immediately swallowed the dissolved mixture.

For both the Control experiment and the Test experiment, each participant recorded the time of dose administration, the time of onset of euphoria and/or dysphoria, and the observed level of euphoria and/or dysphoria in fifteen minute intervals for five hours following administration of the cannabis dose. Euphoria and dysphoria were reported using a scale value, in a range from 1-10. Table 1 shows descriptions of euphoria and dysphoria levels for each scale value.

Figure 7:
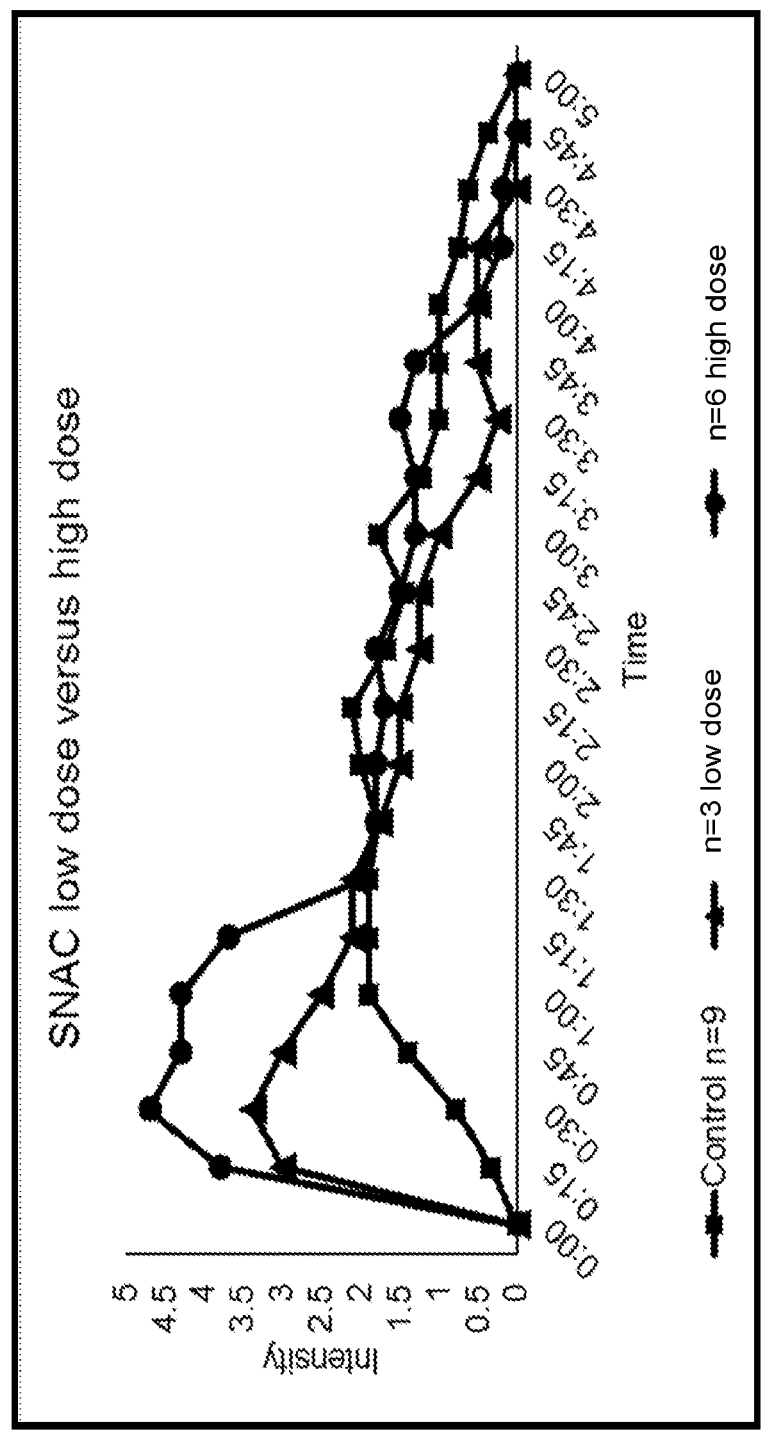
FIG. 7 shows a comparison of intensity, duration and onset of action of orally administered cannabis formulations with a high SNAC dose (200 mg, "high dose"), a low SNAC dose (100 mg, "low dose") and no SNAC ("control").

Results. The results are combined with the data from Example 2 and are reported for all participants in FIG. 7.

Onset: All three participants reported euphoria within five minutes of ingesting the cannabis/SNAC formulation (Test), with the time of onset ranging between two and five minutes. In contrast, the first time-point of euphoria reported by participants after ingestion of the cannabis-only formulation (Control) was fifteen minutes post-ingestion, with the time of onset ranging between fifteen minutes and one hour, fifteen minutes. By fifteen minutes post-ingestion, the average reported euphoria scale value was 3.0 for the cannabis/SNAC formulation (Test). In contrast, fifteen minutes after ingestion of the cannabis-only formulation (Control), the average reported euphoria scale value was 0.25.

Intensity: The average peak euphoria scale value after ingestion of the cannabis/SNAC formulation (Test) was 3.4, which occurred thirty minutes post-ingestion. In contrast, the highest average euphoria scale value after ingestion of the cannabis-only formulation (Control) was 2.2, which was at the two hour, fifteen minute time-point. Compared to Example 2 where the SNAC dose was 200 mg, the participants in Example 3 ingested only 100 mg of SNAC combined with the same quantity of cannabis used in Example 2. This reduced quantity of SNAC resulted in a reduced cannabis effect demonstrating a clear dose-response relationship between observed cannabis effect (euphoria) and SNAC dose. Consistent with Example 2, ingestion of the cannabis/SNAC formulation led to a higher peak intensity of euphoria, which occurred an average of one hour and forty-five minutes faster than when the cannabis-only formulation was ingested.

Duration: The results indicate that the addition of an absorption enhancer does not shorten the duration of action of cannabis.

In summary, adding an absorption enhancer, such as SNAC, in an oral dosage formulation of cannabis provides faster onset of action and higher intensity of action at peak activity level of cannabis. Moreover, the absorption enhancer has no effect on the duration of action of cannabis. The varying quantity of SNAC produces a clear dose-response relationship between observed cannabis effect (euphoria) and SNAC dose.

Example 4

Figure 8:
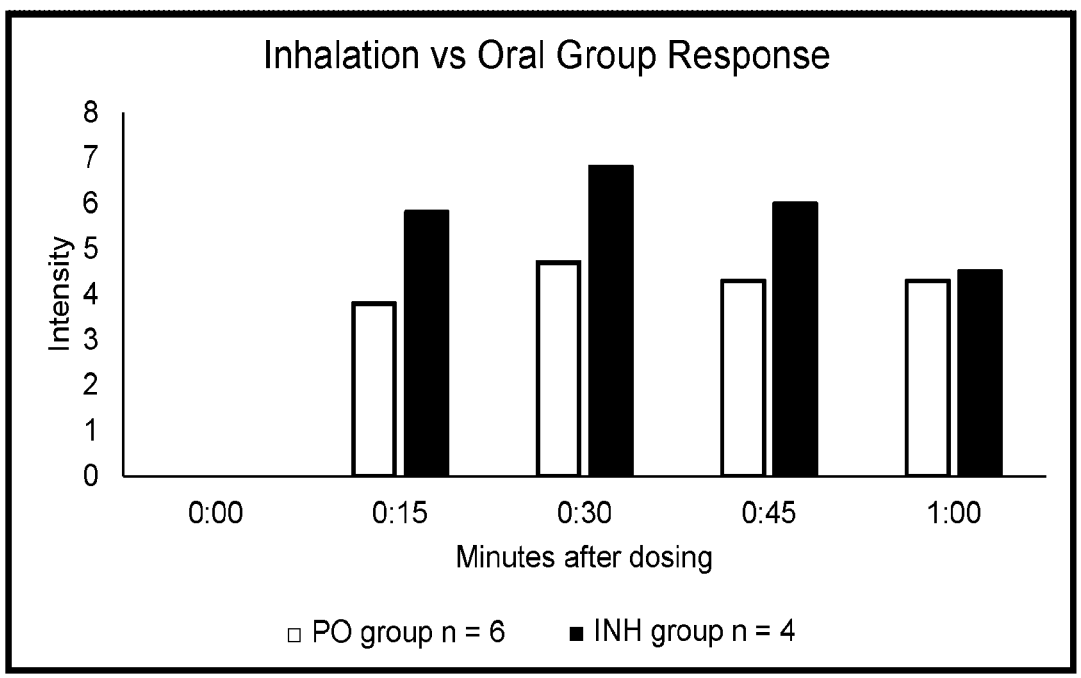
FIG. 8 shows intensity, duration and onset of action of cannabis formulated with SNAC administered orally ("PO") compared to cannabis administered by inhalation ("INH").
Figure 8:
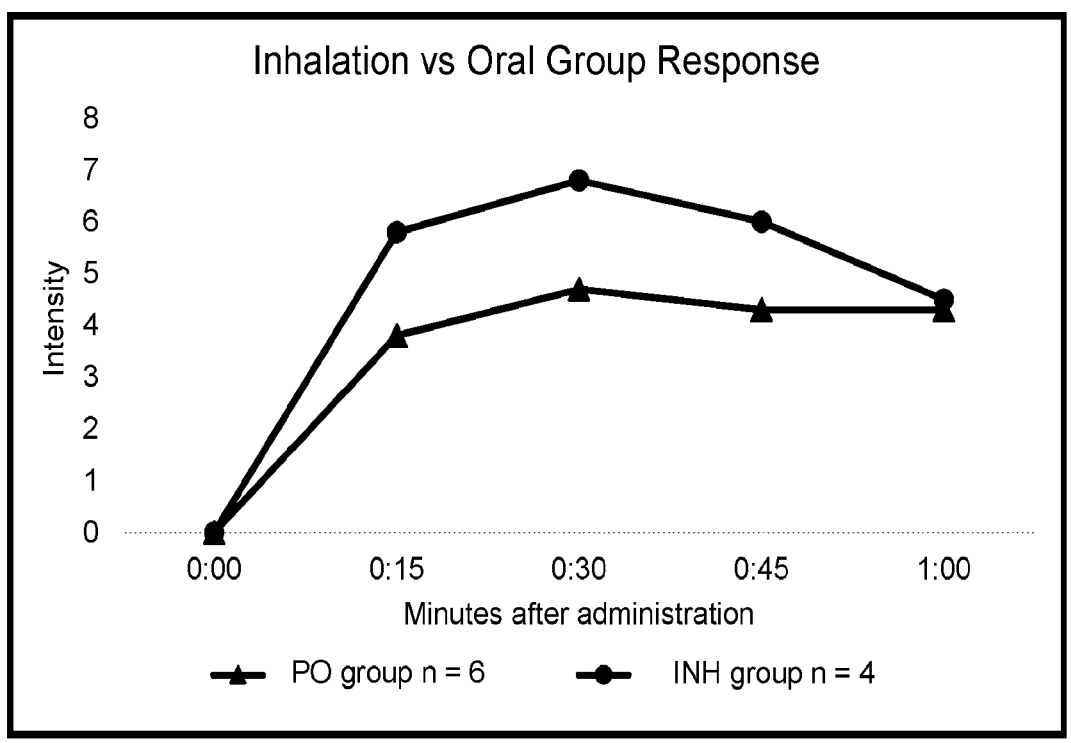

Inhalation versus oral group response (FIG. 8). Comparison of the pharmacodynamic response to inhaled and oral cannabis measured as subject-reported euphoria. Both the oral and inhaled groups reported similar time to peak effect (15-30 minutes). This is very surprising because oral cannabis is traditionally characterized by a very slow time to peak effect (up to 4 hours).

Example 5

Summary of cannabis/SNAC oral rat pharmacokinetic (PK) study. The study was designed to characterize the pharmacokinetic profile of cannabis extract containing 56% THC/CBD in a 1:1 ratio (by weight) with and without the excipient, SNAC, following a single oral gavage administration to rats. In this study two doses of cannabis and SNAC and two ratios of cannabis to SNAC were tested. The experimental design is presented in Table 4 below.

TABLE 4

Experimental design.

| Group Nos | Group Designation | Extract[1] Dose Level (mg/kg) | SNAC Dose Level (mg/kg) | Dose Volume (mL/kg) | Dose Concentration[2] (mg API/mL) | Dose Concentration[3] (mg SNAC/mL) | Number of Males |
|---|---|---|---|---|---|---|---|
| 1 | Excipient Control | 0 | 500 | 2 | 0 | 250 | 6 |
| 2 | Cannabis Control | 25 | 0 | 2 | 12.5 | 0 | 6 |

TABLE 4-continued

Experimental design.

| Group Nos | Group Designation | Extract[1] Dose Level (mg/kg) | SNAC Dose Level (mg/kg) | Dose Volume (mL/kg) | Dose Concentration[2] (mg API/mL) | Dose Concentration[3] (mg SNAC/mL) | Number of Males |
|---|---|---|---|---|---|---|---|
| 3 | Low Dose | 25 | 250 | 2 | 12.5 | 125 | 6 |
| 4 | Mid Dose | 25 | 500 | 2 | 12.5 | 250 | 6 |
| 5 | High Dose | 50 | 500 | 2 | 25 | 250 | 6 |

[1]Extract contains 54% by weight (27% THC + 27% CBD) as the API (Active Pharmaceutical Ingredient)
[2]Dose of *cannabis* extract contains a mixture of THC:CBD in a ratio of 1:1 by weight
[3]SNAC dose is 10 times (THC + CBD) dose for groups 3 and 5 and 20 times for group 4.

Methods. Animals were dosed on Day 1 and a series of blood samples were collected over a period of 4 hours post dose for pharmacokinetic evaluation. Animals were euthanized following collection of their last blood sample.

Results. Following a single oral administration of cannabis extract containing THC/CBD in a 1:1 ratio combined with the absorption enhancing excipient (SNAC) at 25 mg extract/kg and 250 mg SNAC/kg (Group 3), 25 mg extract/kg and 500 mg SNAC/kg (Group 4), or 50 mg extract/kg and 500 mg SNAC/kg (Group 5), mean maximum concentration $C_{max}$ ranged from 31.7 to 159.3 ng/mL for CBD and from 111.5 to 546.17 ng/mL for THC. The time to reach the mean maximum plasma concentration ($T_{max}$) ranged from 0.25 to 1 hour post dose for CBD and was reached at 1 hour post dose for the low and mid dose groups and at 2 hours post dose for the high dose group for THC. The $AUC_{0-Tlast}$ ranged from 13.17 to 382.14 hr*ng/mL for CBD and from 170.64 to 1256.49 hr*ng/mL for THC.

Figure 10:
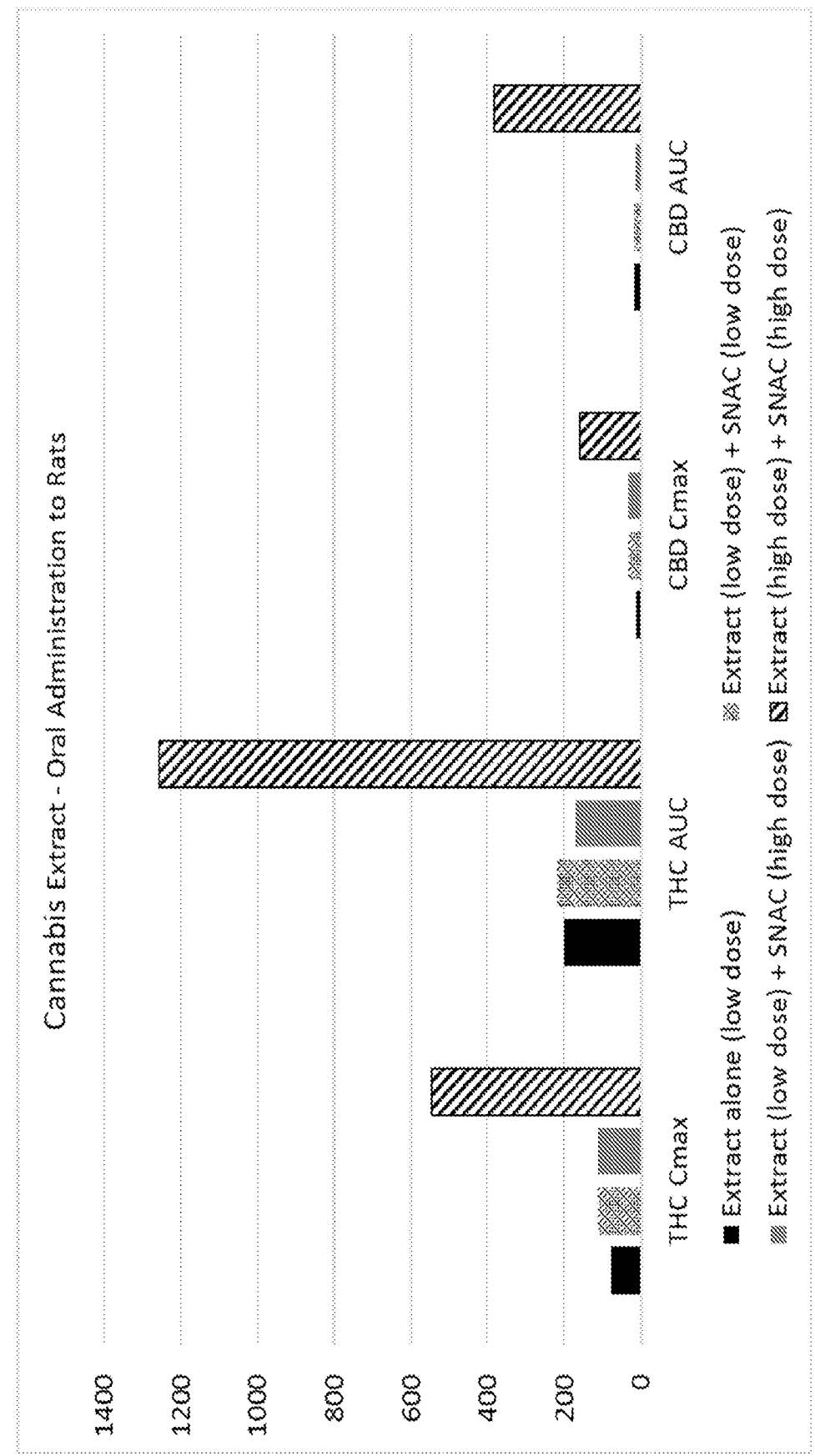
FIG. 10 shows THC and CBD $C_{max}$ (ng/ml) and AUC (hr*ng/mL) following a single oral administration to rats.

Over the dose range tested, $C_{max}$ and $AUC_{0-Tlast}$ for THC was higher than for CBD. When administering the same cannabis extract (THC/CBD) dose (25 mg/kg total cannabinoid dose; 12.5 mg/kg THC/12.5 mg/kg CBD) with and without SNAC, for THC, a 1.4-fold $C_{max}$ increase over cannabis alone was observed at SNAC doses of either 250 or 500 mg/kg. AUC was 1.1-fold greater in the 250 mg/kg SNAC group, but lower in the 500 mg/kg SNAC group, compared to the cannabis alone group. For CBD, 2.9-fold and 2.8-fold $C_{max}$ increases over cannabis alone were observed at SNAC doses of either 250 or 500 mg/kg. AUC was lower in both groups, compared to the cannabis alone group. Increasing both the cannabis and SNAC doses 2-fold to 500 mg/kg SNAC and 50 mg/kg cannabis extract (25 mg/kg THC/25 mg/kg CBD), resulted in a 14.2-fold increase in the CBD $C_{max}$ and a 6.9-fold increase in the THC $C_{max}$. $AUC_{0-Tlast}$ for CBD and THC, were increased 22.1-fold and 6.3-fold, respectively (FIG. 9 and FIG. 10). Over the dose range tested, $C_{max}$ and $AUC_{0-Tlast}$ for THC was higher than for CBD. When administering the same cannabis extract (THC/CBD) dose in the presence of SNAC (250 mg/kg or 500 mg/kg), both THC and CBD $C_{max}$ were increased 1.4-fold and 2.8-fold, respectively, over the cannabis alone group. $AUC_{0-Tlast}$ were comparable. This observation suggests that a cannabis to SNAC ratio of 10:1 facilitates an increase in $C_{max}$, but increasing the ratio to 20:1 provides no additional benefit. Increasing both the cannabis and SNAC doses by 2-fold resulted in THC and CBD $C_{max}$ increases of 6.9-fold and 14.2-fold, respectively, over the cannabis alone group. $AUC_{0-Tlast}$ for THC and CBD increased by 6.3-fold and 22.1-fold, respectively, over the cannabis alone group. This is a greater than expected increase based on the near linear dose response observed for oral cannabis (Information for Health Care Providers—Cannabis and the Cannabinoids; Health Canada February 2013). Overall, these data suggest that SNAC enhances cannabis absorption when administered to rats by oral gavage.

Example 6

Onset and duration of action of orally administered cannabis/NAC composition. This study was designed to assess the utility of the acid form of SNAC, N-[8-(2-hydroxybenzoyl) amino] caprylic acid (NAC), in enabling a rapid-acting oral form of cannabis.

Study Participant. One study participant was recruited to ingest cannabis compositions and record the onset, duration, and intensity of cannabis-induced euphoria and/or dysphoria. The study participant took part in two separate tests: 1) use of a control substance, which included cannabis concentrate oil in an herbal extract blend dissolved in aqueous ethanol, and 2) use of a test substance, which included the cannabis concentrate oil in an herbal extract blend dissolved in aqueous ethanol, as well as NAC.

Formulations. The selected cannabis concentrate oil is commercially available in a capsule and the contents of the capsule were provided to the participant in an ethanol solution. One capsule contains 9 mg CBD, 7.7 mg THC, herbal extract blend (Magnolia bark, Ashwagandha, Astragalus), and stearic acid (from vegetable oil), and the stated potency per capsule is: CBD 9.0 mg, THCA 0.0 mg and THC 7.6 mg. The formulation was selected because it provides a noticeable effect on user-reported "euphoria", and the CBD content should ameliorate dysphoric effects if Test 2 delivers a very high dose of cannabinoids.

Methods. For the Control experiment, the participant mixed the cannabis concentrate with 15 ml (one tablespoon) of aqueous ethanol, and immediately swallowed the mixture.

For the Test experiment, the participant mixed the cannabis concentrate with 5 ml pre-mixed solution of aqueous ethanol and 100 mg NAC, and immediately swallowed the dissolved mixture.

For both the Control experiment and the Test experiment, the participant recorded the time of dose administration, the time of onset of euphoria and/or dysphoria, and the observed level of euphoria and/or dysphoria in fifteen minute intervals for five hours following administration of the cannabis dose. Euphoria and dysphoria were reported using a scale value, in a range from 1-5. Table 5 shows descriptions of euphoria and dysphoria levels for each scale value.

TABLE 5

Scale Values for Reporting Euphoria and Dysphoria

| Scale Value | Description |
|---|---|
| 0 | No observed effect |
| 1 | Mild observed effect; possibly psychological |

TABLE 5-continued

Scale Values for Reporting Euphoria and Dysphoria

| Scale Value | Description |
|---|---|
| 2 | Definite but mild effect |
| 3 | Definite substantial effect |
| 4 | Strong effect |
| 5 | Intense effect |

Results. The results shown below are scale values obtained for the participant in the control experiment (Table 6) and in the test experiment (Table 7). The values are plotted in FIG. 11.

TABLE 6

Control Experiment (n = 1)

| Actual Time 11:13 AM | Time from Start 0:00 | Observed "Euphoria" (0-5) | Observed "Dysphoria" (0-5) |
|---|---|---|---|
| 11:28 AM | :15 | 0 | 0 |
| 11:43 AM | :30 | 1 | 0 |
| 11:58 AM | :45 | 2 | 0 |
| 12:13 PM | 1:00 | 2 | 0 |
| 12:28 PM | 1:15 | 3 | 1 |
| 12:43 PM | 1:30 | 3 | 1 |
| 12:58 PM | 1:45 | 3 | 1 |
| 1:13 PM | 2:00 | 4 | 1 |
| 1:28 PM | 2:15 | 4 | 1 |
| 1:43 PM | 2:30 | 4 | 1 |
| 1:58 PM | 2:45 | 3 | 0 |
| 2:13 PM | 3:00 | 3 | 0 |
| 2:28 PM | 3:15 | 3 | 0 |
| 2:43 PM | 3:30 | 2 | 0 |
| 2:58 PM | 3:45 | 2 | 0 |
| 3:13 PM | 4:00 | 2 | 0 |
| 3:28 PM | 4:15 | 1 | 0 |
| 3:43 PM | 4:30 | 1 | 0 |
| 3:58 PM | 4:45 | 0 | 0 |
| 4:13 PM | 5:00 | 0 | 0 |

TABLE 7

Test Experiment (n = 1)

| Actual Time 11:20 AM | Time from Start 0:00 | Observed "Euphoria" (0-5) | Observed "Dysphoria" (0-5) |
|---|---|---|---|
| 11:24 AM | :04 | 1 | 0 |
| 11:26 AM | :06 | 2 | 0 |
| 11:35 AM | :15 | 3 | 1 |
| 11:50 AM | :30 | 4 | 0 |
| 12:05 PM | :45 | 4 | 0 |
| 12:20 PM | 1:00 | 4 | 0 |
| 12:35 PM | 1:15 | 4 | 0 |
| 12:50 PM | 1:30 | 3 | 0 |
| 1:05 PM | 1:45 | 3 | 0 |
| 1:20 PM | 2:00 | 3 | 0 |
| 1:35 PM | 2:15 | 2 | 0 |
| 1:50 PM | 2:30 | 2 | 0 |
| 2:05 PM | 2:45 | 2 | 0 |
| 2:20 PM | 3:00 | 1 | 0 |
| 2:35 PM | 3:15 | 1 | 0 |
| 2:50 PM | 3:30* | 0 | 0 |

*experiment ended

Onset: The participant reported euphoria within six minutes of ingesting the cannabis/NAC formulation (Test, Table 7 and FIG. 11). In contrast, the first time-point of euphoria reported by the participant after ingestion of the cannabis-only formulation (Control, Table 6 and FIG. 11) was forty-five minutes post-ingestion. By thirty minutes post-ingestion, the participant reported strong euphoria (scale value of 4) for the cannabis/NAC formulation. In contrast, thirty minutes after ingestion of the cannabis-only formulation, the participant only observed a mild effect that was possibly psychological (scale value of 1).

Intensity: The peak euphoria scale value after ingestion of both the cannabis-only (Control) and cannabis/NAC formulations (Test) was 4. However, peak intensity of euphoria was reached thirty minutes post-ingestion with the cannabis/NAC formulation (Test), whereas peak intensity of euphoria was reached two hours post-ingestion with the cannabis-only formulation (Control). Therefore, ingestion of the cannabis/NAC formulation led to a peak intensity of euphoria that occurred one hour and thirty minutes faster than when the cannabis-only formulation was ingested. The intensity of observed dysphoria was minimal for both the Test and Control, although the participant observed more mild dysphoria effects with the cannabis-only formulation (Control).

In summary, NAC, the acid form of SNAC, behaves similarly to SNAC when included in an oral dosage formulation of cannabis. A cannabis/NAC formulation provides faster onset of action as compared to a cannabis-only formulation.

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. In particular embodiments, a material effect would cause a statistically-significant reduction in an administration benefit when assessed in an experimental protocol disclosed herein. In particular embodiments, a material effect would cause a statistically significant reduction in increased absorption of a measured component of vegetable matter, increased bioavailability of a measured component of vegetable matter, faster onset of action of a measured component of vegetable matter, higher peak concentrations of a measured component of vegetable matter, and/or faster time to peak concentrations of a measured component of vegetable matter as assessed by mean maximum concentration $C_{max}$, time to reach the mean maximum plasma concentration $T_{max}$, and/or Area Under the Curve (AUC).

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, $3^{rd}$ Edition or a dictionary known to those of ordinary skill in the art, such as the Oxford Dictionary of Biochemistry and Molecular Biology (Ed. Anthony Smith, Oxford University Press, Oxford, 2004).

What is claimed is:

1. A method of providing increased bioavailability of a cannabinoid with an aqueous solubility of less than 0.1 mg/ml in an oral formulation, the method comprising
    adding an N-acylated fatty amino acid or salt thereof comprising the formula:

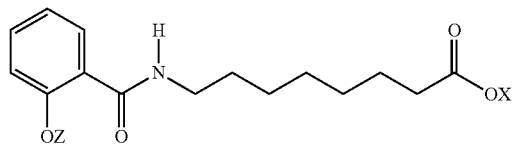

to the oral formulation
    wherein X and Z are independently hydrogen, a monovalent cation, a divalent metal cation, or an organic cation, and
    wherein the N-acylated fatty amino acid or salt thereof is added in an amount that is one to twenty times the amount of the cannabinoid in the oral formulation, thereby providing increased bioavailability when compared to the same oral formulation without the added N-acylated fatty amino acid or salt thereof.

2. The method of claim 1, wherein the cannabinoid with an aqueous solubility of less than 0.1 mg/ml comprises tetrahydrocannabinol (THC) and/or cannabidiol (CBD).

3. The method of claim 1, wherein the cannabinoid with an aqueous solubility of less than 0.1 mg/ml is derived from cannabis.

4. The method of claim 3, wherein the *cannabis* is selected from *Cannabis sativa, Cannabis ruderalis*, and *Cannabis* indica.

5. The method of claim 1, wherein the cannabinoid comprises tetrahydrocannabinol (THC), cannabidiol (CBD), cannabigerol (CBG), cannabichromene (CBC), cannabinol (CBN), cannabinodiol (CBDL), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), cannabinerolic acid, cannabidiolic acid (CBDA), cannabinol propyl variant (CBNV), cannabitriol (CBO), tetrahydrocannabinolic acid (THCA), tetrahydrocannabivarinic acid (THCVA) or mixtures thereof.

6. The method of claim 1, wherein X is selected from: hydrogen; sodium or potassium as the monovalent cation; calcium or magnesium as the divalent metal cation; or tetramethylammonium as the organic cation.

7. The method of claim 1, wherein Z is selected from: hydrogen; sodium or potassium as the monovalent cation; or calcium or magnesium as the divalent metal cation.

8. The method of claim 1, wherein the N-acylated fatty amino acid or salt thereof is selected from the group consisting of monosodium-N-salicyloyl-8-aminocaprylate, disodium-N-salicyloyl-8-aminocaprylate, and N-(salicyloyl)-8-aminocaprylic acid.

9. The method of claim 1, wherein X is sodium and Z is hydrogen.

10. The method of claim 1, wherein X is hydrogen and Z is hydrogen.

11. The method of claim 1, wherein X is hydrogen and Z is sodium.

12. The method of claim 1, wherein X is sodium and Z is sodium.

13. The method of claim 1, wherein the N-acylated fatty amino acid or salt thereof is added in an amount that is one to ten times the amount of the cannabinoid.

14. The method of claim 1, wherein the adding comprises adding 100-200 mg of the N-acylated fatty amino acid to the oral formulation.

15. The method of claim 1, wherein the oral formulation comprises up to 1 gram of the cannabinoid.

16. The method of claim 1, wherein the oral formulation further comprises flavonoid compounds, terpenes, or terpenoids.

17. The method of claim 1, wherein the oral formulation further comprises an excipient.

18. The method of claim 17, wherein the excipient comprises a surfactant, a flavorant, or a sweetener.

19. The method of claim 1, wherein the oral formulation comprises a solution formulation or a suspension formulation.

20. The method of claim 19, wherein the solution formulation or the suspension formulation is within a gelcap.

* * * * *